US011796534B2

(12) United States Patent
Kodama et al.

(10) Patent No.: US 11,796,534 B2
(45) Date of Patent: Oct. 24, 2023

(54) METHODS FOR ASSESSING CELL SURFACE GLYCOSYLATION

(71) Applicant: Juno Therapeutics, Inc., Seattle, WA (US)

(72) Inventors: Paul Ken Kodama, Seattle, WA (US); Tom Kowski, Seattle, WA (US); Mima Mujacic, Seattle, WA (US); Kenneth Mayo Prentice, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 802 days.

(21) Appl. No.: 16/604,547

(22) PCT Filed: Apr. 13, 2018

(86) PCT No.: PCT/US2018/027666
§ 371 (c)(1),
(2) Date: Oct. 10, 2019

(87) PCT Pub. No.: WO2018/191723
PCT Pub. Date: Oct. 18, 2018

(65) Prior Publication Data
US 2021/0255173 A1    Aug. 19, 2021

Related U.S. Application Data

(60) Provisional application No. 62/515,515, filed on Jun. 5, 2017, provisional application No. 62/485,897, filed on Apr. 14, 2017.

(51) Int. Cl.
G01N 33/53      (2006.01)
C12Q 1/34       (2006.01)
G01N 33/50      (2006.01)

(52) U.S. Cl.
CPC ........... G01N 33/5308 (2013.01); C12Q 1/34 (2013.01); C12Y 305/01052 (2013.01);
(Continued)

(58) Field of Classification Search
None
See application file for complete search history.

(56) References Cited

U.S. PATENT DOCUMENTS 4,452,773 A    6/1984 Molday
4,795,698 A    1/1989 Owen
(Continued)

FOREIGN PATENT DOCUMENTS

EP    0304663    4/1992
EP     452342    11/1994
(Continued)

OTHER PUBLICATIONS

US 8,252,592 B2, 08/2012, Jensen (withdrawn)
(Continued)

*Primary Examiner* — Erin M. Bowers
(74) *Attorney, Agent, or Firm* — MORRISON & FOERSTER LLP

(57) ABSTRACT

Provided herein are methods for assessing cell surface glycans, e.g., N-glycans, by assessing a sample of released surface glycans, and determining the presence, absence, or level of glycans present in the sample. Also provided are methods of assaying and/or evaluating a cell composition by assessing the cell surface glycan profile of the cell composition and comparing the profile to a reference sample. Methods for manufacturing and/or culturing a plurality of cell compositions having consistent surface glycan expression with low variability are also provided.

28 Claims, 19 Drawing Sheets
Specification includes a Sequence Listing.

(52) U.S. Cl.
CPC ....... *G01N 33/502* (2013.01); *G01N 2400/10* (2013.01); *G01N 2570/00* (2013.01)

(56) References Cited

U.S. PATENT DOCUMENTS

| | | | |
|---|---|---|---|
| 5,200,084 | A | 4/1993 | Liberti |
| 5,219,740 | A | 6/1993 | Miller et al. |
| 6,040,177 | A | 3/2000 | Riddell |
| 6,207,453 | B1 | 3/2001 | Maass et al. |
| 6,410,319 | B1 | 6/2002 | Raubitschek et al. |
| 6,451,995 | B1 | 9/2002 | Cheung et al. |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen et al. |
| 7,446,190 | B2 | 11/2008 | Sadelain et al. |
| 7,446,191 | B2 | 11/2008 | Jensen |
| 8,324,353 | B2 | 12/2012 | Jensen |
| 8,339,645 | B2 | 12/2012 | Nakawaki |
| 8,389,282 | B2 | 3/2013 | Sadelain et al. |
| 8,479,118 | B2 | 7/2013 | Lyndersay et al. |
| 8,802,374 | B2 | 8/2014 | Jensen |
| 8,822,647 | B2 | 9/2014 | Jensen |
| 8,911,993 | B2 | 12/2014 | June et al. |
| 9,233,125 | B2 | 1/2016 | Davila et al. |
| 2002/0131960 | A1 | 9/2002 | Sadelain et al. |
| 2002/0150914 | A1 | 10/2002 | Anderson et al. |
| 2003/0223994 | A1 | 12/2003 | Hoogenboom et al. |
| 2004/0191260 | A1 | 9/2004 | Reiter et al. |
| 2006/0034850 | A1 | 2/2006 | Weldanz et al. |
| 2007/0099253 | A1 | 5/2007 | Erkhov et al. |
| 2007/0116690 | A1 | 5/2007 | Yang et al. |
| 2009/0226474 | A1 | 9/2009 | Weldanz et al. |
| 2009/0304679 | A1 | 12/2009 | Weldanz et al. |
| 2011/0003380 | A1 | 1/2011 | Miltenyi |
| 2013/0149337 | A1 | 6/2013 | Cooper et al. |
| 2013/0287748 | A1 | 10/2013 | June et al. |
| 2014/0179011 | A1 | 6/2014 | Brousmiche et al. |
| 2014/0242709 | A1 | 8/2014 | Brousmiche et al. |
| 2014/0271635 | A1 | 9/2014 | Brodgon et al. |
| 2014/0294841 | A1 | 10/2014 | Scheinberg et al. |

FOREIGN PATENT DOCUMENTS

| | | |
|---|---|---|
| EP | 2537416 | 11/2014 |
| JP | H01105160 | 4/1989 |
| JP | 2009142238 | 7/2009 |
| JP | 2013007742 | 1/2013 |
| JP | 2015091953 | 5/2015 |
| WO | WO1990/014421 | 11/1990 |
| WO | WO1992008796 | 5/1992 |
| WO | WO1994/028143 | 12/1994 |
| WO | WO 1996/013593 | 5/1996 |
| WO | WO 1996/018105 | 6/1996 |
| WO | WO 1999/018129 | 4/1999 |
| WO | WO 1999/060120 | 11/1999 |
| WO | WO 2000/014257 | 3/2000 |
| WO | WO 2003/020763 | 3/2003 |
| WO | WO 2003/068201 | 8/2003 |
| WO | WO 2004/033685 | 4/2004 |
| WO | WO 2006/000830 | 1/2006 |
| WO | WO 2008/128228 | 10/2008 |
| WO | WO 2009/072003 | 6/2009 |
| WO | WO 2010/033140 | 3/2010 |
| WO | WO 2011/044186 | 4/2011 |
| WO | WO 2011/105544 | 9/2011 |
| WO | WO 2012/129514 | 9/2012 |
| WO | WO 2013/071154 | 5/2013 |
| WO | WO 2013/123061 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2015/075139 | 5/2015 |
| WO | WO 2016/030414 | 3/2016 |
| WO | WO 2016/036705 | 3/2016 |
| WO | WO 2018/027197 | 2/2018 |
| WO | WO 2020/056047 | 3/2020 |

OTHER PUBLICATIONS

Redelinghuys et al., J. Biol. Chem. 286(40): 34522-34532 (2011).*
Lauber et al., "Rapid Preparation of Released N-Glycans for HILIC Analysis Using a Novel Fluorescence and MS-Active Labeling Reagent," Application Note from Waters Corporation (waters.com), Jan. 2015.*
Nakano et al., Mol. Cell. Proteomics 10: 1-12 (2011).*
Alonso-Camino et al., "CARbodies: Human Antibodies Against Cell Surface Tumor Antigens Selected From Repertoires Displayed on T Cell Chimeric Antigen Receptors," Mol Ther Nucleic Acids (2013) 2(5):e93.
Anumula et al., "Advances in Fluorescence Derivatization Methods for High-Performance Liquid Chromatographic Analysis of Glycoprotein Carbohydrates," Anal Biochem (2006) 350(1): 1-23.
Barrett et al., "Chimeric antigen receptor therapy for cancer," Annu Rev Med. (2014);65:333-47.
Bateman et al., "Glycan analysis and influenza A virus infection of primary swine respiratory epithelial cells: the importance of NeuAc{alpha}2-6 glycans." J Biol Chem. Oct. 29, 2010;285(44):34016-34026.
Boris-Lawrie et al., "Recent advances in retrovirus vector technology," Cur. Opin. Genet. Develop. (1993) 3:102-109.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Burns et al., "Vesicular stomatitis virus G glycoprotein pseudotyped retroviral vectors concentration to very high titer and efficient gene transfer into mammalian and nonmammalian cells," Proc. Natl. Acad. Sci. USA (1993) 90:8033-8037.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Cavalieri et al., "Human T lymphocytes transduced by lentiviral vectors in the absence of TCR activation maintain an intact immune competence," Blood (2003) 102(2): 497-505.
Cheadle et al., "Chimeric antigen receptors for T-cell based therapy," Methods Mol Biol. (2012);907:645-66.
Chervin et al., "Engineering higher affinity T cell receptors using a T cell display system," J Immunol Methods, (2008) 339(2):175-84.
Chicaybam et al., "An efficient low cost method for gene transfer to T lymphocytes," PLoS ONE (2013) 8(3): e60298.
Cho et al. "Human mammalian cell sorting using a highly integrated microfabricated fluorescence-activated cell sorter (pFACS)," Lab Chip (2010) 10:1567-1573.
Chothia et al., "The outline structure of the T-cell alpha beta receptor," EMBO J. (1988) 7(12):3745-3755.
Clackson, T. et al. "Making Antibody Fragments Using Phage Display Libraries," Nature (1991) 352:624-628.
Clarke and Davies in: Methods in Molecular Medicine, vol. 58: Metastasis Research Protocols, vol. 2: Cell Behavior In Vitro and In Vivo, Edited by: S. A. Brooks and U. Schumacher© Humana Press Inc., Totowa, NJ (2001) pp. 17-25.
Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5):324-332.
Comelli et al., "Activation of Murine CD4+ and CD8+ T Lymphocytes Leads to Dramatic Remodeling of N-linked Glycans," J Immunol (2006) 177(4): 2431-2440.
Cooper et al., "T-cell clones can be rendered specific for CD19: toward the selective augmentation of the graft-versus-B-lineage leukemia effect," Blood (2003) 101:1637-1644.

(56) References Cited

OTHER PUBLICATIONS

Davila et al., "CD19 CAR-targeted T cells induce long-term remission and B Cell Aplasia in an immunocompetent mouse model of B cell acute lymphoblastic leukemia," PLoS ONE (2013) 8(4):e61338.
De Felipe, "Skipping the co-expression problem: the new 2A "Chysel" technology," Genet Vaccines Ther (2004) Sep. 13;2(1):13.
De Felipe, "Targeting of proteins derived from self-processing polyproteins containing multiple signal sequences," Traffic (2004) 5(8):616-626.
Earl et al., "CD45 Glycosylation Controls T-cell Life and Death," Immunol Cell Biol (2008) 86(7): 608-615.
Eshghi et al., "Imaging of N-Linked Glycans from Formalin-Fixed Paraffin-Embedded Tissue Sections Using MALDI Mass Spectrometry." ACS Chemical Biology 2014 9(9): 2149-2156.
Fedorov et al., "PD-1- and CTLA-4-based inhibitory chimeric antigen receptors (iCARs) divert off-target immunotherapy responses," Sci Transl Med. (2013) 5(215):215ra172.
Gan et al., "Native Mass Spectrometry of Recombinant Proteins From Crude Cell Lysates," Anal Chem (2017) 89(8): 4398-4404.
Gimenez et al., "Quantitative analysis of N-glycans from human alfa-acid-glycoprotein using stable isotope labeling and zwitterionic hydrophilic interaction capillary liquid chromatography electrospray mass spectrometry as tool for pancreatic disease diagnosis." Anal Chim Acta. (2015) 866:59-68.
Godin et al., "Microfluidics and photonics for Bio-System-on-a-Chip: a review of advancements in technology towards a microfluidic flow cytometry chip," J Biophotonics (2008) 1(5):355-376.
Gotze et al., "Diagnosis of toxoplasmosis using a synthetic glycosylphosphatidylinositol glycan." Angew Chem Int Ed Engl. (2014) 53(50):13701-13705.
Hall et al., "Cell Surface N-glycans Influence the Level of Functional E-cadherin at the Cell-Cell Border," FEBS Open Bio (2014) 4: 892-897.
Hara et al., "Determination of mono-O-acetylated N-acetylneuraminic Acids in Human and Rat Sera by Fluorometric High-Performance Liquid Chromatography," Anal Biochem (1989) 179(1): 162-66.
Holler et al., "In vitro evolution of a T cell receptor with high affinity for peptide/MHC," Proc Natl Acad Sci USA, (2000) 97(10):5387-92.
Holler et al., "TCRs with high affinity for foreign pMHC show self-reactivity," Nat Immunol (2003) 4(1):55-62.
Huang et al., "DNA transposons for modification of human primary T lymphocytes," Methods Mol Biol (2009) 506: 115-126.
Hudecek et al., "Receptor affinity and extracellular domain modifications affect tumor Yecognition by ROR1-specific chimeric antigen receptor T cells," Clin Cancer Res. Jun. 15, 2013;19(12):3153-3164.
Isailovic et al., "Delineating diseases by IMS-MS profiling of serum N-linked glycans." J Proteome Res. (2012) 11(2):576-85.
Janeway et al., Immunobiology: The Immune System in Health and Disease, 3rd ED., Current Biology Publications (1997), p. 4:33.
Johnston, "Biolistic transformation: microbes to mice," Nature (1990) 346:776-777.
Jores et al., "Resolution of hypervariable regions in T-cell receptor beta chains by a modified Wu-Kabat index of amino acid diversity.," PNAS (1990) 87(23):9138-9142.
Kindt et al., Kuby Immunology 6th ed., W.H. Freeman and Co. (2007) p. 91.
Klebanoff et al., "Sorting through subsets: Which T cell populations mediate highly effective adoptive immunotherapy?," J Immunother. (2012) 35(9): 651-660.
Kochenderfer et al., "Treating B-cell cancer with T cells expressing anti-CD19 chimeric antigen receptors," Nature Reviews Clinical Oncology (2013) 10, 267-276.
Koste et al., "T-cell receptor transfer into human T cells with ecotropic retroviral vectors," Gene Therapy (2014) 21: 533-538.
Kotb, "Bacterial pyrogenic exotoxins as superantigens," Clinical Microbiology Reviews, K1995) 8:411-426.
Kurucz et al., "A bacterially expressed single-chain Fv construct from the 2B4 T-cell receptor," PNAS (1993) 90(9):3830-3834.

Lauber et al., "Rapid Preparation of Released N-Glycans for HILIC Analysis Using a Novel Flourescence and MS-Active Labeling Reagent," Application Note from Waters Corporation (Waters.com) downloaded Mar. 28, 2017.
Lefranc et al., "IMGT unique numbering for immunoglobulin and T cell receptor variable domains and Ig superfamily V-like domains," Dev Comp Immunol (2003) 27(1):55-77.
Li et al., "Directed evolution of human T-cell receptors with picomolar affinities by phage display," Nat Biotechnol. (2005) 23:349-354.
Li et al., "Glycosylation and Stabilization of Programmed Death ligand-1 Suppresses T-cell Activity," Nat Commun (2016) 7: 12632.
Ling et al., "B-cell and plasma cell antigens: new and previously defined clusters," Leucocyte typing 111. (1987) 302-355.
Liu et al., "Cell Surface-Specific N-glycan Profiling in Breast Cancer," PLoS One (2013) 8(8): e72704.
Liu et al., "Inclusion of Strep-tag II in design of antigen receptors for T-cell immunotherapy," Nat Biotechnol (2016) 34(4):430-434.
Lupton et al., "Dominant positive and negative selection using a hygromycin phosphotransferase-thymidine kinase fusion gene," Mol and Cell Biol (1991) 11(6):3374-3378.
Manuri et al., "piggyBac transposon/transposase system to generate CD19-specific T cells for the treatment of B-lineage malignancies," Hum Gene Ther (2010) 21(4): 427-437.
Mehta et al., "Intrinsic Hepatocyte Dedifferentiation Is Accompanied by Upregulation of Mesenchymal Markers, Protein Sialylation and Core Alpha 1,6 Linked Fucosylation," Sci Rep (2016) 6: 27965.
Miller et al., "Improved retroviral vectors for gene transfer and expression," Biotechniques (1989) 7(9):980-982.
Miller et al., "Retrovirus packaging cells," Human Gene Therapy (1990) 1:5-14.
Miwa et al., "Bisected, complex N-glycans and galectins in mouse mammary tumor progression and human breast cancer." Glycobiology (2013) 23(12): 1477-1490.
Nabi et al., "The Galectin Lattice at a Glance," J Cell Sci (2015) 128(13): 2213-2219.
N-Glycosidase F, recombinant. Information Sheet, Roche Applied Science, Content version Jun. 2005.
Norton et al., "Development and Application of a Novel Recombinant Aleuria Aurantia Lectin With Enhanced Core Fucose Binding for Identification of Glycoprotein Biomarkers of Hepatocellular Carcinoma," Proteomics (2016) 16(24): 3126-3136.
Ohta et al., "Expression of Sialyl Lewis(x) Antigen on Human T Cells," Cell Immunol (1993) 151(2): 491-497.
Ouedraogo et al., "Global Analysis of Circulating Immune Cells by Matrix-Assisted Laser Desorption Ionization Time-Of-Flight Mass Spectrometry," PLoS One (2010) 5(10): e13691.
Park et al., "Treating cancer with genetically engineered T cells," Trends Biotechnol. (2011) 29(11): 550-557.
Plummer et al., "Demonstration of peptide:N-glycosidase F Activity in endo-beta-N-acetylglucosaminidase F Preparations," J Biol Chem (1984) 259(17): 10700-10704.
PNGaseF Protocol Prime, User Manual Dated Oct. 14, 2015, N-Zyme Scientifics.
PNGaseF Sheet, QA-Bio, dated Dec. 2, 2014.
Portolano et al., "Lack of Promiscuity in Autoantigen-Specific H and L Chain Combinations as Revealed by Human H And L Chain 'Roulette'," The Journal of Immunology (1993) 150(3):880-887.
Powers et al., "Matrix Assisted Laser Desorption Ionization Imaging Mass Spectrometry Workflow for Spatial Profiling Analysis of N-linked Glycan Expression in Tissues," Anal Chem (2013) 85(20): 9799-9806.
Powers et al., "Two-Dimensional N-Glycan Distribution Mapping of Hepatocellular Carcinoma Tissues by MALDI-Imaging Mass Spectrometry," Biomolecules (2015) 5(4):2554-2572.
PROzyme InstantAB instruction manual, "Rapid N-Glycan Preparation with InstantAB" www.prozyme.com.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.

(56) References Cited

OTHER PUBLICATIONS

Ruhaak et al., "Glycan Labeling Strategies and Their Use in Identification and Quantification," Anal Bioanal Chem (2010) 397(8): 3457-3481.
Sadelain et al., "The basic principles of chimeric antigen receptor design," Cancer Discov. (2013) 3(4): 388-398.
Scarpa et al., "Characterization of recombinant helper retroviruses from Moloneybased vectors in ecotropic and amphotropic packaging cell lines," Virology (1991) 180:849-852.
Schlueter et al., "Specificity and Binding Properties of a Single-chain T Cell Receptor," J. Mol. Biol. (1996) 256: 859.
Schuler et al. "SYFPEITHI, Database for Searching and T-Cell Epitope Prediction. in Immunoinformatics," Methods in Molecular Biology, (2007) vol. 409(1): 75-93, 2007.
Sharma et al., "Efficient sleeping beauty DNA transposition from DNA minicircles," Molec Ther Nucl Acids (2013) 2:e74.
Singh et al., "ProPred: prediction of HLA-DR binding," Bioinformatics (2001) 17(12):1236-1237.
Soo Hoo et al. 'Characterization of a single-chain T-cell receptor expressed in *Escherichia coli*,' PNAS (USA) 89, 4759-4763 (1992).
Steinke et al., "The alpha gal story: Lessons learned from connecting the dots." J Allergy Clin Immunol. Mar. 2015; 135(3): 589-597.
Tamada et al., "Redirecting Gene-Modified T Cells Toward Various Cancer Types Using Tagged Antibodies," Clin Cancer Res (2012) 18(23): 6436-6445.
Tarentino et al., "Molecular Cloning and Amino Acid Sequence of peptide-N4-(N-acetyl-beta-D-glucosaminyl)asparagine Amidase From Flavobacterium Meningosepticum," J Biol Chem (1990) 265(12): 6961-6966.
Terakura et al., "Generation of CD19-chimeric antigen receptor modified CD8+ T cells derived from virus-specific central memory T cells," Blood. (2012) 119(1):72-82.
Townsend, R. R. Carbohydrate Analysis High Performance Liquid Chromatography and Capillary Electrophoresis., Ed. Z. El Rassi, pp. 181-209, 1995.
Turtle et al., "Engineered T cells for anti-cancer therapy," Curr. Opin. Immunol. (2012) 24(5): 633-639.
Urbanska et al., "A Universal Strategy for Adoptive Immunotherapy of Cancer Through Use of a Novel T-cell Antigen Receptor," Cancer Res (2012) 72(7): 1844-52.
Van Tendeloo et al., "High-level transgene expression in primary human T Tymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Wang et al., "Glycan-based diagnostic devices: current progress, challenges and perspectives." Chem Commun (Camb). (2015) 51(94): 16750-16762.
Wang et al., "Phenotypic and Functional Attributes of Lentivirus Modified CD19-specific Human CD8+ Central Memory T Cells Manufactured at Clinical Scale," J Immunother. (2012) 35(9):689-701.
Wu et al., "Adoptive T-cell therapy using autologous tumor-infiltrating lymphocytes for metastatic melanoma: current status and future outlook," Cancer (2012) 18(2): 160-175.
Wulfing et al., "Correctly Folded T-cell Receptor Fragments in the Periplasm of *Escherichia coli*," J. Mol. Biol. 242, 655 (1994).
Yang et al., "Quantitative glycome analysis of N-glycan patterns in bladder cancer vs normal bladder cells using an integrated strategy." J Proteome Res. (2015) 14(2): 639-653.
Zhang et al., "Discovery of specific metastasis-related N-glycan alterations in epithelial ovarian cancer based on quantitative glycomics." PLoS One. (2014) 9(2): e87978.
Hamouda et al., "Rapid Analysis of Cell Surface N-Glycosylation from Living Cells Using Mass Spectrometry," J Proteome Research (2014) 13(12):6144-6151.
Lauber et al., "Rapid Preparation of Released N-Glycans for HILIC Analysis Using a Labeling Reagent that Facilitates Sensitive Fluorescence and ESI-MS Detection," Analytical Chemistry (2015) 87(10):5401-5409.
Powers et al., "MALDI Imaging Mass Spectrometry Profiling of N-Glycans in Formalin-Fixed Paraffin Embedded Clinical Tissue Blocks and Tissue Microarrays," Plos One (2014) 9(9):E106255 (11 pages).
Powers et al., "Developing an Integrative Glycobiology Workflow for the Developing an Integrative Glycobiology Workflow for the Identification of Disease Markers for Pancreatic Cancer Identification of Disease Markers for Pancreatic Cancer," 2015 (284 pages).

\* cited by examiner

METHODS FOR ASSESSING CELL SURFACE GLYCOSYLATION

CROSS-REFERENCE TO RELATED APPLICATIONS

The application is a National Stage application under 35 U.S.C. § 371 of International Application No. PCT/US2018/027666, filed on Apr. 13, 2018, which claims the benefit of priority to U.S. provisional patent applications 62/485,897, filed Apr. 14, 2017, entitled "METHODS FOR ASSESSING CELL SURFACE GLYCOSYLATION" and U.S. provisional application No. 62/515,515, filed Jun. 5, 2017, entitled "METHODS FOR ASSESSING CELL SURFACE GLYCOSYLATION," the contents of each of which are incorporated by reference in their entirety.

INCORPORATION BY REFERENCE OF SEQUENCE LISTING

The present application is being filed along with a Sequence Listing in electronic format. The Sequence Listing is provided as a file entitled 735042010800SeqList.TXT, created Oct. 10, 2019, which is 37,300 bytes in size. The information in the electronic format of the Sequence Listing is incorporated by reference in its entirety.

FIELD

Provided herein are methods for assessing cell surface glycans, e.g., N-glycans, by assessing a sample of released surface glycans, and determining the presence, absence, or level of glycans present in the sample. Also provided are methods of assaying and/or evaluating a cell composition by assessing the cell surface glycan profile of the cell composition and comparing the profile to a reference sample. Methods for manufacturing and/or culturing a plurality of cell compositions having consistent surface glycan expression with low variability are also provided.

BACKGROUND

Glycans are among the principal components of a cell. Nearly all human membrane proteins, as well as numerous intracellular proteins, are co- and post-translationally modified by the covalent addition of glycans. In particular, N-glycans are post-translational modifications to proteins that can have far reaching impact to structure and function. At a cellular level, glycosylation has been implicated in cell signaling, adhesion, homing properties and other functional activities. There exists a need in the art for additional methods to measure and identify glycans, e.g., N-glycans, that are expressed on the surface of cells.

SUMMARY

Provided herein are methods for assessing cell surface glycans, the methods comprising: (a) incubating a test composition comprising a plurality of cells under conditions to release one or more glycans from the surface of cells in the test composition, wherein a sample comprising one or more cell surface glycans is generated; and (b) determining the presence, absence, identity and/or level of glycans present in the sample, thereby assessing the cell surface glycan profile of the sample.

Also provided herein are methods for assessing cell surface glycans, the methods comprising determining the presence, absence, identity and/or level of glycans present in a sample, thereby assessing the cell surface glycan profile of the sample, wherein the sample comprises one or more glycans released from the surface of cells present in a test composition comprising a plurality of cells after incubation of the test composition under conditions to release the one or more glycans.

In some embodiments of any of the provided methods, the glycans are N-glycans. In particular embodiments of any of the provided methods, cells in the test cell composition comprise whole or intact cells. In some embodiments of any of the provided methods, the cells are live cells. In certain embodiments of any of the provided methods, the test cell composition is not homogenized or sonicated prior to the incubation; and/or the test cell composition is not incubated with a protease prior to the incubation, optionally wherein the protease is trypsin; and/or the cells in the test cell composition, prior to or during the incubation, are not contacted with an agent to extract one or more cell surface or membrane proteins, optionally wherein the agent is a detergent or protease, optionally trypsin; and/or less than 10% of the cells are lysed and/or ruptured during the incubation.

In particular embodiments of any of the provided methods, the test cell composition comprises no more than $5 \times 10^6$ cells. In some embodiments of any of the provided methods, the test cell composition comprises between $1 \times 10^6$ cells and $5 \times 10^6$ cells, inclusive. In certain embodiments of any of the provided methods, the test cell composition comprises a concentration of no more than $1 \times 10^8$ cells/mL. In particular embodiments of any of the provided methods, the test cell composition comprises a concentration of between $1 \times 10^5$ cells/mL and $1 \times 10^8$ cells/mL, inclusive, between $1 \times 10^6$ cells/mL and $5 \times 10^7$ cells/mL, inclusive, or between $5 \times 10^6$ cells/mL and $2.5 \times 10^7$ cells/mL, inclusive. In some embodiments of any of the provided methods, the incubation is carried out in the presence of an N-glycosidase. In certain embodiments of any of the provided methods, the N-glycosidase is a peptide N-glycosidase (PNGase) F. In particular embodiments of any of the provided methods, the PNGase F is recombinant.

In some embodiments of any of the provided methods, the one or more glycans are one or more N-glycans, and wherein the method comprises: (i) incubating between $1 \times 10^6$ and $5 \times 10^6$ cells from the test composition with a recombinant PNGase F under conditions to release the one or more N-glycans from the surface of the cells of the test composition; (ii) labeling the one or more N-glycans with a detectable label, optionally a fluorescent label; and (iii) determining the presence, absence, or level of the labeled N-glycans, thereby assessing the cell surface glycan profile of the sample.

In certain embodiments of any of the provided methods, the test cell composition comprises about $1 \times 10^6$ to $2.5 \times 10^6$ cells. In particular embodiments of any of the provided methods, the test cell composition comprises a concentration of between $1 \times 10^6$ cells/mL and $5 \times 10^7$ cells/mL. In some embodiments of any of the provided methods, the PNGase F comprises a PGNase F of *Flavobacterium meningosepticum*, or a portion or mutant thereof that is enzymatically active. In certain embodiments of any of the provided methods, the PNGase F comprises the amino acid sequence set forth in SEQ ID NO: 1 or a portion or mutant thereof that is enzymatically active, or an amino acid sequence that exhibits at least 85%, 86%, 87%, 88%, 89%, 90%, 91%, 92%, 93%, 94%, 95%, 96%, 97%, 98%, 99% or more sequence identity to SEQ ID NO: 1 or is a portion thereof that is enzymatically active. In particular embodiments of any of the provided methods, the PNGase F comprises the amino acid sequence set forth in SEQ ID NO: 1. In some embodiments of any of the provided methods, the PNGase F comprises a tag, optionally an affinity tag. In certain embodiments of any of the provided methods, the tag is a poly-histidine (His-tag).

In particular embodiments of any of the provided methods, the PNGase F is greater than or greater than about 90%, greater than or greater than about 92%, greater than or greater than about 95%, or greater than or greater than about 98% pure; and/or the PNGase F comprises less than or less than about 10%, less than or less than about 8%, less than or less than about 5%, less than or less than about 2% non-PNGase F protein contaminants; and/or the PNGase F is greater than or greater than about 90%, greater than or greater than about 92%, greater than or greater than about 95%, or greater than or greater than about 98% homogeneous, optionally as determined by SDS-PAGE and protein staining, optionally Coomasie Blue staining.

In some embodiments of any of the provided methods, the N-glycosydase, optionally PNGase F, is in an enzymatically effective amount to release the one or more N-glycans from a native or non-denatured glycoprotein or glycoproteins and/or from the cells of the cell composition after incubation for no more than 12 hours at a temperature between 35° C. and 39° C., optionally about 37° C. In certain embodiments of any of the provided methods, the enzymatically effective amount is an amount to release the one or more N-glycans after incubation for no more than 15 minutes to 3 hours or 30 minutes to 2 hours, at a temperature between 25° C. and 39° C. or between 35° C. and 39° C., each inclusive, optionally about 37° C. In particular embodiments of any of the provided methods, the enzymatically effective amount of PNGase F releases greater than 50%, greater than 55%, greater than 60%, greater than 65%, greater than 70%, greater than 75%, greater than 80%, greater than 85%, greater than 90%, greater than 95%, greater than 99% of N-glycans present on the glycoprotein or glycoproteins and/or present on the surface of the cell composition. In some embodiments of any of the provided methods, the conditions of the incubation are sufficient to effect release of greater than 50%, greater than 55%, greater than 60%, greater than 65%, greater than 70%, greater than 75%, greater than 80%, greater than 85%, greater than 90%, greater than 95%, greater than 99% N-glycans present on the surface of the test cell composition.

In certain embodiments of any of the provided methods, the amount of N-glycosidase, optionally PNGase F, is 1 unit to 5000 units, 1 unit to 1000 units, 1 unit to 500 units, 1 unit to 250 units, 1 unit to 100 units, 1 unit to 50 units, 1 unit to 25 units, 25 units to 5000 units, 25 units to 1000 units, 25 units to 500 units, 25 units to 250 units, 25 units to 100 units, 25 units to 50 units, 50 units to 5000 units, 50 units to 1000 units, 50 units to 500 units, 50 units to 250 units, 50 units to 100 units, 100 units to 5000 units, 100 units to 1000 units, 100 units to 500 units, 100 units to 250 units, 250 units to 5000 units, 250 units to 1000 units, 250 units to 500 units, 500 units to 5000 units, 500 units to 1000 units, or 1000 units to 5000 units, each inclusive. In particular embodiments of any of the provided methods, the amount of N-glycosidase, optionally PNGase F, is greater than or greater than about or is or is about 1 unit, 5 units, 10 units, 15 units, 20 units, 25 units, 50 units, 100 units, 250 units, 500 units, 1000 units, 2500 units or 5000 units. The method of claim 27 or claim 28, wherein one unit is an amount of the N-glycosidase, optionally PNGase F, sufficient to catalyze the deglycosylation of 1 nanomole of denatured Ribonuclease B (RNase B) in 30 minutes at 37° C. In some embodiments of any of the provided methods, 500 units is an amount of the N-glycosidase, optionally PNGase F, sufficient to catalyze the deglycosylation of 10 µg of Ribonuclease B (RNase B) incubated in 1×PBS for 5-10 minutes at 37° C. or room temperature.

In certain embodiments of any of the provided methods, the incubating the test composition is for an amount of time that between or between about 5 minutes and 12 hours, 30 minutes and 6 hours or 1 hour and 3 hours, each inclusive. In particular embodiments of any of the provided methods, the incubating the test composition is for at least or at least about or is or is about 5 minutes, about 10 minutes, about 15 minutes, 30 minutes, 1 hour, 2 hours 3 hours, 4 hours, 5 hours or 6 hours. In some embodiments of any of the provided methods, the incubating the test composition is for about 30 minutes. In certain embodiments of any of the provided methods, the incubating the test composition is at a temperature between 25° C. and 39° C. or between 35° C. and 39° C. In particular embodiments of any of the provided methods, the incubating the test composition is at a temperature of about 37° C. In some embodiments of any of the provided methods, the incubating the test composition is for about 30 minutes at a temperature of about 37° C.

In certain embodiments of any of the provided methods, prior to the determining the presence, absence, identity and/or level of glycans present in a sample, the method further comprises labeling glycans from the sample with a detectable label, optionally a fluorescent label. In particular embodiments of any of the provided methods, the label is a fluorescent label and the fluorescent label is or comprises 2-aminobenzamide (2-AB), 2-aminobenzoic acid (2-AA), 2-aminopyridine (PA), 2-Aminoacridone (AMAC), 2-aminonaphthalene trisulfonic acid (ANTS), and 1-aminopyrene-3,6,8-trisulfonic acid (APTS), 3-(Acetylamino)-6-aminoacridin (AA-Ac), 6-Aminoquinoline (6-AQ), 7-Aminomethyl-coumarin (AMC), 2-Amino (6-amido-biotinyl) pyridine (BAP), 9-Fluorenylmethoxycarbonyl (FMOC)-hydrazide, 1,2-Diamino-4,5-methylenedioxy-benzene (DMB), or o-Phenylenediamine (OPD). In some embodiments of any of the provided methods, the fluorescent label comprises a quinolinyl fluorophore. In certain embodiments of any of the provided methods, the fluorescent label comprises a carbamate tagging group. In particular embodiments of any of the provided methods, the fluorescent label comprises a basic tertiary amine. In some embodiments of any of the provided methods, the fluorescent label comprises a carbamate tagging group, a quinolone fluorophore, and a tertiary amine.

In certain embodiments of any of the provided methods, prior to determining the presence, absence, identity and/or level of the one or more glycans, the sample is subjected to glycan purification or enrichment. In particular embodiments of any of the provided methods, glycan purification or enrichment is carried out by solid phase extraction (SPE).

In some embodiments of any of the provided methods, determining the presence, absence, or level of the one or more glycans comprises subjecting the sample to mass spectrometry. In certain embodiments of any of the provided methods, the mass spectrometry is electrospray ionization mass spectrometry (ESI-MS), turbospray ionization mass spectrometry, nanospray ionization mass spectrometry, thermospray ionization mass spectrometry, sonic spray ionization mass spectrometry, surface enhanced laser desorption ionization mass spectrometry (SELDI-MS) and matrix assisted laser desorption/ionization mass spectrometry (MALDI-MS). In particular embodiments of any of the provided methods, the mass spectrometry is MALDI-MS.

In some embodiments of any of the provided methods, determining the presence, absence, or level of glycans comprises subjecting the sample to liquid chromatography (LC) followed by mass spectrometry. In certain embodiments of any of the provided methods, the liquid chromatography is high performance liquid chromatography (HPLC), ultra high performance liquid chromatography (UHPLC), or ultra performance liquid chromatography (UPLC). In particular embodiments of any of the provided methods, the liquid chromatography is ultra performance liquid chromatography (UPLC). In some embodiments of any of the provided methods, the liquid chromatography and mass spectrometry are carried out online. In certain embodiments of any of the provided methods, the liquid chromatography is selected from normal phase (NP-), reverse phase (RP) and hydrophilic interaction chromatography (HILIC). In particular embodiments of any of the provided methods, the liquid chromatography is hydrophilic interaction chromatography (HILIC).

In some embodiments of any of the provided methods, the mass spectrometry comprises electrospray ionization mass spectrometry (ESI-MS), turbospray ionization mass spectrometry, nanospray ionization mass spectrometry, thermospray ionization mass spectrometry or sonic spray ionization mass spectrometry. In some embodiments of any of the provided methods, the mass spectrometry comprises ESI-MS. In particular embodiments of any of the provided methods, the mass spectrometry comprises tandem mass spectrometry (MS/MS). In certain embodiments of any of the provided methods, the mass spectrometry comprises tandem ESI mass spectrometry (ESI-MS/MS).

In certain embodiments of any of the provided methods, the mass spectrometer that performs the mass spectrometry comprises one or more of a quadrupole, ion trap, time of flight (TOF), or Fourier transform ion cyclotron resonance mass analyzer. In particular embodiments of any of the provided methods, the mass spectrometer comprises an ion trap mass analyzer that is a three-dimensional quadrupole ion trap, a cylindrical ion trap, a linear quadrupole ion trap, or an Orbitrap mass analyzer. In some embodiments of any of the provided methods, the mass spectrometer is a quadrupole-Orbitrap mass spectrometer.

In certain embodiments of any of the provided methods, the determining the presence, absence, identity and/or level of the one or more glycans comprises analyzing one or more glycan structure or structures for branching, linkages between monosaccharides and/or location of monosaccharides. In particular embodiments of any of the provided methods, the one or more glycans comprises high mannose N-glycans, bisected and Sialyl Lewisx N-glycans, and/or N-acetyl lactosamine containing N-glycans. In some embodiments of any of the provided methods, the one or more glycans comprises a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

In certain embodiments of any of the provided methods, the determining the presence, absence, or level of glycans present in the sample comprises determining the presence, absence, or level of at least 25, at least 50, at least 60, at least 70, at least 80, at least 90, at least 100, or at least 200 different species of glycans. In particular embodiments of any of the provided methods, the presence or level of a glycan species present in the sample is determined if at least 100 amol, at least 500 amol, at least 1 fmol, at least 5 fmol, or at least 10 fmol of the glycan species is present in the sample. In some embodiments of any of the provided methods, the presence or level of a glycan species present in the sample is determined if glycan species makes up at least 0.00001%, 0.00005%, 0.0001%, 0.0005%, 0.001%, 0.005%, or 0.01% of the total glycans in the sample. In certain embodiments of any of the provided methods, the species of glycans are species of N-glycans.

In particular embodiments of any of the provided methods, the test cell composition is or comprises at least a portion of a source cell composition comprising the plurality of cells. In some embodiments of any of the provided methods, the cells comprise mammalian cells or the test cell composition comprises mammalian cells. In certain embodiments of any of the provided methods, the cells comprise human cells or the test cell composition comprises human cells. In particular embodiments of any of the provided methods, the cells comprise stem cells or the test cell composition comprises stem cells. In some embodiments of any of the provided methods, the stem cell is an induced pluripotent stem cell (iPSC). In certain embodiments of any of the provided methods, the test cell composition comprises cells present in an apheresis product or a leukapheresis product or cells derived therefrom. In particular embodiments of any of the provided methods, the cells comprise immune cells, white blood cells, peripheral blood mononuclear cells (PBMC), lymphocytes, or unfractionated T cells; or the test cell composition comprises immune cells, white blood cells, peripheral blood mononuclear cells (PBMC), lymphocytes, or unfractionated T cells. In some embodiments of any of the provided methods, the cells comprise an immune cell or the test cell composition comprises immune cells. In certain embodiments of any of the provided methods, the immune cell is a T cell, B cell, macrophage, neutrophil, natural killer (NK) cell or dendritic cell. In particular embodiments of any of the provided methods, the cells comprise T cells that are CD4+ and/or CD8+ T cells or the test cell composition comprises T cells that are CD4+ and/or CD8+ T cells.

In some embodiments of any of the provided methods, the test cell composition comprises: cells isolated from a biological sample by immunoaffinity-based methods; and/or cells transduced with a viral vector encoding a recombinant protein; and/or cell incubated in the presence of one or more test agents, optionally one more peptide, protein, polypeptide, nucleic acid, small molecule; and/or cells activated and/or expanded in the presence of one or more stimulating conditions; and/or cryopreserved cells and/or cells comprising a cryoprotectant; and/or cells formulated for administration to a subject, optionally in the presence of a pharmaceutically acceptable excipient.

In certain embodiments of any of the provided methods, the test agent is a candidate for modulating the growth, proliferation, viability, differentiation, intracellular signaling, activation and/or expansion of one or more cells in the test cell composition. In particular embodiments of any of the provided methods, the stimulating condition comprises incubation with a stimulatory reagent capable of activating one or more intracellular signaling domains of one or more components of a TCR complex and/or one or more intracellular signaling domains of one or more costimulatory molecules. In some embodiments of any of the provided methods, the stimulatory reagent comprises a primary agent that specifically binds to a member of a TCR complex and a secondary agent that specifically binds to a T cell costimulatory molecule. In certain embodiments of any of the provided methods, the primary agent specifically binds to CD3 and/or the costimulatory molecule is selected from the group consisting of CD28, CD137 (4-1-BB), OX40, or ICOS. In particular embodiments of any of the provided methods, stimulatory reagent comprises an anti-CD3 antibody or antigen binding fragment thereof and an anti-CD28 antibody or an antigen-binding fragment thereto. In some embodiments of any of the provided methods, the primary and secondary agents comprise antibodies and/or are present on the surface of a solid support. In certain embodiments of any of the provided methods, the solid support is or comprises a bead.

In particular embodiments of any of the provided methods, the cells express a recombinant receptor or the test composition comprises cells expressing a recombinant receptor. In certain embodiments of any of the provided methods, the recombinant receptor is or comprises a chimeric receptor and/or a recombinant antigen receptor. In some embodiments of any of the provided methods, the recombinant receptor is capable of binding to a target antigen that is associated with, specific to, and/or expressed on a cell or tissue of a disease, disorder or condition. In particular embodiments of any of the provided methods, the disease, disorder or condition is an infectious disease or disorder, an autoimmune disease, an inflammatory disease, or a tumor or a cancer. In certain embodiments of any of the provided methods, the target antigen is a tumor antigen.

In some embodiments of any of the provided methods, the target antigen is selected from among ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRLS, FCRHS, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag. In particular embodiments of any of the provided methods, the recombinant receptor is or comprises a functional non-TCR antigen receptor or a TCR or antigen-binding fragment thereof. In certain embodiments of any of the provided methods, the recombinant receptor is a chimeric antigen receptor (CAR).

In certain embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

Provided herein are methods of assaying a cell composition, the methods comprising: (a) assessing the cell surface glycan profile in a sample from a test cell composition comprising a plurality of cells according to the methods provided herein; and (b) comparing the cell surface glycan profile of the sample to the cell surface glycan profile of a reference sample. Provided herein are methods of assaying a cell composition, the methods comprising comparing the cell surface glycan profile of a sample compared to the cell surface profile of a reference sample, wherein cell surface glycan profile of the sample is or has been determined according to the method of any of the methods provided herein from a test cell composition comprising a plurality of cells.

In certain embodiments of any of the provided methods, the cell surface glycan profile comprises at least 25, at least 50, at least 60, at least 70, at least 80, at least 90, at least 100, or at least 200 different species of glycans, optionally different species of N-glycans. In particular embodiments of any of the provided methods, the cell surface glycan profile comprises high mannose N-glycans, bisected and Sialyl Lewis$^X$ N-glycans, and/or N-acetyl lactosamine containing N-glycans. In some embodiments of any of the provided methods, the cell surface glycan profile comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

In certain embodiments of any of the provided methods, the cell surface glycan profile comprises the glycans in Table E1 or a subset thereof. In particular embodiments of any of the provided methods, the reference sample is a reference standard comprising a release specification, a label requirement or a compendia specification. In some embodiments of any of the provided methods, the cell composition is released for treatment of a subject only if the cell surface glycan profile of the composition is substantially the same as the reference sample and/or if the percent of a target glycan or each of a plurality of target glycans to the total glycans present in the sample differs by no more than 25%, no more than 20% or no more than 10% from the percent of the target glycan or each of the plurality of target glycans to the total glycans present in the reference sample. In certain embodiments of any of the provided methods, the target glycans comprise at least 25, at least 50, at least 60, at least 70, at least 80, at least 90, at least 100, or at least 200 different species of glycans.

In particular embodiments of any of the provided methods, the target glycan or glycans comprise high mannose N-glycans, bisected and Sialyl Lewis$^X$ N-glycans, and/or N-acetyl lactosamine containing N-glycans. In some embodiments of any of the provided methods, the target glycan or glycans comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues. In certain embodiments of any of the provided methods, the target glycan or glycans comprise the glycans present in Table E1 or a subset thereof. In particular embodiments of any of the provided methods, the target glycan or glycans comprise the glycans detectable in the cell surface glycan profile. In some embodiments of any of the provided methods, the reference sample is a cell surface glycan profile from a different cell composition.

In certain embodiments of any of the provided methods, the different cell composition is from a different stage of a manufacturing process for producing the test cell composition or a source cell composition from which the test composition has been derived or obtained, wherein the stage of the manufacturing process optionally is a prior stage of the manufacturing process. In particular embodiments of any of the provided methods, the manufacturing process comprises one or more stages selected from: cells isolated from a biological sample by leukapheresis or apheresis; cells selected from a biological sample by immunoaffinity-based methods; and/or cells introduced with a recombinant nucleic acid, optionally a viral vector encoding a recombinant protein; and/or cell incubated in the presence of one or more test agents, optionally one more peptide, protein, polypeptide, nucleic acid, small molecule; and/or cells activated and/or expanded in the presence of one or more stimulating conditions; and/or cryopreservation of cells in the presence of a cryoprotectant; and/or cells formulated for administration to a subject, optionally in the presence of a pharmaceutically acceptable excipient.

In some embodiments of any of the provided methods, a difference in the glycan profile between the test composition and reference sample indicates one or more differences is present in the cells among the cells produced at the different stages in the manufacturing process. In certain embodiments of any of the provided methods, the difference in the glycan profile exists if the cell surface glycan profile of the composition is substantially different from the reference sample and/or if the percent of a target glycan or each of the one or more target glycans to the total glycans present in the sample differs by greater than or greater than about 10%, 20%, 30%, 40%, 50%, 60%, 70%, 80%, 90% or more from the percent of the target glycan or each of the one or more target glycans to the total glycans present in the reference sample. In particular embodiments of any of the provided methods, the target glycans comprise at least 25, at least 50, at least 60, at least 70, at least 80, at least 90, at least 100, or at least 200 different species of glycans, optionally wherein the species of glycans are N-glycans.

In some embodiments of any of the provided methods, the target glycan or glycans comprise high mannose N-glycans, bisected and Sialyl Lewis' N-glycans, and/or N-acetyl lactosamine containing N-glycans. In certain embodiments of any of the provided methods, the target glycan or glycans comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues. In particular embodiments of any of the provided methods, the target glycan or glycans comprise the glycans present in Table E1 or a subset thereof. In some embodiments of any of the provided methods, the target glycan or glycans comprise the glycans detectable in the cell surface glycan profile.

In certain embodiments of any of the provided methods, the one more differences is associated with a functional activity or phenotype of the cells. In particular embodiments of any of the provided methods, the functional activity or phenotype comprises one or more of masking of a cell surface marker, a metabolic activity, differentiation state, proliferative or expansion capacity, activation state, cytolytic activity, signaling activity, an adhesion property, or a homing property. Some embodiments of any of the provided methods further comprise modulating or changing the process for manufacturing the cell composition. In certain embodiments of any of the provided methods, the reference standard comprises an average or median of the presence, absence, identity and/or level of the one or more target glycan or glycans among a plurality of compositions produced by the process.

Provided herein are methods for manufacturing a cell composition, comprising incubating and/or contacting an input composition comprising a plurality of cells with one or more agents and/or under one or more conditions thereby generating the cell composition, wherein the cell composition comprises one or a plurality of cells that are genetically, phenotypically, and/or functionally different from one or a plurality of cells from the input composition, and wherein the cell composition comprises one or a plurality of cells that comprise a cell surface glycan profile comprising one or more target glycans and/or each of the one or more target glycans in the cell surface glycan profile differs by no more than 25% from the cell surface glycan profile or each of the one or more target glycans to the total glycans present in a reference sample, wherein the cell surface glycan profile comprises glycans released from the surface of cells in the cell composition. In some embodiments of any of the provided methods, the cell surface glycan profile or the one or more target glycans is determined according to any of the methods provided herein.

In certain embodiments of any of the provided methods, the cell composition comprises cells comprising a recombinant nucleic acid. In particular embodiments of any of the provided methods, prior to, during, or subsequent to the incubation and/or contacting, the method comprises one or more steps selected from cell washing, dilution, isolation, selection, separation, cultivation, stimulation, introduction of a recombinant nucleic acid, cryopreservation, formulation and/or packaging. In some embodiments of any of the provided methods, prior to, during, or subsequent to incubation and/or contacting, the method comprises one or more steps selected from: cells isolated from a biological sample by leukapheresis or apheresis; cells selected from a biological sample by immunoaffinity-based methods; and/or cells introduced with a recombinant nucleic acid, optionally a viral vector encoding a recombinant protein; and/or cell incubated in the presence of one or more agent, optionally one more peptide, protein, polypeptide, nucleic acid, small molecule; and/or cells activated and/or expanded in the presence of one or more stimulating conditions; and/or cryopreservation of cells in the presence of a cryoprotectant; and/or cells formulated for administration to a subject, optionally in the presence of a pharmaceutically acceptable excipient.

In certain embodiments of any of the provided methods, he one or more test agents or conditions comprises presence or concentration of serum; time in culture; presence or amount of a stimulating agent; the type or extent of a stimulating agent; presence or amount of amino acids; temperature; the source or cell types of the source composition; the ratio or percentage of cell types in the source composition, optionally the CD4+/CD8+ T cell ratio; the presence or amount of beads; cell density; static culture; rocking culture; perfusion; the type of viral vector; the vector copy number; the presence of a transduction adjuvant; cell density of the source composition in cryopreservation; the extent of expression of the recombinant receptor; or the presence of a compound to modulate cell phenotype.

In particular embodiments of any of the provided methods, the one or more test agents or conditions comprises stimulating conditions, a peptide, a protein, a polypeptide, a nucleic acid, a small molecule, and/or a recombinant nucleic acid, optionally a viral vector encoding a recombinant protein. In some embodiments of any of the provided methods, the agent modulates the growth, proliferation, viability, differentiation, intracellular signaling, activation and/or expansion of one or more cells in the cell composition.

In certain embodiments of any of the provided methods, the stimulating condition comprises incubation with a stimulatory agent capable of activating one or more intracellular signaling domains of one or more components of a TCR complex and/or one or more intracellular signaling domains of one or more costimulatory molecules. In particular embodiments of any of the provided methods, the stimulatory agent comprises a primary agent that specifically binds to a member of a TCR complex and a secondary agent that specifically binds to a T cell costimulatory molecule. In some embodiments of any of the provided methods, the primary agent specifically binds to CD3 and/or the costimulatory molecule is selected from the group consisting of CD28, CD137 (4-1-BB), OX40, or ICOS.

In certain embodiments of any of the provided methods, stimulatory agent comprises an anti-CD3 antibody or antigen binding fragment thereof and/or an anti-CD28 antibody or an antigen-binding fragment thereto. In particular embodiments of any of the provided methods, the primary and secondary agents comprise antibodies and/or are present on the surface of a solid support. In some embodiments of any of the provided methods, the solid support is or comprises a bead. In certain embodiments of any of the provided methods, the stimulating conditions comprises the presence of one or more cytokines, optionally IL-2, IL-15 and/or IL-7.

In particular embodiments of any of the provided methods, the reference sample is a reference standard comprising a release specification, a label requirement or a compendia specification. In some embodiments of any of the provided methods, the reference sample comprises an average or median of the presence, absence, identity and/or level of the one or more target glycan or glycans among a plurality of compositions produced by the incubating and/or the contacting the source composition with the one or more agents and/or under the one or more conditions. In certain embodiments of any of the provided methods, the cell surface glycan profile comprising the one or more target glycans or each of the one or more target glycans differs by no more than or about 20%, no more than or about 15%, no more than or about 10% or no more than or about 5% from the cell surface glycan profile or each of the one or more target glycans to the total glycans present in the reference sample. In particular embodiments of any of the provided methods, the target glycans comprise at least 25, at least 50, at least 60, at least 70, at least 80, at least 90, at least 100, or at least 200 different species of glycans, optionally wherein the species of glycans are N-glycans.

In some embodiments of any of the provided methods, the target glycan or glycans comprise high mannose N-glycans, bisected and Sialyl Lewis$^x$ N-glycans, and/or N-acetyl lactosamine containing N-glycans. In certain embodiments of any of the provided methods, the target glycan or glycans comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues. In particular embodiments of any of the provided methods, the target glycan or glycans comprise the glycans present in Table E1 or a subset thereof. In some embodiments of any of the provided methods, the target glycan or glycans comprise the glycans detectable in the cell surface glycan profile.

Provided herein are methods for screening one or more test agents or conditions on a cell composition, comprising: (a) assessing a cell surface glycan profile in a sample from a test cell composition, wherein the test cell composition is or is derived from an source composition that has been incubated or treated in the presence of one or more test agents or conditions; and (b) comparing the cell surface glycan profile of the sample to the cell surface glycan profile of a reference sample, the reference sample comprising one or more target glycans.

Also provided herein are methods for screening one or more test agents or conditions on a cell composition, comprising comparing the cell surface glycan profile of a sample compared to the cell surface glycan profile of a reference sample, wherein the sample is from a test cell composition that is or is derived from an source composition that has been incubated or treated in the presence of one or more test agents or conditions. In certain embodiments of any of the provided methods, the cell surface glycan profile comprises the presence, absence, identity and/or level of one or more glycans in the sample. In particular embodiments of any of the provided methods, the cell surface glycan profile is determined according to the method of any of the methods provided herein.

In some embodiments of any of the provided methods, the reference sample is derived from a composition incubated or treated under the same or substantially the same conditions as the test cell composition or source composition except in the absence of treating in the presence of the one or more test agents or conditions or in the presence of one or more alternative test agents or conditions. In certain embodiments of any of the provided methods, the reference sample comprises an average or median of the presence, absence, identity and/or level of the one or more target glycan or glycans among a plurality of compositions incubated or treated in the presence of the one or more test agents or conditions. In particular embodiments of any of the provided methods, the one or more test agents or conditions comprises presence or concentration of serum; time in culture; presence or amount of a stimulating agent; the type or extent of a stimulating agent; presence or amount of amino acids; temperature; the source or cell types of the source composition; the ratio or percentage of cell types in the source composition, optionally the CD4+/CD8+ T cell ratio; the presence or amount of beads; cell density; static culture; rocking culture; perfusion; the type of viral vector; the vector copy number; the presence of a transduction adjuvant; cell density of the source composition in cryopreservation; the extent of expression of the recombinant receptor; or the presence of a compound to modulate cell phenotype.

In some embodiments of any of the provided methods, the one or more test agents or conditions comprises one or more compounds from a library of test compounds. In certain embodiments of any of the provided methods, the target glycans comprise at least 25, at least 50, at least 60, at least 70, at least 80, at least 90, at least 100, or at least 200 different species of glycans, optionally wherein the species of glycans are N-glycans. In particular embodiments of any of the provided methods, the target glycan or glycans comprise high mannose N-glycans, bisected and Sialyl Lewis' N-glycans, and/or N-acetyl lactosamine containing N-glycans.

In some embodiments of any of the provided methods, the target glycan or glycans comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues. In certain embodiments of any of the provided methods, the target glycan or glycans comprise the glycans present in Table E1 or a subset thereof. In particular embodiments of any of the provided methods, the target glycan or glycans comprise the glycans detectable in the cell surface glycan profile.

In some embodiments of any of the provided methods, the method comprises selecting the one or more test agent or conditions for incubating or treating the cells if the comparison indicates the cell surface glycan profile of the sample or each of the one or more target glycans is substantially the same as the reference sample and/or if the comparison indicates the cell surface glycan profile comprising the one or more target glycans or each of the one or more target glycans differs by no more than or about 20%, no more than or about 15%, no more than or about 10% or no more than or about 5% from the cell surface glycan profile or each of the one or more target glycans to the total glycans present in the reference sample. In certain embodiments of any of the provided methods, the methods comprise repeating the method with one or more further test agent or condition if the comparison indicates the cell surface glycan profile of the sample or each of the one or more target glycans is substantially different from the reference sample and/or if the comparison indicate the cell surface glycan profile comprising the one or more target glycans or each of the one or more target glycans differs by greater than or greater than about 10%, 20%, 30%, 40%, 50%, 60%, 70%, 80%, 90% or more from the cell surface glycan profile or each of the one or more target glycans to the total glycans present in the reference sample.

In particular embodiments of any of the provided methods, the test agent is a candidate for modulating the growth, proliferation, viability, differentiation, activation and/or expansion, of one or more cells in the test cell composition. In certain embodiments of any of the provided methods, the test cell composition comprises cells comprising a recombinant nucleic acid. In some embodiments of any of the provided methods, the recombinant nucleic acid encodes a recombinant protein, optionally a recombinant receptor. In particular embodiments of any of the provided methods, the recombinant receptor is or comprises a chimeric receptor and/or a recombinant antigen receptor.

In certain embodiments of any of the provided methods, the recombinant receptor is capable of binding to a target antigen that is associated with, specific to, and/or expressed on a cell or tissue of a disease, disorder or condition. In some embodiments of any of the provided methods, the disease, disorder or condition is an infectious disease or disorder, an autoimmune disease, an inflammatory disease, or a tumor or a cancer. In particular embodiments of any of the provided methods, the target antigen is a tumor antigen. In certain embodiments of any of the provided methods, the target antigen is selected from among ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRLS, FCRHS, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag. In some embodiments of any of the provided methods, the recombinant receptor is or comprises a functional non-TCR antigen receptor or a TCR or antigen-binding fragment thereof. In certain embodiments of any of the provided methods, the recombinant receptor is a chimeric antigen receptor (CAR).

In particular embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In particular embodiments of any of the provided methods, the cells comprise mammalian cells or the test cell composition comprises mammalian cells. In some embodiments of any of the provided methods, the cells comprise human cells or the test cell composition comprises human cells. In certain embodiments of any of the provided methods, the cells comprise stem cells or the test cell composition comprises stem cells. In particular embodiments of any of the provided methods, the stem cell is an induced pluripotent stem cell (iPSC). In some embodiments of any of the provided methods, the composition or test cell composition comprises cells present in an apheresis product or a leukapheresis product or cells derived therefrom.

In certain embodiments of any of the provided methods: the cells comprise immune cells, white blood cells, peripheral blood mononuclear cells (PBMC), lymphocytes, or unfractionated T cells; or the test cell composition comprises immune cells, white blood cells, peripheral blood mononuclear cells (PBMC), lymphocytes, or unfractionated T cells. In particular embodiments of any of the provided methods, the cells comprise an immune cell or the test cell composition comprises immune cells. In some embodiments of any of the provided methods, the immune cell is a T cell, B cell, macrophage, neutrophil, natural killer (NK) cell or dendritic cell. In certain embodiments of any of the provided methods, the cells comprise T cells that are CD4+ and/or CD8+ T cells or the test cell composition comprises T cells that are CD4+ and/or CD8+ T cells. In particular embodiments of any of the provided methods, the cells are primary cells.

Particular embodiments provide a method of detecting a presence, absence, identity, and/or level of one or more substances in a cell composition, the method comprising: (a) assessing the cell surface glycan profile in a sample from a test cell composition comprising a plurality of cells according to any of the methods provided herein, wherein the plurality of cells are from or are derived from a cell type; and (b) identifying one or more non-native glycans in the cell surface glycan profile that are not synthesized and/or expressed by cells of the cell type. In certain embodiments, the cell type is human. In some embodiments, the cell type is an immune cell. In particular embodiments, the cell type is a T cell.

In certain embodiments, the test cell composition was produced by culturing and/or incubating the plurality of cells in the presence of a substance, in which comprises at least one protein comprising one or more non-native glycans. In some embodiments, the at least one protein is an albumin, a growth factor, a cytokine, a chemokine, an insulin or insulin-like peptide, a transferrin, or a superoxide dismutase. In particular embodiments, the at least one protein is a recombinant protein. In certain embodiments, the one or more non-native glycans and/or the at least one protein are present in a serum. In some embodiments, the serum is fetal bovine serum (FBS), bovine calf serum (BCS), newborn calf serum (NBCS), horse serum, goat serum, lamb serum, donkey serum, or porcine serum.

In particular embodiments, the one or more non-native glycans and/or the at least one protein are (i) not produced by and/or (ii) not expressed on the surface of cells from the same order, family, genus, or species as the cells of the plurality. In certain embodiments, the one or more non-native glycans comprise a non-human glycan. In some embodiments, the identifying the one or more non-native glycan comprises comparing the surface glycan profile to a reference glycan profile, wherein the reference sample is a glycan profile from a source containing the one or more non-native glycans. In particular embodiments, the reference glycan profile is generated from a reference sample comprising a substance, that has not been contacted, incubated, and/or exposed to the cells of the plurality. In some embodiments, the reference glycan profile is generated from a reference sample comprising a media, a serum, or a component thereof, or from a protein or recombinant protein thereof, that has not been contacted, incubated and/or exposed to the cells of the plurality.

BRIEF DESCRIPTION OF THE DRAWINGS

FIG. 1A depicts an overview of an exemplary method for mapping cell surface N-glycans. In the method, a composition containing whole, intact cells is incubated with PNGaseF to release N-glycans. The cells are removed and the sample is subjected to solid phase extraction (SPE), followed by separation of glycans using hydrophilic interaction chromatography (HILIC) liquid chromatography (LC) and detection by fluorescence (Waters ACQUITY I-Class) and positive electrospray ionization (ESI) mass spectrometry (MS), Q-Exactive™ HF (Thermo Scientific)) for relative quantification and identification. FIG. 1B shows a comparison of methods for traditional targeted analysis by immunoaffinity and flow cytometry (Targeted) with the exemplary method provided herein (unbiased).

FIG. 2 depicts an annotated chromatogram of N-glycans separated using HILIC liquid chromatography and detected by fluorescence (HILIC-FLR).

FIG. 3A shows an HILIC-FLR of PNGase F released N-glycans from a composition containing CD4+/CD8+ T cells expressing an anti-CD19 CAR. FIG. 3B shows a total ion chromatogram (TIC) from the same cell composition as FIG. 3A.

FIG. 4A shows a HILIC-FLR chromatogram of PNGase F released N-glycans from the activated CD3+ T cell composition. FIG. 4B shows an extracted ion chromatogram (XIC) produced from the first stage of the tandem MS for the exemplary N-glycan, A3S3F (theoretical mass of 1113.0933), in the +3 charged state using a 5 ppm mass tolerance. FIG. 4C shows the MS/MS fragmentation of a further exemplary N-glycan, A3S4F (theoretical mass of 1210.4614), produced by the second stage of the tandem MS. Dashed boxes in FIG. 4C indicate different n-acetyl glucosamine residue linkages.

FIG. 5A shown an overlay of high mannose N-glycans in samples from CD4+ and CD8+ T cell compositions. On both the CD4+ and CD8+ overlays, where the X-axis is marked with an arrow, the top line displays the N-glycan profile of the cryopreserved drug product, the middle line displays the N-glycan profile of the cells that were activated and transduced, and the bottom line shows the N-glycan profile of the cells obtained from immunoaffinity-based selection.

FIG. 5B shows an overlay of bisected N-glycans in samples from CD4+ and CD8+ T cell compositions. On both the CD4+ and CD8+ overlays, where the X-axis is marked with an arrow, the top line displays the N-glycan profile of the cryopreserved drug product, the middle line) displays the N-glycan profile of the cells that were activated and transduced, and the bottom line shows the N-glycan profile of the cells obtained from immunoaffinity-based selection. FIG. 5C shows an overlay of polylactosamine N-glycans in samples from CD4+ and CD8+ T cell compositions. On both the CD4+ and CD8+ overlays, where the X-axis is marked with an arrow, the top line shows the N-glycan profile of the cells obtained from immunoaffinity-based selection, the middle line displays the N-glycan profile of the cryopreserved drug product, and the bottom line displays the N-glycan profile of the cells that were activated and transduced.

FIG. 10 shows surface N-glycan profiles visualized by fluorescence detection and mass spectrometry from three exemplary different anti-CD19 CAR-expressing CD4+ T cell compositions that were generated by substantially the same process, but that differed in two conditions involved in cultivating the cells. Arrows indicate a peak associated with a bisected N-glycan.

DETAILED DESCRIPTION

Figure 1A:
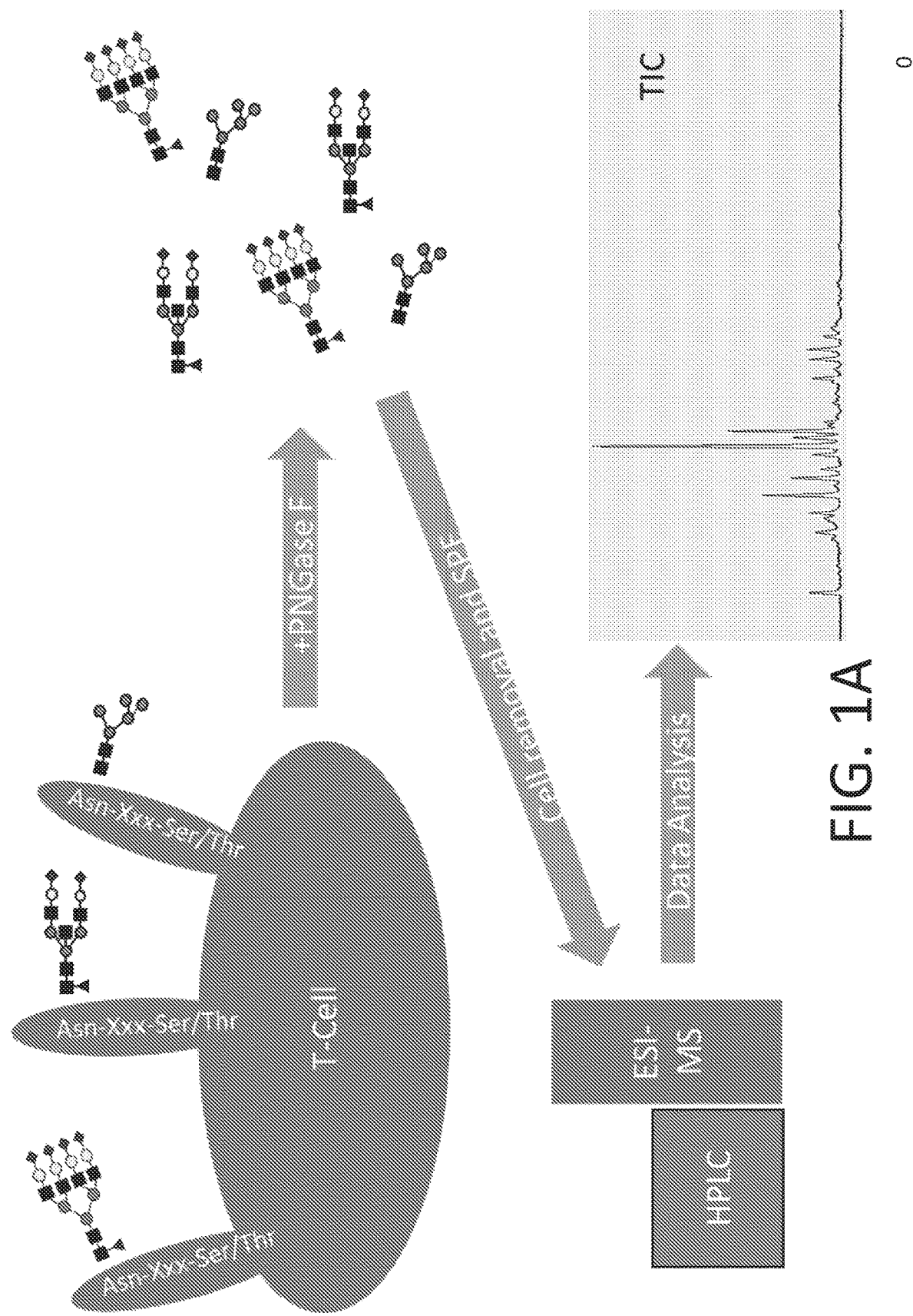
FIGS. 1A and 1B depict exemplary methods for generating surface N-glcyan profiles.

Provided herein are methods for assessing glycans that are expressed and/or exposed on the cell surface, i.e., surface glycans, by determining the presence, absence, or level of glycans present in a sample containing glycans that are or have been released from the surface of cells in a composition. In some embodiments, the provided methods include one or more steps for releasing glycans, e.g., N-glycans, from the surface of cells in the composition. In certain embodiments, the methods provided herein provide steps for detecting glycans that have been released from the cell surface by one or more suitable techniques, for example one or more of liquid chromatography and mass spectrometry. In some embodiments, the methods provided herein allow for a highly sensitive and accurate assessment or analysis of the surface glycan expression profile of the cell composition.

In particular embodiments, surface glycans of a population or composition of cells can be assessed and/or analyzed by the methods provided herein. In certain embodiments, the methods provide steps for incubating the cells under conditions suitable for releasing glycans from the surface of cells. In certain embodiments, the conditions include contacting, treating, and/or incubating the cells with an agent that promotes and/or catalyzes the release of glycans from the surface of the cells, for example by removing intact glycans from proteins or other moieties that are present, expressed, and/or exposed at the cell surface. In certain embodiments, the methods provided herein also include steps for derivatizing and/or labeling glycans to enhance or increase sensitivity and/or accuracy for identification, measurement, and/or detection of the glycans. In particular embodiments, the provided methods include steps for detecting the glycans, e.g., labeled glycans, through combined techniques of liquid chromatography and mass spectrometry, allowing for highly accurate and sensitive measurements of the presence, identity, and levels of individual glycans present in the sample of released surface glycans.

Also provided herein are methods of assaying a cell composition by assessing the cell surface glycan profile of the cell composition and comparing it to a reference sample. For example, in some embodiments, a cell composition, e.g., a therapeutic cell composition, may have a distinct profile of glycan expression with respect to the level of surface expression of distinct glycan species, types of glycans, and/or glycan families as compared to compositions of different cells. Thus, in some embodiments, a reference standard may be generated by assessing a plurality of cell compositions. Such a reference standard may be used, in some embodiments, as a quality control and/or for a release assay, or to monitor or control the manufacture or culture of the cell compositions.

In addition, provided herein are methods for generating a plurality of cell compositions, e.g., therapeutic cell compositions and/or compositions containing engineered cells, with low variability with respect to surface glycan expression. In some embodiments, the level and/or expression of distinct glycan species, types of glycans, and/or glycan families at the cell surface may contribute or at least correlate to different aspects of cell physiology or function. Thus, in some embodiments, it is desirable to produce cell compositions with a high degree of similarity with respect to surface glycan expression.

Figure 1B:
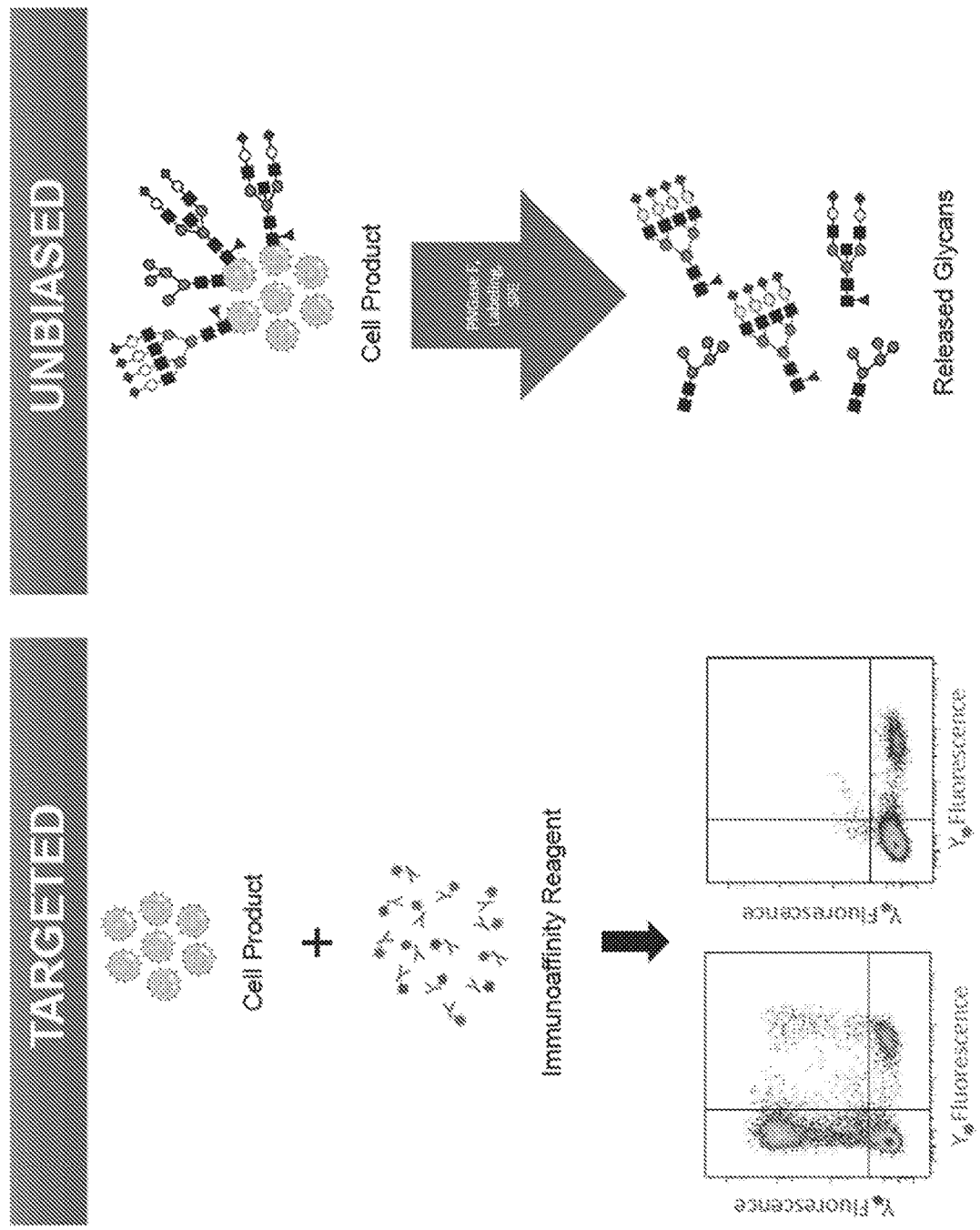

Particular embodiments contemplate that cell therapies, and in particular adoptive T-Cell therapies, represent a powerful technology for the treatment, alleviation, and/or amelioration of various diseases, such as cancer. Current analytical tools available for assessing therapeutic or pharmaceutical cell compositions include examination of cell surface or internal markers via flow cytometry. In some embodiments, the methods provided herein complement and/or enhance current methods for evaluating cell compositions, which represent methods and techniques to reliably evaluate characteristics of therapeutic or pharmaceutical cell compositions as well as cells at different stages of a manufacturing or development process. In particular embodiments, provided herein are unbiased methods useful for releasing cell surface N-linked glycans and for detecting, identifying, and/or quantifying one or more individual N-glycan species (such, for example, methods exemplified by FIGS. 1A-1B).

In certain embodiments, the methods provided herein provide information regarding the presence, absence, identities, relative amounts, and levels of individual glycan species that are expressed on a cell surface. In some embodiments, the methods provided herein are suitable for generating a glycan expression profile of a cell composition. In particular embodiments, the methods provided herein generate such profiles with a higher resolution and degree of accuracy than existing methods for monitoring surface glycan expression in cells. For example, in some embodiments, the methods provided herein detect individual glycan species that are present in lower amounts within a sample than existing methods, allowing for the detection and/or monitoring of more individual glycans present in a cell composition than would be allowed by available techniques.

In some embodiments, the methods provided herein provide one or more steps whereby glycans are directly released from the cell surface, e.g., from proteins expressed and/or localized at the cell surface. This is in contrast to many existing methods, which rely on a prior step of lysing the cells and/or purifying proteins, e.g., membrane proteins, prior to a step of releasing glycans from their respective glycoconjugate. In some embodiments, one advantage of the presently claimed methods is that by stimulating the release of surface glycans from intact cells, only surface exposed glycans are collected. Glycans, including O-glycans and N-glycans, are also present internally in cells, for example expressed on nascent polypeptides processed in the Golgi apparatus, or as additions or modifications on signaling molecules. Therefore, glycans collected by other methods that involve steps of lysing cells and/or obtaining cell homogenates may contain mixtures of internally and externally localized glycans, or at the very least, include some fraction of glycans that were not expressed on the surface. In contrast, particular embodiments of the methods provided herein collect a distinct pool of glycans that were expressed on the surface.

In some embodiments, an additional advantage of releasing glycans directly from the cell surface, as opposed, for example, to methods that involve lysing cells, is that the cells remain intact even after the glycans have been removed. Thus, in some embodiments, cells from the same composition may be further analyzed with additional techniques after the glycans have been removed. In some embodiments, cells are processed for further analysis after surface glycans are removed, e.g., microarray or proteomics.

In particular embodiments, the methods provided herein remove surface glycans without exposing the cell surface to proteases, such as trypsin. In particular embodiments, one advantage of avoiding the use of proteases to remove surface glycans is that the surface exposed proteins remain intact. In some embodiments, this may allow for further analysis of the cells, such as by flow cytometry, where the removal of surface glycans may expose additional targets for sorting, or allow for surface exposed proteins to be isolated and further analyzed. For example, enzymatic release of N-glycans attached to the nitrogen of asparagine, thereby converting asparagine to aspartate. In certain embodiments, another advantage of avoiding proteases to remove surface glycans is that particular glycans may be selectively removed by selection of the appropriate agents or conditions. For example, an agent may be chosen that selectively releases N-glycans while leaving O-glycans attached at the cell surface, a selectivity that might not be achieved by digesting surface proteins.

In certain embodiments, the methods provided herein provide a means to detect surface glycan expression with a high degree of accuracy and sensitivity that is not achieved by existing methods. Thus, in some embodiments, the methods provided herein provide a means to assess the physiology and functionality of cell compositions, including therapeutic and pharmaceutical cell compositions.

In some aspects, the provided methods permit characterization of the cell surface glycome of any cell preparation or composition. Because glycosylation has been implicated in cell signaling, adhesion, homing properties and other functional activities or properties, it is contemplated that differences in the cell surface glycome may provide a useful tool for analyzing and assessing functional differences between and among cell compositions. In some aspects, the methods can be used to assess features of cell therapies, such as chimeric antigen receptor (CAR+) T cell therapies, including cell therapies involving multiple ex vivo processing steps before infusion into a subject. In some aspects, the various processes involved in engineering a cell therapy, including but not limited to, cell isolation, selection, cryopreservation, stimulation, activation, transduction, expansion and/or formulation, may impact or alter one or more features of a therapeutic cell composition.

In some embodiments, however, the current analytical tools for studying and evaluating cell compositions, including therapeutic cell compositions, are primarily confined to targeted examination of cell surface or internal markers via flow cytometry. As an alternative, the provided methods permit the generation of a robust glycan map, including high resolution chromatography and, in some cases, combined with high resolution mass spectrometry to allow for detailed characterization and identification of surface N-glycans. In some embodiments, the methods herein provide an unbiased technique to characterize, investigate, and/or evaluate cell compositions, including therapeutic cell compositions, including impacts of different processes or features between and among different cell compositions.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. ASSESSING CELL SURFACE GLYCAN EXPRESSION PROFILES

Provided herein are methods of identifying, quantifying, and/or analyzing glycans, e.g., N-glycans, that are expressed on the surface of cells. In certain embodiments, the presence, absence, and relative abundance of individual glycan species are detected with high resolution and sensitivity. In certain embodiments, the methods include procedures and/or modifications to improve the detection of the glycans. In certain embodiments, the detection of the glycans may be performed by a technique capable of identifying and/or quantifying amounts of individual species of glycans. In certain embodiments, a species of glycans includes glycans that have identical structures that are different from the structures of other glycan species. In particular embodiments, the technique is a mass spectrometry technique and/or a liquid chromatography (LC) technique, such as high performance liquid chromatography (HPLC) or ultra performance liquid chromatography (UPLC).

A. Treating the Cells

In certain embodiments, a composition of cells is incubated, cultured, or treated under conditions suitable to remove, release, or detach glycans, e.g., N-glycans, from the surface of the cells of the composition. In certain embodiments, a composition of cells is treated, incubated, and/or contacted with an agent to remove, separate, or detach glycans, e.g., N-glycans, from the surface of the cells. In particular embodiments, the cells are intact, i.e., the cells are not lysed or homogenized prior to treatment with the agent. In certain embodiments, the cells are live cells. In some embodiments, treating, incubating, and/or contacting the cells with the agent does not disrupt and/or rupture the cell membrane. In some embodiments, the cells are live cells, and treating, incubating, or contacting the cells with the agent does not kill the cells. In certain embodiments, the cells are live cells, and treating, incubating, or contacting the cells with the agent does not induce cell death, e.g., apoptosis or necrosis in the cells.

In some embodiments the cells are washed and/or rinsed prior to the glycan digestion. In some embodiments, the cells are washed and/or rinsed by removing media, e.g., cell culture media, from the cells and/or adding a solution such as a fresh solution, e.g., a solution that has not previously been contacted or exposed to the cells. In some embodiments, the solution is a buffer and/or media. Suitable buffers for washing and/or rinsing cells are known, and include those that do not lyse cells and/or do not otherwise kill live cells. In some aspects, suitable solutions include, but are not limited to, saline solution, citrate buffer, Dulbecco's Phosphate Buffered Saline (DPBS), Earle's Balanced Salt Solution (EBSS), Gey's balanced salt solution, Hanks' Balanced Salt Solution (HBSS), HEPES (N-2-hydroxyethylpiperazine-N'-2-ethanesulphonic acid) buffer, Krebs-Heneseleit buffer solution, Krebs-Ringer solution, MES buffer, MOPS buffer, phosphate buffer, phosphate buffered saline (PBS), Ringer solution, Tris buffer, Trizma buffer, Tyrode's solution, or modifications or variations thereof. In particular aspects, suitable media is or includes, but is not limited to BME, DMEMF12, DMEMF12, DMEM, DMEM High Glucose, F-12, F-12K, ES Qualified DMEM, GMEM, IDIM, Iscove's Modified DMEM, McCoy's 5A, MEM, RPMI, StemXvivo, Xvivo, or variations or modifications thereof.

In some embodiments, the rinsing or washing includes centrifugation. In some aspects, the cells are transferred into a container, e.g., a vial or tube, and are centrifuged at a low speed, e.g., a speed that does not damage or kill the cells. In some embodiments, the centrifugation pellets the cells. In certain embodiments, after the centrifugation, the supernatant is removed from the cell pellet. In particular embodiments, the centrifugation is performed for, for about, or for less than 60 minutes, 30 minutes, 15 minutes, 10 minutes, 5 minutes 4 minutes, 3 minutes, 2 minutes, 90 seconds, 60 seconds, 30 seconds, or 15 seconds. In certain embodiments, the centrifugation is performed at, at about, or at less than 16,000×g, 12,000×g, 10,000×g, 8,000×g, 6,000×g, 5,000×g, 4,000×g, 3,000×g, 2,000×g, 1,000×g, 800×g, 600×g, 500×g, 400×g, 300×g, 200×g, 100×g, or 50×g. In certain embodiments, the cells are centrifuged for or for about 3 minutes at or at about 500×g. In particular embodiments, the cells are centrifuged for or for about 3 minutes at or at about 300×g. After centrifugation, the supernatant may be removed and a fresh solution may be added and/or contacted to the cells. Optionally the pellet may be disrupted or agitated, such as by vortex or pipet mixing, to disperse the cells into the solution.

In some embodiments, the cells are rinsed in solution, e.g., fresh solution, such as with a suitable buffer or media once, twice, three times, four times, five times, six times, seven times, eight times, nine times, ten times, or more than ten times prior to the glycan digestion.

In some embodiments, the cells are treated and/or incubated with an enzyme prior to glycan digestion. In some embodiments, the cells are treated with an enzyme to remove or digest extracellular polynucleotides, e.g., RNA and DNA molecules. In certain embodiments, the enzyme is a nuclease. In particular embodiments, the enzyme is benzonase.

In some embodiments, a composition of cells that is incubated, cultured, or treated under conditions suitable to remove, release, or detach glycans, e.g., N-glycans, from the surface of the cells is a test cell composition or test composition. In particular embodiments, the test cell composition or test composition is a population and/or a plurality of cells from a source composition. In some cases, the test composition is a sample of the source composition, e.g. has been removed from a source composition containing a larger composition of the cells. In such embodiments, the cells in the test cell composition are identical or substantially identical to the source composition except that the test composition generally contains a smaller volume and/or number or absolute number of the cells. In some embodiments, the test cell composition is of a sufficient size to carry out the provided methods, and does not substantially interfere with or affect features of the source composition. In particular embodiments, the source composition is a therapeutic cell composition or is a cell composition that is at a stage or step within a process to manufacture a therapeutic cell composition.

In certain embodiments, the composition of cells, e.g. test cell composition, that is treated with the agent, such as N-glycosidase, e.g., PNGase F, contains between $1 \times 10^3$ cells and $1 \times 10^{12}$ cells, between $1 \times 10^4$ cells and $1 \times 10^8$ cells, between $1 \times 10^5$ cells and $1 \times 10^7$ cells, between $1 \times 10^6$ cells and $1 \times 10^7$ cells, or between $1 \times 10^6$ cells and $5 \times 10^6$ cells. In some embodiments, the composition of cells, e.g. test cell composition, contains at least or at least about $1 \times 10^3$ cells, at least or at least about $5 \times 10^3$ cells, at least or at least about $1 \times 10^4$ cells, at least or at least about $5 \times 10^4$ cells, at least or at least about $1 \times 10^5$ cells, at least or at least about $5 \times 10^5$ cells, at least or at least about $6 \times 10^5$ cells, at least or at least about $7 \times 10^5$ cells, at least or at least about $8 \times 10^5$ cells, at least or at least about $9 \times 10^5$ cells, at least or at least about $1 \times 10^6$ cells, at least or at least about $2 \times 10^6$ cells, at least or at least about $3 \times 10^6$ cells, at least or at least about $4 \times 10^6$ cells, at least or at least about $5 \times 10^6$ cells, at least or at least about $6 \times 10^6$ cells, at least or at least about $7 \times 10^6$ cells, at least or at least about $8 \times 10^6$ cells, about $9 \times 10^6$ cells, at least or at least about $1 \times 10^7$ cells, at least or at least about $5 \times 10^7$ cells, at least or at least about $1 \times 10^8$ cells, at least or at least about $5 \times 10^8$ cells, at least or at least about $1 \times 10^9$ cells, at least or at least about $1 \times 10^{10}$ cells, at least or at least about $1 \times 10^{11}$ cells, or at least or at least about $1 \times 10^{12}$ cells. In certain embodiments, the composition of cells, e.g. test cell composition, contains between $1 \times 10^6$ cells and $5 \times 10^6$ cells. In particular embodiments, the composition of cells, e.g. test cell composition, contains between $1 \times 10^6$ cells and $2.5 \times 10^6$.

In some embodiments, the composition of cells, e.g. test cell composition, incubated with the agent, such as N-glycosidase (e.g. PNGase F) has a concentration of between $1 \times 10^3$ cells/mL and $1 \times 10^{12}$ cells/mL, between $1 \times 10^4$ cells/mL and $1 \times 10^8$ cells/mL, between $1 \times 10^5$ cells/mL and $1 \times 10^7$ cells/mL, or between $1 \times 10^6$ cells/mL and $1 \times 10^7$ cells/mL. In particular embodiments, the composition of cells, e.g. test cell composition, has a concentration of at least or at least about $5 \times 10^4$ cells/mL, at least or at least about $1 \times 10^5$ cells/mL, at least or at least about $5 \times 10^5$ cells/mL, at least or at least about $6 \times 10^5$ cells/mL, at least or at least about $1 \times 10^6$ cells/mL, at least or at least about $5 \times 10^6$ cells/mL, at least or at least about $5 \times 10^6$ cells/mL, at least or at least about $6 \times 10^6$ cells/mL, at least or at least about $7 \times 10^6$ cells/mL, at least or at least about $8 \times 10^6$ cells/mL, at least or at least about $9 \times 10^6$ cells/mL, at least or at least about $1 \times 10^7$ cells/mL, at least or at least about $1.25 \times 10^7$ cells/mL, at least or at least about $2.5 \times 10^7$ cells/mL, at least or at least about $5 \times 10^7$ cells/mL, at least or at least about $1 \times 10^8$ cells/mL, at least or at least about $5 \times 10^8$ cells/mL, at least or at least about $1 \times 10^9$ cells/mL, at least or at least about $1 \times 10^{10}$ cells/mL, at least or at least about $1 \times 10^{11}$ cells/mL, or at least or at least about $1 \times 10^{12}$ cells/mL. In some embodiments, the composition, e.g. test cell composition, has a concentration of cells of between $5 \times 10^6$ cells/mL and $2.5 \times 10^7$ cells/mL. In certain embodiments, the composition of cells, e.g. test cell composition, has a concentration of between $5 \times 10^6$ cells/mL and $1.25 \times 10^7$ cells/mL. In certain embodiments, the composition, e.g. test cell composition, contains a concentration of at least or at least about or about $5 \times 10^6$ cells/mL. In particular embodiments, the composition, e.g. test cell composition, contains a concentration of at least or at least about or about $1.25 \times 10^7$ cells/mL. In some embodiments, the composition, e.g. test cell composition, contains a concentration of at least or at last about or about $2.5 \times 10^7$ cells/mL.

In some embodiments, the incubation, culture or treatment is carried out in a total volume of from or from about 0.005 mL to 50 mL, 0.005 mL to 25 mL, 0.005 mL to 10 mL, 0.005 mL to 5 mL, 0.005 mL to 1 mL, 0.005 mL to 0.5 mL, 0.005 mL to 0.05 mL, 0.05 mL to 50 mL, 0.05 mL to 35 mL, 0.05 mL to 10 mL, 0.05 mL to 5 mL, 0.05 mL to 1 mL, 0.05 mL to 0.5 mL, 0.5 mL to 50 mL, 0.5 mL to 25 mL, 0.5 mL to 10 mL, 0.5 mL to 5 mL, 0.5 mL to 1 mL, 1 mL to 50 mL, 1 mL to 25 mL, 1 mL to 10 mL, 1 mL to 5 mL, 5 mL to 50 mL, 5 mL to 25 mL, 5 mL to 10 mL, 10 mL to 50 mL, 10 mL to 25 mL or 25 mL to 50 mL. In some embodiments, the incubation, culture or treatment is carried out in a total volume of at least or at least about 0.005 mL, 0.01 mL, 0.05 mL, 0.1 mL, 0.2 mL, 0.3 mL, 0.4 mL, 0.5 mL, 1 mL, 2.0 mL, 5 mL, 10 mL, 20 mL, 30 mL, 40 mL or 50 mL.

1. Agent, e.g. N-Glycosidase

In some embodiments, the composition of cells is treated, incubated, and/or contacted with an agent, e.g. N-glycosidase, e.g. PNGase F, resulting in a removal, separation, and/or detachment of glycans, e.g., N-glycans, from the surface exposed glycoconjugate. In some embodiments, the glycoconjugate is a protein, e.g., a glycoprotein. In particular embodiments, the treating, contacting, and/or incubating the composition of the cells with the agent results in the removal, separation, and/or detachment of glycans from a surface exposed protein. In particular embodiments, the released, removed, and/or detached N-glycans are intact. In some embodiments, the removal, separation, and/or detachment of the glycans from the surface exposed protein does not damage, digest, and/or otherwise alter the structure of the glycan. In particular embodiments, the removal, separation, and/or detachment of the glycans from the surface exposed protein does not damage, digest, and/or otherwise alter the structure of the moiety, e.g., protein, from which the glycan has been released. In some embodiments, the removal, separation, and/or detachment of the glycans from the surface exposed protein results in the conversion of asparagine to aspartate, but does not otherwise damage, digest, and/or alter the structure of the protein from which the glycan has been released.

In certain embodiments, the agent removes a glycan from a glycoconjugate, e.g., a surface exposed glycoprotein. In some embodiments, the glycan is a polysaccharide. In certain embodiments, the glycan is a branched glycan, a linear glycan, an N-linked glycan, an O-linked glycan, or a combination thereof. In certain embodiments, the agent removes an N-glycan from a glycoconjugate. In particular embodiments, N-glycans are covalently attached to proteins at asparagine (Asn) residues by an N-glycosidic bond, most commonly an N-acetylglucosamine to asparagine (GlcNAcβ1-Asn). In certain embodiments, N-glycans are attached to asparagines via an N-acetylglucosamine ("GlcNAc") residue in an Asn-Xxx-(Ser, Thr) motif, where Xxx can be any amino acid except proline.

In certain embodiments, all N-glycans share a common core sugar sequence, Manα1-6(Manα1-3)Manβ1-4GlcNAcβ1-4GlcNAcβ1-Asn-X-Ser/Thr. In particular embodiments, N-glycans may be classified into three types: (1) oligomannose, in which only mannose residues are attached to the core; (2) complex N-glycans, in which "antennae" initiated by N-acetylglucosaminyltransferases (GlcNAcTs) are attached to the core; and (3) hybrid, in which only mannose residues are attached to the Manα1-6 arm of the core and one or two antennae are on the Manα1-3 arm. In some embodiments, N-glycans include N-glycans with high mannose content, i.e., high mannose N-glycans, bisected and/or sialyl Lewis$^x$ N-glycans, or N-acetyl lactosamine containing N-glycans. In some embodiments, examples of various N-linked glycan families include, but are not limited to, (a) the A2 family (disialylated, biantennary N-linked oligosaccharides; including A1 glycans (monosialylated, biantennary N-linked oligosaccharide), NA2 glycans (asialo-biantennary N-linked oligosaccharide); NGA2 glycans (asialo-, agalacto-biantennary N-linked oligosaccharide); M3N2 glycans, etc.); (b) the A2F family (disialylated, biantennary N-linked oligosaccharide with core fucose; including A1F glycans (monosialylated, biantennary N-linked oligosaccharide with core fucose), NA2F glycans (asialo-biantennary N-linked oligosaccharide with core fucose) NGA2F glycans (asialo-, agalacto-biantennary N-linked oligosaccharide with core fucose), etc.); (c) the A3 family (e.g., glycans fully sialylated on the non-reducing terminal galactosyl residues but differing in the distribution of a2,3 and a2,6 linked sialyl residues and the linkage one of the galactoses; including NA3 (asialo tri-antennary N-linked oligosaccharide derived from an A3 glycan) and NGA3 glycans (agalacto-triantennary N-linked oligosaccharide derived from an NA3 glycan), etc.); (d) the A4 family (glycans derived from tetra-antennary N-linked oligosaccharides; including NA4 glycans (asialo-tetraantennary N-linked oligosaccharide); NGA4 glycans (asialo-, agalacto-tetraantennary N-linked oligosaccharide derived from NA4 glycans); etc.); and (e) oligomannose family glycans (e.g., Man-5, Man-6, Man-7, Man-8, Man-9, etc. glycans). Examples of N-glycans include, but are not limited to, a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and a high mannose glycan having nine mannose residues.

In some embodiments, the agent is any agent that facilitates the removal, separation, and/or detachment of glycans, e.g., N-glycans, from a glycoconjugate, e.g., a glycoprotein. In certain embodiments, the agent chemically removes the glycan from the glycoconjugate, for example but not limited to hydrazinolysis or alkali β-elimination.

In certain embodiments, the agent is an enzyme. In particular embodiments, the agent is an enzyme that specifically removes, separates, and/or detaches N- or O-linked glycans from a glycoconjugate. In certain embodiments, the agent is an amidase. In some embodiments, the agent is or includes a glycosidase, such as an N-glycosidase. In particular embodiments, the agent is or includes Endoglycosidase H (Endo H), Endoglycosidase F (EndoF), N-Glycosidase A (PNGase A), or N-Glycosidase F (PNGase F) or combinations thereof. In some embodiments, the agent is or includes an amidase of the peptide-N4-(N-acetyl-beta-glucosaminyl) asparagine amidase class. In particular embodiments the agent is or includes a PNGase F.

In some embodiments, the agent is an enzyme that releases or is capable of releasing full-length oligosaccharides from proteins and peptides having N-linked carbohydrates. In some embodiments, the agent is a PNGase F that releases, or is capable of releasing, full-length oligosaccharides from proteins and peptides having N-linked carbohydrates. In certain embodiments, the agent is not or does not include endoglycosidases, such as Endo F, Endo H, and Endo D. In some embodiments, endoglycosidases, such as Endo F, Endo H, and Endo D do not release full-length oligosaccharides and/or do not cleave all common classes of N-linked oligosaccharides from glycoproteins.

In certain embodiments, the agent is not a protease. In some embodiments, the agent does not include a protease. In particular embodiments, the agent is not serine protease, a cysteine protease, a threonine protease, an aspartic protease, a glutamic protease, a metalloprotease, or asparagine peptide lyases. In certain embodiments, the agent is not and does not include an endopeptidase, e.g., trypsin, chymotrypsin, pepsin, papain, and elastase. In particular embodiments, the agent is not and does not include trypsin.

In particular embodiments, the agent selectively and/or specifically removes, separates, and/or detaches an N-glycan from a glycoconjugate, e.g., a surface exposed protein or glycoprotein. In certain embodiments, the agent has a greater activity for the removal, separation, and/or detachment of an N-glycan than for the removal, separation, and/or detachment of a glycan that is not an N-glycan. In certain embodiments, the agent has a at least a 5%, 10%, 20%, 30%, 40%, 50%, 60%, 70%, 80%, 90%, 100%, or at least a 1-fold, 2-fold, 3-fold, 4-fold, 5-fold, 10-fold, 20-fold, 30-fold, 40-fold, 50-fold, 60-fold, 70-fold, 80-fold, 90-fold, 100-fold, 500-fold, or 1,000 fold greater activity for the removal, separation, and/or detachment of an N-glycan than for the removal, separation, and/or detachment of a glycan that is not an N-glycan. In certain embodiments, the agent is or includes a PNGase F.

PNGase F

In particular embodiments, incubation under conditions that are suitable to remove, release, or detach glycans from the surface of cells includes contacting, treating, and/or incubating the cells with an agent. In particular embodiments, the agent is or includes a PNGase F. PNGase F is an amidase of the peptide-N4-(N-acetyl-beta-glucosaminyl) asparagine amidase class. In some embodiments, PNGase F is a bacterial enzyme that releases N-glycans from an asparagine. In particular embodiments, the PNGase F releases the entire, i.e., intact, N-glycan from the asparagine. In certain embodiments, PNGase F removes oligomannose, hybrid, and complex N-glycans attached to asparagine. In particular embodiments, PNGase F releases N-glycans attached to the nitrogen of asparagine, thereby converting asparagine to aspartate. In certain embodiments, the cleavage occurs at a position of the carbohydrate that is adjacent to the asparagine residue. In particular embodiments, the agent is or includes an enzyme that exhibits peptide-N— (N-acetyl-β-N-glucosaminyl) asparagine aminidase activity. In certain embodiments, a composition of cells is treated, contacted, or incubated with an agent that is or includes a PNGase F.

In certain embodiments, the agent is or includes a PNGase F polypeptide or a portion thereof. In some embodiments, the agent is a PNGase F that is derived from a bacteria or purified from an almond emulsion. In particular embodiments, the agent is a PNGase F that is derived from a bacteria. In some embodiments, the bacteria is *Flavobacterium meningosepticum*. In some embodiments, *Flavobacterium meningosepticum* is also known as *Elizabethkingia meningosepticum*. In certain embodiments, the agent contains all or a portion of the amino acid sequence set forth in SEQ ID NO: 1. In particular embodiments, a portion of a PNGase F polypeptide is or contains at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, or at least 350 contiguous amino acids of the amino acid sequence set forth in SEQ ID NO: 1. In some embodiments, the agent has at least 70%, at least 75%, at least 80%, at least 85%, at least 90%, at least 95%, at least 96%, at least 97%, at least 98%, at least 99%, or at least 99.5% to all or a portion of the PNGase F amino acid sequence set forth in SEQ ID NO: 1.

In some embodiments, the PNGase F is or includes a PNGase F preparation of a high purity. In some embodiments, the PNGase F is or includes a PNGase F preparation that is free of proteases. In certain embodiments, the PNGase F is or includes a PNGase F preparation that is free of Endo H, EndoF, and/or PNGase A activity. In particular embodiments, the PNGase F is or includes a PNGase F preparation that is free of endotoxin. In some embodiments, the PNGase F is or includes a PNGase F that is at least 75%, at least 80%, at least 85%, at least 90%, at least 95%, at least 96%, at least 97%, at least 98%, at least 99%, at least 99.5%, at least 99.7%, at least 99.8%, at least 99.9%, or at least 99.99% pure. In particular embodiments, the PNGase F is a preparation with less than 20%, less than 10%, less than 5%, less than 1%, less than 0.5%, less than 0.1%, less than 0.01%, or less than 0.001% non-PNGase F protein contaminants. In some embodiments, the PNGase F preparation is substantially homogenous. In some embodiments, the PNGase F is or includes a PNGase F that is at least 75%, at least 80%, at least 85%, at least 90%, at least 95%, at least 96%, at least 97%, at least 98%, at least 99%, at least 99.5%, at least 99.7%, at least 99.8%, at least 99.9%, or at least 99.99% homogenous.

In some embodiments, the purity and/or homogeneity of the PNGase F is or may be assessed by any suitable means, including but not limited to sodium dodecyl sulfate polyacrylamide gel electrophoresis (SDS-PAGE), gel permeation chromatography (GPC), size exclusion chromatography (SEC), liquid chromatography (LC), high performance liquid chromatography (HPLC), mass spectrometry, circular dichroism (SD), nuclear magnetic resonance (NMR), and fluorescence spectroscopy (fluorometry). In some embodiments, purity and/or homogeneity is assessed or determined by SDS-PAGE and protein staining, such as by Coomasie Blue staining.

In certain embodiments, the PNGase F is not derived, obtained, or purified from an almond emulsion.

In some embodiments, the PNGase F, or a mutant or portion thereof, is a rapid-acting PNGase F, such as a PNGase F with activity to cleave or release one or more N-glycans in less than 24 hours, such as generally less than 12 hours, for example, between 15 minutes and 4 hours, such as generally no more than 15 minutes, no more than 30 minutes, no more than 60 minutes, no more than 2 hours, no more than 3 hours or no more than 4 hours.

In some embodiments, PNGase F, or a mutant or portion thereof, is provided in an amount that is an enzymatically effective amount to affect release of one or more N-glycans from a glycoprotein or glycoproteins. In some embodiments, the activity is effective for release or cleavage of one or more N-glycans from a glycoprotein or glycoproteins that is a native or non-denatured protein, e.g. present in its native structure, such as when purified or when expressed on the surface of a cell. In particular embodiments, the amount of the PNGase F is an amount to exhibit the activity (enzymatic activity) to release the one or more N-glycans from the glycoprotein or glycoproteins within a certain period of time and temperature, which is typically a time and temperature at which a majority of cells of a cell composition remain viable and/or are not detrimentally affected by the incubation. In some cases, the period of time is no more than 12 hours, no more than 8 hours, no more than 6 hours, no more than 4 hours, no more than 2 hours, no more than 1 hour, no more than 30 minutes, or any value or range in between any of the foregoing. In some embodiments, the temperature is less than or less than about 40° C., such as temperature of about 10° C., about 15° C., about 20° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C., or any value or range in between any of the foregoing. In some embodiments, the temperature is between or between about 10° C. and 45° C., or between 24° C. and 40° C., or between 35° C. and 39° C. In some embodiments, the temperature is or is about 37° C.

In some embodiments, the enzymatically effective amount results in substantial deglycosylation of the glycoprotein or glycoproteins during the incubation, e.g. for the period of time and at the temperature, such as activity to effect release or removal of greater than 50%, greater than 55%, greater than 60%, greater than 65%, greater than 70%, greater than 75%, greater than 80%, greater than 85%, greater than 90%, greater than 95%, greater than 99%, about 100%, or 100% of N-glycans present on the glycoprotein or glycoproteins, including when in native or non-denatured form, e.g. when present or expressed on the surface of a cell.

In some embodiments, the activity of a PNGase F enzyme may be expressed as a unit. In certain embodiments, the units are predefined. In particular embodiments, a unit is an amount of PNGase F required to remove an amount of glycan, e.g., N-glycan, from an amount of a glycoprotein, e.g., a purified glycoprotein, in an amount of time under specific conditions. In some embodiments, the glycoprotein is a denatured glycoprotein. In certain embodiments the glycoprotein is a glycoprotein in its native structure. In some embodiments, the unit is an amount of PNGase F required to remove greater than 50%, greater than 55%, greater than 60%, greater than 65%, greater than 70%, greater than 75%, greater than 80%, greater than 85%, greater than 90%, greater than 95%, greater than 99%, about 100%, or 100% of the glycan from the amount of the glycoprotein. In some embodiments, the reaction volume is about 0.1 µl, about 1 µl, about 5 µl, about 10 µl, about 20 µl, about 30 µl, about 40 µl, about 50 µl, about 100 µl, about 200 µl, about 250 µl, about 500 µl, about 1 mL, about 2 mL, about 3 mL, about 4 mL, about 5 mL, or about 10 mL, or any value or range in between. In certain embodiments, the amount of the glycoprotein is about 1 pmol, about 10 pmol, about 100 pmol, about 1 nmol, about 10 nmol, about 100 nmol, about 1 mmol, about 10 mmol, about 100 mmol, about 1 mol, or any value or range falling in between. In some embodiments, the amount of the glycoprotein is a concentration of about 1 nM, about 10 nM, about 100 nM, about 1 µM, about 10 µM, about 100 µM, about 1 mM, about 10 mM, about 100 mM, or about 1 M, or any value or range in between.

In some embodiments, with reference to a unit of activity of a PNGase F, the glycoprotein is a recombinant glycoprotein. In particular embodiments, the glycoprotein is purified. In some embodiments, the glycoprotein is dabsyl fibrin glycopeptide. In certain embodiments, the glycoprotein is fetuin. In particular embodiments, the glycoprotein is denatured Ribonuclease B (RNase B). In certain embodiments, the unit is further defined by conditions of the incubation that include the composition of the buffer that the PNGase and the glycoprotein are incubated in, the pH of the buffer, temperature, and the total volume, i.e., reaction volume.

Exemplary units of PNGase F activity include, but are not limited to, a unit as defined as the amount of PNGase F enzyme required to remove >95% of the carbohydrate from 10 µg of denatured RNase B in 1 hour at 37° C. in a total reaction volume of 10 µl; required to catalyze the release of N-linked oligosaccharides from one nmol of denatured Ribonuclease B in 1 minute at pH 7.5 at 37° C.; required to catalyze the deglycosylation of 1 nmol of denatured RNase B in 30 minutes at 37° C.; required to catalyze the release of N-linked oliogosaccharides from 1 µmol denatured RNase B per minute at pH 7.5 at 37° C.; or required to hydrolyze carbohydrates from 1 nmol dabsyl fibrin glycopeptide per minute at pH 7.8 at 37° C. In particular embodiments, the unit is the amount of PNGase F activity that is required to catalyze the deglycosylation of 1 nmol of denatured RNase B in 30 minutes at 37° C.

Certain embodiments contemplate that one of skill in the art can determine the amount of PNGase F in a predefined unit as a matter of routine. In particular embodiments, the amount of a PNGase F enzyme in a unit is determined by an assay that measures or quantifies the removal, release, deglycosylation, and/or hydroxylation of carbohydrates, e.g., N-glycans, from a glycoprotein, e.g., a purified glycoprotein. In some embodiments, the PNGase F activity is measured by detecting the amount of N-glycans on a glycoprotein that was treated with PNGase under defined conditions and comparing it to an amount of N-glycans on an untreated glycoprotein e.g., a separate pool of untreated glycoprotein or the glycoprotein prior to treatment with the PNGase F.

In some embodiments, methods for detecting N-glycans on the glycosylated proteins may include staining and affinity-based methods. In certain embodiments, the glycoprotein is run on a gel, e.g., an SDS-PAGE gel, following incubation with the PNGase F enzyme, and optionally staining the gel is stained for glycoproteins. In some embodiments, protein bands corresponding to the glycosylated protein are compared to bands corresponding to the unglycosylated protein. Suitable gel-staining procedures are include, but are not limited to stains that are based on the periodic acid-Schiff (PAS) reaction, in which periodic acid oxidizes two vicinal diol groups to form an aldehyde, which reacts with the Schiff reagent to give a magenta color. In some embodiments, the chromogenic gel staining is performed with acid fuchsin, which can be detected fluorescently at 535 nm. Suitable methods for gel staining including the use of commercially available fluorescent stains that utilize periodate oxidation to attach a fluorescent hydrazide. Suitable gel stains also include alcian blue and Stains-All, which are used for detecting proteoglycans, glycosaminoglycans, and negatively charged glycoproteins. In certain embodiments, the N-glycans by the PGNase F enzyme is determined by lectin blot, e.g., a western blot that is probed with a lectin, e.g., a detectably labeled lectin.

In some embodiments, the enzymatically effective amount of the N-glycosidase, e.g. PNGase F, is from or from about 1 unit to 5000 units, 1 unit to 1000 units, 1 unit to 500 units, 1 unit to 250 units, 1 unit to 100 units, 1 unit to 50 units, 1 unit to 25 units, 25 units to 5000 units, 25 units to 1000 units, 25 units to 500 units, 25 units to 250 units, 25 units to 100 units, 25 units to 50 units, 50 units to 5000 units, 50 units to 1000 units, 50 units to 500 units, 50 units to 250 units, 50 units to 100 units, 100 units to 5000 units, 100 units to 1000 units, 100 units to 500 units, 100 units to 250 units, 250 units to 5000 units, 250 units to 1000 units, 250 units to 500 units, 500 units to 5000 units, 500 units to 1000 units, or 1000 units to 5000 units, each inclusive. In some embodiments, the enzymatically effective amount of the N-glycosidase, e.g. PNGase F, is greater than or greater than about or is or is about 1 unit, 5 units, 10 units, 15 units, 20 units, 25 units, 50 units, 100 units, 250 units, 500 units, 1000 units, 2500 units or 5000 units. It is within the level of a skilled artisan to determine the unit of activity and/or specific activity of a preparation of an N-glycosidase, e.g. PNGase F. Exemplary methods for assessing or determining unit of activity are described above, and may depend on the particular source of the N-glycosidase, e.g. PNGase F. In some instance, one unit is an amount of the N-glycosidase, optionally PNGase F, sufficient to catalyze the deglycosolation of 1 nanomole of denatured Ribonuclease B (RNase B) in 30 minutes at 37° C. In other instances, 500 units is an amount of the N-glycosidase, optionally PNGase F, sufficient to catalyze the deglycosylation of 10 µg of Ribonuclease B (RNase B) incubated in 1×PBS for 5-10 minutes at 37° C. or room temperature.

In some embodiments, the PNGase F is a recombinant PGNase F. In certain embodiments, the PNGase F a mutant PNGase F. In some embodiments, the PNGase F is a recombinant PNGase F that is cloned from *Flavobacterium meningosepticum*. In particular embodiments, the PNGase F is cloned from the entire PNGase F gene of *Flavobacterium meningosepticum*. In certain embodiments, the entire PNGase F gene of *Flavobacterium meningosepticum* is the PNGase F gene described in Tarentino et al., Journal of Biological Chemistry, 265(12): 6961-6966 (1990). In particular embodiments, the entire PNGase F gene is a PNGase F gene that encodes a PNGase F polypeptide that is designated with the Uniprot Accession number P21163.2. In some embodiments, the entire PNGase F gene is a PNGase F gene that encodes a PNGase F polypeptide with the amino acid sequence set forth in SEQ ID NO: 1.

In particular embodiments, the PNGase F achieves complete deglycosylation of RNase B within 5-10 minutes at 37° C. or at room temperature. In some embodiments, the PNGase F with an increased and/or rapid activity is a PNGase F that achieves complete deglycosylation of 10 μg of RNase B when one unit of the PGNase F is incubated for 5-10 minutes at 37° C. or at room temperature. In particular embodiments, the complete deglycosylation is visualized by SDS-PAGE. In particular embodiments, the purity of the PNGase F at least 95% or greater as determined by SDS-PAGE analysis and staining with Coomassie Brilliant Blue. In some embodiments, the PNGase F releases N-glycans from the native form of the blood borne glycoprotein fetuin within minutes at room temperature or at 37° C.

In some embodiments, the PNGase F is a PNGase F that is capable of removing, releasing, and/or detaching N-glycans within minutes when incubated with a native glycoprotein at room temperature or at 37° C. In particular embodiments, the PNGase F is capable of removing, releasing, and/or detaching an amount of N-glycans from frozen and formalin-fixed paraffin-embedded liver tissue sections within 2 hours at 37° C., wherein the amount of released N-glycans is detectable by mass spectrometry, e.g., MALDI-MS (see for example Powers et al. Analytical Chemistry, 85(20):9799-806 (2013). In certain embodiments, the PNGase F is capable of removing, releasing, and/or detaching an amount of N-glycans from frozen mouse brain tissue sections when 0.2 mL solution of 0.1 mg/mL is applied to the section and incubated for 2 hours at 37° C., wherein the amount of released N-glycans is detectable by mass spectrometry, e.g., MALDI-MS (see for example, Powers et al., Biomolecules 5: 2554-2572 (2015)).

In particular embodiments, the PNGase F deglycosylates proteins in their native form. In certain embodiments, the PNGase F removes N-glycans from one or more glycoproteins that are in their native form. In some embodiments, the PNGase F releases, removes, and/or detaches glycans from one or more glycoproteins that are in their native form within minutes at room temperature. In certain embodiments, the PNGase F releases, removes, and/or detaches glycans from one or more glycoproteins that are in their native form within minutes at room temperature or at 37° C. In certain embodiments, the PNGase F releases, removes, and/or detaches at least 10%, at least 20%, at least 30% at least 40%, at least 50%, at least 60%, at least 70%, at least 80%, at least 90%, at least 95%, at least 99%, or about 100% of glycans from one or more glycoproteins in their native form within about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 3 hours, about 4 hours, about 5 hours, about 6 hours, or between 5 minutes and 1 hour, between 1 hour and 4 hours, between 4 hours and 6 hours, or longer than 6 hours.

In particular embodiments, the PNGase F is a recombinant PNGase F that is produced by a polynucleotide that is cloned from a PNGase F gene that is expressed and purified in cells. In some embodiments, the cells are bacterial cells, e.g., *E. coli*, yeast cells, insect cells, or mammalian cells. In certain embodiments, the PNGase F is expressed in and purified from *E. coli*. In some embodiments, the PNGase F is expressed in and purified from the bacterial strain BL21 Star (DE3).

In some embodiments, the PNGase F is a recombinant PNGase F that is produced by a polynucleotide that is cloned, expressed, and purified into an expression vector. In certain embodiments, the polynucleotide encoding the PNGase F is incorporated into a vector construct containing a regulatory sequence by routine molecular techniques (See Sambrook et al, Molecular Cloning, 2nd ed., (1989)). In some embodiments, the vector includes one or more of a suitable promoter, origin of replication, ribosomal binding site, transcription termination sequence, selectable markers and multiple cloning sites. In particular embodiments, the polynucleotide encoding the PNGase F is a plasmid with an efficient and specific construct, e.g., a T7 expression vector. In certain embodiments, the vector contains an inducible promoter. In some embodiments, the polynucleotide encoding the PNGase F is inserted into an expression vector that is suitable for expression in a bacterium under the control of a suitable promoter for bacteria. In particular embodiments, the expression vector contains an inducible promoter that is recognized by the host bacterial organism and is operably linked to the polynucleotide encoding the PGNase F. Inducible promoters suitable for use with bacterial hosts include the β-lactamase and lactose promoter systems, the arabinose promoter system, including the araBAD promoter, the rhamnose promoter, an alkaline phosphatase promoter, a tryptophan (trp) promoter system, a PLtet0-1 and Plac/ara-1 promoters, and hybrid promoters such as the tac promoter. In some embodiments, other known bacterial inducible promoters and low-basal-expression promoters are suitable. In certain embodiments, the expression vector contains a lacUV5 promoter and allows for high levelisopropyl-beta-D-thiogalactopyranoside (IPTG) inducible expression of gene products from T7 expression vectors such as pET and pQE.

In some embodiments, producing the PGNase F a process whereby the polynucleotide encoding the PNGase F is cloned, expressed, and purified into a T7 expression vector. T7 expression vectors include, but are not limited to, commercially available T7 vectors such as pT7 FLAG 3, pT7 FLAG 1, pT7 MAT 1, pT7 FLAG 4, pT7 FLAG 2, pT7 MAT 2, pT7 FLAG-MAT 1, pT7 MAT-FLAG 2, pT7 MAT-FLAG 1, and pT7 FLAG-MAT 2 (Sigma), GATEWAY pDEST 14, GATEWAY pDEST 15, GATEWAY pDEST 16, GATEWAY pDEST 17, pRSET A, pRSET-BFP, pRSET-CFP, pRSET-EmGFP (Thermo Fisher), pET 29-b (Novagen) and pQE-T7(Qiagen). In certain embodiments, the polynucleotide encoding the PNGase F is cloned, expressed and purified into a pET 29-b and/or a pQE-T7T7 vector.

In some embodiments, the PNGase F contains a tag or fusion domain, e.g. affinity or purification tag, linked, directly or indirectly, to the N- and/or c-terminus of the protein. In particular embodiments, the PGNase F is produced by a process whereby the PNGase F is a recombinant PNGase F that is cloned, expressed and purified into an expression vector. In some embodiments, the insertion results in the addition of the sequence for an in frame N-terminal or C-terminal tag and/or a fusion domain. In some embodiments, the tag and/or fusion domain is an N-terminal tag of the PNGase F polypeptide. In particular embodiments, the tag and/or fusion domain is a C-terminal tag of the PNGase F polypeptide. Various suitable polypeptide tags and/or fusion domains are known, and include but are not limited to, a FITC tag, poly-histidine (His), HRP, maltose binding protein, Glu-Glu, avidin, glutathione S transferase (GST), protein A, protein G, an immunoglobulin heavy chain constant region (Fc), human serum albumin, AviTag, a Calmodulin-tag, a polyglutamate tag, a FLAGtag, an HA-tag, a Myc-tag, and fluorescent protein-tags (e.g., EGFP). In particular embodiments, the PNGase F a recombinant PNGase F with a C-terminal His tag.

In certain embodiments, the PGNase F is produced by a process whereby bacterial cells transduced with the vector containing the polynucleotide that encodes the PNGase F are induced to express the PNGase F protein. In particular embodiments, bacterial cells expressing the PNGase F polypeptide are harvested and lysed, and the PNGaseF polypeptide is purified. In some embodiments, the PNGase F polypeptide is purified. Suitable techniques for use in protein purification include, but are not limited to, precipitation with ammonium sulfate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. In some embodiments, the purification of the PNGase F polypeptide is performed by HPLC or FPLC purification. In some embodiments, the protein is purified by methods whereby a column, binds to or retains the PGNase F polypeptide by interacting with a protein tag, e.g., a C-terminal his tag, of the recombinant PGNase F polypeptide.

In particular embodiments, the agent is or includes the PNGase F that is produced from a polynucleotide that is cloned from the entire PNGase is entire Peptide N-Glycosidase F(PNGase F) gene from the genome of *Flavobacterium meningosepticum*, expressed and purified into the T7 expression vectors pET 29-b (Novagen) and pQE-T7(Qiagen). In certain embodiments, the polynucleotide that encodes the PNGase F contains an in-frame C-terminal histidine tag. In some embodiments, the polynucleotide encoding the PNGase F HIS-tagged construct is transformed into bacterial strain BL21 Star (DE3) that carries the gene for the T7 RNA polymerase under control of the lacUV5 promoter which allows for high level isopropyl-beta-D-thiogalactopyranoside (IPTG) inducible expression of gene products from T7 expression vectors such as pET and pQE. In particular embodiments, bacterial transformation and cell culture growth is performed, bacterial cells are harvested by centrifugation, and cell pellets are washed with buffers containing protease inhibitors (SigmaFast EDTA-free). In particular embodiments, the total cellular protein lysates are made using an Avestin C5 high pressure homogenizer. In some embodiments, FPLC purification methods for the recombinant PNGase F histidine tagged protein use Ni-NTA (Qiagen) and IMAC HisTrap HP (GE Healthcare) columns. In some embodiments, bacterial cell lysate from IPTG induced cultures are loaded onto the column and bound the PNGase F polypeptide with the C-terminal His tag is washed and eluted using an imidazole step gradient in binding buffer. In some embodiments, purified PNGase F with the C-terminal is dialyzed and stored in PBS buffer. In particular embodiments, the agent is or includes a PNGase that is a recombinant PNGase F with a C-terminal His tag or is a PNGase F that is identical to a PNGase F produced by the methods described in Powers et al. Analytical Chemistry, 85(20): 9799-806 (2013).

In some embodiments, the agent is or includes a PNGase F that is a commercially available PNGase F. Commercially available PNGase F includes, but is not limited to, PNGase F Proteomics Grade (Catalog #P 7367, Sigma); PNGase F (Catalog #P0704S and P0704L, New England Biolabs), PNGase F (Catalog #V4831, Promega), N-GLYCANASE (Catalog #: GKE-5006A, GKE-5006B, GKE-5006D, GKE-5016A, GKE-5016B, GKE-5016D, GKE-5010B, GKE-5016D, GKE-5020B, GKE-5020D, and GKE-5003, ProZyme), and PNGase F (Catalog #: E-PNG01, QA Bio), RAPID PNGase F (Catalog #P0710S, New England Biolabs), PNGASE F PRIME (N-Zyme Scientifics). In certain embodiments, the PNGase F is or is identical to PNGASE F PRIME (N-Zyme Scientifics).

2. Incubation Conditions

In some embodiments, a composition of cells, e.g. test composition, is contacted, treated, and/or incubated with an agent, such as an N-glycosidase, e.g. PNGase F, for about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 3 hours, about 4 hours, about 5 hours, about 6 hours, or between 5 minutes and 1 hour, between 1 hour and 4 hours, between 4 hours and 6 hours, or longer than 6 hours. In particular embodiments, the composition of cells is contacted, treated, and/or incubated with an agent that is or includes a PGNase F for an amount of time between 30 minutes and 60 minutes. In certain embodiments, a composition of cells is contacted, treated, or incubated with an agent that is or includes a PNGase F for about 30 minutes. In certain embodiments, a composition of cells is contacted, treated, or incubated with an agent that is or includes a PNGase F for about 60 minutes.

In particular embodiments, a composition of cells, e.g. test cell composition, is contacted, treated, or incubated with an agent, such as an N-glycosidase, e.g. PNGase F, and at least 70%, at least 75%, at least 80%, at least 85%, at least 90%, at least 95%, at least 97%, at least 98%, at least 99% or at least 99.9% of the surface exposed N-glycans are removed from the cells in an amount of time that is less than 6 hours, less than 5 hours, less than 4 hours, less than 3 hours, less than two hours, less than 90 minutes, less than 60 minutes, less than 45 minutes, less than 30 minutes, less than 15 minutes, or less than 5 minutes. In certain embodiments, the composition of cells, e.g. test cell composition, is incubated with an agent, such as an N-glycosidase, e.g. PNGase F, for about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes or between 5 minutes and 60 minutes, between 5 minutes and 30 minutes, between 30 minutes and 60 minutes, or between 15 minutes and 45 minutes and at least 85%, at least 90%, at least 95%, or at least 99% of the surface exposed N-glycans are removed from the cells. In particular embodiments, the composition of cells, e.g. test cell composition is incubated with an agent, such as an N-glycosidase, e.g. PNGase F, for about 30 minutes and at least 85%, at least 90%, at least 95%, or at least 99% of the surface exposed N-glycans are removed from the cells. In certain embodiments, the composition of cells, e.g. test cell composition, is incubated with an agent, such as an N-glycosidase, e.g. PNGase F for about 60 minutes and at least 85%, at least 90%, at least 95%, or at least 99% of the surface exposed N-glycans are removed from the cells.

In some embodiments, a composition of cells, e.g. test cell composition, is incubated with an agent, such as an N-glycosidase, e.g. PNGase F, to remove N-glycans from the surface of the cells under conditions that do not damage or kill the cells. In some embodiments, the incubation is for no more than or about 5 minutes, no more than or about 10 minutes, no more than or about 15 minutes, no more than or about 20 minutes, no more than or about 25 minutes, no more than or about 30 minutes, no more than or about 35 minutes, no more than or about 40 minutes, no more than or about 45 minutes, no more than or about 50 minutes, no more than or about 55 minutes, no more than or about 60 minutes, no more than or about 1.5 hours, no more than or about 2 hours, no more than or about 3 hours, no more than or about 4 hours, no more than or about 5 hours, or no more than or about six hours, wherein less than about 20%, about 15%, about 10%, about 5%, about 1%, about 0.5%, about 0.1%, about 0.05%, about 0.01%, about 0.001%, or about 0.0001% of the cells in the composition die, rupture, lyse, and/or initiate or undergo apoptosis or necrosis during the incubation. In some embodiments, the incubation is for a time that is no more than or is about 30 minutes or 60 minutes, or is an amount of time between 30 and 60 minutes, inclusive, and less than about 20%, about 15%, about 10%, about 5%, about 1%, about 0.5%, about 0.1%, about 0.05%, about 0.01%, about 0.001%, or about 0.0001% of the cells in the composition die, rupture, lyse, and/or initiate or undergo apoptosis or necrosis during the incubation.

In certain embodiments, the contact, treatment, and/or incubation with the agent, e.g., N-glycosidase, is performed with a rocking motion. In certain embodiments, the rocking is, is about, or is at least 25 RPM, 50 RPM, 100 RPM, 150 RPM, 200 RPM, 250 RPM, 300 RPM, 350 RPM, 400 RPM, 450 RPM, or 500 RPM. In some embodiments, the rocking is or is about 250 RPM. In some embodiments, the contact, treatment, and/or incubation with the agent, e.g., N-glycosidase, is performed under stationary conditions. In some embodiments, the cells are briefly mixed and/or vortexed e.g., for, for about, or for less than 30, 15, 10, 5, 2, or 1 seconds, during the contact, treatment, and/or incubation with the agent. In some embodiments, the cells are mixed or vortexed once, twice, three times, four times, five times, six times, seven times, eight times, nine times, ten times, or more than ten times during the contacting, incubation, and/or treatment.

In some embodiments, the composition of cells, e.g. test cell composition, is contacted, treated, and/or incubated with the agent, such as N-glycosidase, e.g. PNGase F, at a temperature less than 10° C. In some embodiments, the temperature is between 10° C. and 45° C., or between 24° C. and 40° C., or between 35° C. and 39° C. In some embodiments, the temperature is at least or at least about or is or is about 10° C., 15° C., 20° C., 24° C., 25° C., 26° C., 27° C., 28° C., about 29° C., 30° C., 31° C., 32° C., 33° C., 34° C., 35° C., 36° C., 37° C., 38° C., 39° C., or 40° C., or any range between any of the foregoing. In certain embodiments, a composition of cells is contacted, treated, or incubated with an agent that is or includes a PNGase F at a temperature of about 37° C.

In particular embodiments, a composition of cells is contacted, treated, or incubated with an agent, such as an N-glycosidase, e.g. PNGase F, and at least 70%, at least 75%, at least 80%, at least 85%, at least 90%, at least 95%, at least 97%, at least 98%, at least 99% or at least 99.9% of the surface exposed N-glycans are removed from the cells after an incubation performed at a temperature between 10° C. and 45° C., or between 24° C. and 40° C., or between 35° C. and 39° C., such as at least or at least about or is or is about 10° C., 15° C., 20° C., 24° C., 25° C., 26° C., 27° C., 28° C., about 29° C., 30° C., 31° C., 32° C., 33° C., 34° C., 35° C., 36° C., 37° C., 38° C., 39° C., or 40° C., or any range between any of the foregoing In certain embodiments, the composition of cells is incubated with an agent that is or includes a PNGase F at a temperature of between 10° C. and 45° C., or between 24° C. and 40° C., or between 35° C. and 39° C., such as at least or at least about or is or is about 10° C., 15° C., 20° C., 24° C., 25° C., 26° C., 27° C., 28° C., about 29° C., 30° C., 31° C., 32° C., 33° C., 34° C., 35° C., 36° C., 37° C., 38° C., 39° C., or 40° C. or any range between any of the foregoing, and at least 85%, at least 90%, at least 95%, or at least 99% of the surface exposed N-glycans are removed from the cells.

In some embodiments, a composition of cells is incubated with an agent, such as an N-glycosidase, e.g. PNGase F to remove N-glycans from the surface of the cells under conditions that do not damage or kill the cells. In some embodiments, the incubation is at a temperature of between 10° C. and 45° C., or between 24° C. and 40° C., or between 35° C. and 39° C., such as at least or at least about or is or is about 10° C., 15° C., 20° C., 24° C., 25° C., 26° C., 27° C., 28° C., about 29° C., 30° C., 31° C., 32° C., 33° C., 34° C., 35° C., 36° C., 37° C., 38° C., 39° C., or 40° C. or any range between any of the foregoing, and less than about 20%, about 15%, about 10%, about 5%, about 1%, about 0.5%, about 0.1%, about 0.05%, about 0.01%, about 0.001%, or about 0.0001% of the cells in the composition die, and/or initiate or undergo apoptosis or necrosis during the incubation.

In some embodiments, a composition of cells is incubated, treated, and or contacted with a PNGase F and surface expressed N-glycans are released, removed, or detached from the surface of the cells. In certain embodiments, the cell composition is incubated at or at about 37° C. for about 30 minutes, for about 60 minutes, or for an amount of time between 30 minutes and 60 minutes. In some embodiments, the incubation is performed with rocking at or at about 250 RPM. In some embodiments, the PNGase F contains a fusion domain. In certain embodiment, the fusion domain is a C-terminal His tag. In particular embodiments, the PNGase F is a preparation that is at least 95% pure and/or is a preparation with less than 5% non-PNGase F protein contaminants. In some embodiments, the PNGase F exhibits deglycosylation activity to release N-glycans from a native or non-denatured protein after incubation for 30-60 minutes at a temperature of 37°±2° C. In some embodiments, a composition of between $1 \times 10^6$ cells and $5 \times 10^6$ cells or between $1 \times 10^6$ cells and $2.5 \times 10^6$ cells is treated, contacted, or incubated with an agent that is or includes a PNGase F.

3. Removal of Cells

In some embodiments, the conditions, including incubating the cells with an agent that removes, released, and or detaches glycans, e.g., N-glycans from proteins expressed on the surface of the cells, results in release of glycans into the solution or the media where the treatment, incubation, and/or the contacting is performed. In certain embodiments, the cells of the composition are intact after the incubation, e.g., the cells are not ruptured, lysed, dying, and/or dead. In particular embodiments, the cells are removed from the media or solution after the incubation is performed. In particular embodiments, the cells are removed from the media or solution in a manner that does not rupture, lyse, and/or kill the cells. In some embodiments cells are removed by centrifugation, e.g., a low speed and/or low g centrifugation, and the supernatant is removed from the pellet that contains the cells. In particular embodiments, the supernatant contains, the glycans, e.g., N-glycans, that were removed from the surface of the cells during the treatment, incubation, or contacting.

In particular embodiments, the cells are removed from a sample, solution, or media that contains released surface glycans. In certain embodiments, the glycans are removed and/or separated from the media or solution. In some embodiments, the solution or media is evaporated. In particular embodiments, the solution or media is evaporated by vacuum centrifugation, e.g., with a speedvac. In particular embodiments, the glycans are removed and/or separated from the media or solution and are then resuspended. In some embodiments, the glycans may be resuspended in a volume of a buffer or solution. In some embodiments, the buffer or solution is suitable for storage. In certain embodiments, the buffer is suitable for use with a technique for the detection, identification, and/or detection of the glycans. In certain embodiments, the buffer or solution is suitable for a chemical reaction, e.g., a derivation reaction such as the addition of a detectable label.

B. Detecting Glycans

In some embodiments, after the incubation in accord with the provided methods, the glycans, e.g. N-glycans, that are attached to proteins expressed and/or exposed on the surface of the cells are released, removed, and/or detached into a media and or a solution. In certain embodiments, at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-five, at least thirty, at least thirty-five, at least forty, at least forty-five, at least fifty, at least fifty-five, at least sixty, at least sixty-five, at least seventy, at least seventy-five, at least eighty, at least eighty-five, at least ninety, at least ninety-five, at least 100, at least 125, at least 150, at least 175, at least 200, at least 225, at least 250, at least 300, at least 350, at least 400, at least 450, or at least 500 or greater species of glycans, e.g. N-glycans, are into the media or solution. In particular embodiments, the species of glycans, e.g. N-glycans, are detectable species of glycan. In some embodiments, the detectable species are N-glycans that can be detected, identified, measured, and/or quantified within the sample or from a preparation that is produced, generated, prepared, and/or derived from the sample.

Provided herein are methods for generating a high resolution surface N-glycan map of a cell composition. In some embodiments, the methods include the steps of detecting N-glycans that have been removed, released, and/or detached from the cell surface, e.g., from glycoproteins exposed at the cell surface. In particular embodiments, the detection of the N-glycans includes identifying and/or quantifying the N-glycans, for example by mass spectrometry (MS) or high performance liquid chromatography (HPLC) to produce the high resolution surface N-glycan expression profile. In certain embodiments, the methods provided herein include steps for washing, cleaning, and or purifying a sample of released N-glycans. In certain embodiments, the methods provided herein include steps for derivatizing the N-glycans, for example to increase or enhance detection of the N-glycans.

1. Derivation and Purification

In certain embodiments, glycans, e.g. N-glycans, are modified to improve and/or enhance the detection of the glycans. In many instances, glycans may not be readily detectable due to the absence of a strong chromophore or fluorophore or active moiety that is detectable by liquid chromatography and/or mass spectrometry. In some embodiments, the absorbance and fluorescence response of a glycan may be relatively weak or below a threshold for detection. In some embodiments, one tactic to maximize the sensitivity of an assay is to convert the compound of interest, i.e., the glycan, into a derivative that exhibits a better response for the particular detection method being utilized. In certain embodiments, the derivatizing agent affects or influences the ultimate sensitivity and accuracy of an analysis by maximizing the sensitivity, yield and/or stability of the derivatized molecules. Thus, in some embodiments, the glycans (e.g., N-glycans) that have been released from cellular surfaces are derivatized prior to any procedures for analysis or detection.

In some embodiments, the glycans are derivatized prior to an analysis by HPLC and/or mass spectrometry. In some embodiments, the sensitivity of the detection of N-glycans by existing techniques, e.g., high performance liquid chromatography (HPLC) and/or optical or mass spectrometric (MS) detection, can be improved and/or enhanced by a derivation step.

In some embodiments, a glycan, e.g., an N-glycan, is derivatized to allow for or improve detection by mass spectrometry. In certain embodiments, the glycan is derivatized to allow for the glycan to more easily accept a charge. In certain embodiments, a glycan and/or a derivatized glycan that is capable of accepting charge is detectable by a mass spectrometer. In some embodiments, the glycan is derivatized by adding an amino group, e.g., a tertiary amino group.

In some embodiments, the derivatization is or includes adding a detectable label to the glycans, e.g., N-glycans. In some embodiments, the addition is a covalent attachment. In certain embodiments, the attached detectable label increases signal and/or reduce background noise during the detection of the N-glycans as compared to detection of N-glycans that do not contain an attached detectable label. In certain embodiments, any of a variety of detectable labels can be used in accordance with the present disclosure, including but not limited to, fluorescent labels, radiolabels and/or chemiluminescent labels. In certain embodiments, the detectable label is a fluorescence label. In certain embodiments, attachment, e.g., covalent attachment, of the fluorescence label does not alter migration of the N-glycan in a column, e.g., a column suitable for HPLC. In particular embodiments, the label is a fluorescence label and allows for the glycan to more easily accept a charge as compared to an unlabeled glycan.

In some embodiments, released glycans can be analyzed by mass spectrometry, e.g., MALDI MS or ESI-MS-MS, directly without any derivation and/or chemical tagging. In some embodiments, this label-free approach is suitable for qualitative analysis for glycans. However, in some embodiments, the label-free approach is not as well suited for relative quantitation due to the fact that glycans from a single protein sample can be very heterogeneous in that the ionization efficiency is not the same among them. Therefore, in some embodiments, a single analysis platform that can perform both quantitative and qualitative analysis is used, for example, to determine the profile of surface N-glycan expression. A fluorescent detector only detects the dye itself, the so fluorescent response from various glycans can be used for relative quantitation. In some embodiments, a derivatizing or labeling reagent is used for an analytical procedure.

In some embodiments, the derivatization of the N-glycans is performed by a standard technique in the art. A large number of N-glycan derivatization techniques have been described and are reviewed in Ruhaak et al., Analytical and Bioanalytical Chemistry 397(8): 3457-3481 (2010). In some embodiments, the derivatization is performed by a chemical reaction that includes two or more reaction steps. In some embodiments, derivatization is performed by reaction reductive amination, permethylation, Michael addition, or hydrazide labeling. In certain embodiments, various compounds which provide the required functional group for the labeling reaction can be used. In certain embodiments, the derivatization is performed by a chemical reaction with a single reaction step. Labeling agents that add a label to a glycan by Chemical reaction with a single reaction step that are suitable for derivatization and/or covalently attaching a detectable label to an N-glycan includes agents that contain a functional group that rapidly reacts with amines (such as an isocyanate, or succidimidylcarbamate). Such labeling agents and fluorescence labels are described in U.S. Pat. App. No: US 20140242709.

In certain embodiments, the N-glycans are labeled by reductive amination. In this reaction, a label containing a primary amine group reacts in a condensation reaction with the aldehyde group of the glycan, resulting in an imine or Schiff base, which is reduced by a reducing agent to yield a secondary amine. In some embodiments, the reaction is performed in dimethyl sulfoxide containing acetic acid, tetrahydrofuran, or methanol. In some embodiments, reductive amination results in the stoichiometric attachment of one label per N-glycan allowing a direct quantitation based on fluorescence or UV-absorbance intensity.

Various labels have been used for the reductive amination of glycans. In some embodiments, fluorescent label that is or includes 2-aminobenzamide (2-AB), 2-aminobenzoic acid (2-AA), 2-aminopyridine (PA), 2-Aminoacridone (AMAC), 2-aminonaphthalene trisulfonic acid (ANTS), and 1-aminopyrene-3,6,8-trisulfonic acid (APTS), 3-(Acetylamino)-6-aminoacridin (AA-Ac), 6-Aminoquinoline (6-AQ), 7-Aminomethyl-coumarin (AMC), 2-Amino (6-amido-biotinyl) pyridine (BAP), 9-Fluorenylmethoxycarbonyl (FMOC)-hydrazide, 1,2-Diamino-4,5-methylenedioxy-benzene (DMB), or o-Phenylenediamine (OPD) is added to the glycans.

In particular embodiments, the N-glycans are labeled with a commercially available label. Labeling kits are available for the tags 2-AB, 2-AA, and PA (Ludger) as well as for labeling with APTS (Beckmancoulter) and ANTS (Prozyme). In some embodiments, the labeling agent and/or the fluorescence label is RapiFluor-MS (Waters Technologies Corporation).

In some embodiments, the labeling agent contains a fluorescent moiety, and a functional group that rapidly reacts with amines (such as an isocyanate, or succidimidylcarbamate). In some embodiments, the labeling agent contains one or more of a tertiary amino group or other MS active atom, a fluorescent moiety, and a functional group that rapidly reacts with amines (such as an isocyanate, or succidimidylcarbamate).

In particular embodiments, the labeling agent contains a fluorescent moiety that is or includes phanquinones or benzooxadiazoles. In some embodiments, the labeling reagent contains a fluorescent moiety that is a coumarin. Suitable examples of coumarins include, but are not limited to, coumarin 7 (3-(2,-Benzimidazolyl)-7-N,N-diethylaminocoumariii), Nile Red derivative, Coumarin 4 (7-Hydroxy-4-metbylcoumarin); Coumarin 120 (7-Amino-4-methyicoumarin); Coumarin 2 (7-Amino-4 methyl coumarin); Coumarin 466 (7-Diethylaminocoumarin); Coumarin 47 (7-Diethylamino-4-methylcoumarin); Coumarin 6H (2,3,5, 6-1H,4H-Tetrahydroquinolizino-[9,9a, 1-gh]coumarin); Coumarin 152A (7-Diethylamino-4-trifluormethylcoumarin); Coumarin 152 (7-Diniethyiamino-4-trifiuomiethyl-coumarin); Coumarin 151 (7-Amino-4-ti-ifluormethylcoumarin); Coumarin 6H (2,3,5,6-1H,4H-Tetrahydroquinolizino-[9, 9a, 1-gh]coumarin); Coumarin 307 (7-Ethylamino-6-methyl-4-trifluormethylcoumarin); Coumarin 500 (7-Ethylamino-4-trifluormethylcoumarin); Coumarin 314 (2,3,5,6-1H,4H-Tetrahydro-9-carboethoxy-quinolizino-[9,9a, 1-gh]coumarin); Coumarin 510 (2,3,5,6-U-4H-Tetrahydro-9-(3-pyridyi)-quinolizino-[9,9a, gh] coumarin); Coumarin 30 (3-2'-N-Methylbenzimidazolyl)-7-N, N-diethylaminocoumarin); Coumarin 552 (N-Methyl-4-trifiuormethylpiperidmo-3,2-g]-coumarin); Coumarin 6 (3-(2'-Benzothiazolyl)-7-diethylaminocoumarin).

In some embodiments, the labeling agent contains a fluorescent moiety that is a rhodamine. Suitable rhodamines include, but are not limited to: Rhodamine 110 (o-(6-Amino-3-imino-3H-xanthen-9-yl)-benzoic acid); Rhodamine 19 (Benzoic Acid, 2-[6-(ethylamino)-3-(ethylimino)-2,7-dimethyl-3H-xanthen-9-yl].perchlorate); Rhodamine 6G (Benzoic Acid,2-[6-(ethylamino)-3-(ethylimino)-2,7-dimethyl-3H-xanthen-9-yl]-ethylester,monohydrochloride); Rhodamine B (2-[6-(Diethylamino)-3-(diethylimino)-3H-xanthen-9-yl]benzoic acid). In some embodiments, the fluorescent moiety is a fluorescein. Fluorsceins may include, but are not limited to, Uranin (Disodium Fluorescein); and Fluorescein 27 (2,7-Dichloro fluorescein).

In certain embodiments, the labeling agent includes a fluorescent moiety that is a phenyl-substituted oxazol or a furan. In some embodiments, the fluorescent moiety is a PPO (2,5-Diphenyloxazoi); alpha-NPO (2-(1-Naphthyl)-5-phenyloxazol); BBO (2,5-Bis-(4-biphenylyl)-oxazol); and POPOP (1,4-Di[2-(5-phenyloxazolyl)]benzene). In certain embodiments, the fluorescent moieties include quaterphenyls. In particular embodiments, quaterphenyls include TMQ (3,3',2',3'''-Tetramethyl-p-quaterphenyl); BMQ (2,2'''-Dimethyl-p-quaterphenyl); DMQ (2-Methyl-5-t-butyi-p-quaterphenyl); PQP (p-Quaterphenyl); Polyphenyl 1 (p-Quaterphenyl-4-4'''-disulfonic acid Disodium salt); Polyphenyl 2 (p-Quaterphenyl-4-4''-disuifonicacid Dipotassium. salt; BiBuQ (4,4'''-Bis-(2-butyloctyloxy)-quaterphenyl); BM-Terphenyl (2,2''-Dimethyl-p-terphenyl); and FTP (p-Terphenyl). In some embodiments, the fluorescent moiety is a azaquinolone or carbostyryl, including but not limited to Carbostyryl 7 (7-Ammo-4-methylcarbostyryl); Carbostyryl 3 (7-Dimethylamino-4-methylquinolon-2); and Quinolon 390 (7-Dimethylamino-1-methyl-4-methoxy-8-azaqumolone-2). In some embodiments, the fluorescent moiety is a benzoxazole, benofurans, or benzothiazoles, where examples include: DASBTI (2-(p~Dimethylamiiiostyrj)-benzothiazolylethyl Iodide); Coumarin 6 (3-(2'-Benzothiazolyl)-7-dirnethylaminocournarin); Styryl 9M (2-(6-(4-Dimethylaminophenyl)-2,4-neopent rlene-1,3,5-hexatrienyl)-3-methyi-benzothiazoiium Perchlorate); Styryl 15 (2-(6-(9-(2, 6,7-Tetrahydro-1H,5H-benzo(ij)-chinolizmium))-2,4-neopentyiene-1,3,5-hexatrienyl)-3-methyibenzothiazolium Perchlorate); Styryl 14 (2-(8-(4-p-DimethyiammophenylV methyibenzothiazoiium Perchlorate); Styryl 20 (2-(8-(9-(2, 3,6,7-Tetrahydro-1H,5H-benzo(i j)-chinolizinium))-2,4-neopentylene-1,3,5,7-octatraenyl)-3-methylbenzothiazo-lium Perchlorate); Furan 1 (Benzofuran,2,2'-[1,1'-biphenyl]-4,4'-diyl-bis-tetrasulfonic acid (tetrasodium salt)); and PBBO (2-(4-Biphenylyl)~6-phenylbenzoxazoi~1,3).

In some embodiments, the fluorescent moiety is a substituted stilbene. Examples of substituted stilbenes include but are not limited to DPS (4,4'-Diphenylstilbene); Stilbene 1 ([1,1'-Biphenyl]-4-sulfonic acid, 4',4''-1; 2-ethene-diylbis-, dipotassium salt); and Stilbene 3 (2,2'-([1,1'-Biphenyl]-4,4'-diyldi-2,1ethenediyl)-bis-benzenesulfonic acid disodium salt). In some embodiments, the labeling agent contains a functional group that rapidly reacts with amines, a fluorescent moiety, and optionally one or more of a tertiary amino group or other MS active atom. In some embodiments, the functional group that rapidly reacts with amines is Fluorol 7GA (2-Butyl-6-(butylamino)-1H benz[de] isoquinoline-1,2 (2H)-dione. Sulforhodamine B (Ethanaminium, N-[(6-diethylamino)-9-(2,4-disulfophenyl)-3H-xanthen-3-ylidene]-N ethylhydroxid, inner salt, sodium salt); and Sulforhodamine 101 (8-(2,4-Disulfophenyl)-2,3,5,6,11,12,14,15-octahydro-1H,4H, 10H, 13H-diquinolizino [9,9a, 1-bc:9',9a', 1-hi]xanthenes).

In some embodiments, the fluorescent moiety in the labeling agent is a pyrromethene, e.g., Pyrromethene 546 (1,3,5,7,8-pentamethylpyrromethenedifluoroborate complex); Pyrromethene 556 (Disodium-1,3,5,7,8-pentamethylpyrromethene-2,6-disulfonate-difluoroborate complex);

(Disodium-1,3,5,7,8-pentamethylpyrromethene-2,6-disulfonate-difluoroborate Pyrromethene 567 (2,6-Diethyl-1,3,5,7,8-pentamethylpyrromethenedifluoroborate complex); Pyrromethene 580 (2,6-Di-n-butyl-1,3,5,7,8-pentamethylpyrromethenedifluoroborate complex); Pyrromethene 597 (2,6-Di-t-butyl-1,3,5,7,8-pen tamethylpyrromethenedifluoroborate complex); and Pyrromethene 650 (8-Cyano-1,2,3,5,6,7-hexamethylpyrromethenedifluoroborate complex).

In certain embodiments, the fluorescent moiety in the labeling agent is a pyrene-derivative, e.g., N-(1-pyrene) maleimide, or Pyranine (trisodium 8-hydroxypyrene-1,3,6-trisulfonate).

In certain embodiments, the labeling reagent comprises a tertiary amino group or other MS active atom, and a functional group that rapidly reacts with amines (such as an isocyanate, or succidimidylcarbamate). In certain embodiments, the amino group or MS active group gives increases detectability of the glycan by MS. In particular embodiments, the fluorescent moiety provides a good fluorescence signal; and the reactive functional group gives rapid tagging of desired biomolecules. In certain embodiments, a fluorescent label and or a labeling reagent includes a quinolinyl fluorophore. In particular embodiments, the fluorescent label comprises a carbamate tagging group. In some embodiments, the fluorescent label and/or the labeling comprises a basic tertiary amine. In particular embodiments, the fluorophore comprises the carbamate tagging group, the quinolone fluorophore, and the tertiary amine.

In some embodiments, the glycans are contacted, treated, and/or incubated with a derivatizing or labeling reagent, for, for about, or for at least 1 minute, 2 minutes, 3 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 1.5 hours, 2 hours, 3 hours, 4 hours, 5 hours, 6 hours, or between 1 minute and 1 hour, between 1 minute and 30 minutes, between 1 minute and 10 minutes, between 5 minutes and 15 minutes, or between 15 minutes and 30 minutes, between 1 hour and 6 hours, between 3 hours and 12 hours, or between 12 hours and 48 hours, inclusive. In some embodiments, the glycan are contacted and/or treated with the labeling and/or derivatizing reagent in the presence of a solvent, e.g., an organic solvent. In some embodiments, the solvent is hydrophilic. In certain embodiments, the solvent is an aprotic solvent. In particular embodiments, the solvent is an amide, e.g., an organic amide, a sulfonamide, a phosphoramide, or a formamide. In some embodiments, the labeling reagent and/or derivatizing reagent is contacted, treated, and/or incubated with the glycans in the presence of a solvent that is a formamide. In particular embodiments, the labeling reagent and/or derivatizing reagent is contacted, treated, and/or incubated with the glycans in the presence of a dimethylformamide.

In some embodiments, the glycans are contacted, treated, and/or incubated with the derivatizing or labeling reagent at a temperature. In some embodiments, the temperature is between 10° C. and 45° C., or between 24° C. and 37° C., or between 23° C. and 27° C. In some embodiments, the temperature is at least or at least about or is or is about 10° C., 15° C., 20° C., 24° C., 25° C., 26° C., 27° C., 28° C., 29° C., 30° C., 31° C., 32° C., or any range between any of the foregoing. In certain embodiments, the glycans are contacted, treated, or incubated with the derivatizing or labeling reagent at room temperature, e.g., between 23° C. and 27° C., between 24° C. and 26° C., or at or about 24° C., 25° C., or 26° C.

In some embodiments, the glycans are incubated, treated, and or contacted with a derivatizing or labeling reagent. In some embodiments, the derivatizing or labeling reagent is 2-aminobenzamide (2-AB), 2-aminobenzoic acid (2-AA), 2-aminopyridine (PA), 2-Aminoacridone (AMAC), 2-aminonaphthalene trisulfonic acid (ANTS), and 1-aminopyrene-3,6,8-trisulfonic acid (APTS), 3-(Acetylamino)-6-aminoacridin (AA-Ac), 6-Aminoquinoline (6-AQ), 7-Aminomethyl-coumarin (AMC), 2-Amino (6-amido-biotinyl) pyridine (BAP), 9-Fluorenylmethoxycarbonyl (FMOC)-hydrazide, 1,2-Diamino-4,5-methylenedioxy-benzene (DMB), or o-Phenylenediamine (OPD). In some embodiments, the glycans are incubated with the derivatizing or labeling reagent for or for about 5 minutes at room temperature, e.g., between 23° C. and 27° C., between 24° C. and 26° C., or at or about 24° C., 25° C., or 26° C.

In certain embodiments, the derivation and/or labeling reaction that occurs when the glycans are contacted, incubated, and/or treated with the derivation and/or labeling reagent is ended by quenching the reaction. In some embodiments, the reaction is quenched by adding a quenching agent. In particular embodiments, the derivation and/or labeling reaction is quenched prior to any analysis or quantification of the glycans, e.g., by chromatography and/or mass spectrometry techniques. Suitable agents to quench derivatization and labeling reactions are known, and in some aspects will depend on the specific derivatization or labeling reaction. In some aspects, the derivation and/or labeling reagent is 2-aminobenzamide (2-AB), 2-aminobenzoic acid (2-AA), 2-aminopyridine (PA), 2-Aminoacridone (AMAC), 2-aminonaphthalene trisulfonic acid (ANTS), and 1-aminopyrene-3,6,8-trisulfonic acid (APTS), 3-(Acetylamino)-6-aminoacridin (AA-Ac), 6-Aminoquinoline (6-AQ), 7-Aminomethyl-coumarin (AMC), 2-Amino (6-amido-biotinyl) pyridine (BAP), 9-Fluorenylmethoxycarbonyl (FMOC)-hydrazide, 1,2-Diamino-4,5-methylenedioxy-benzene (DMB), or o-Phenylenediamine (OPD), and the reaction is quenched by adding a nitrile, e.g., an organic nitrile. In some embodiments, the reaction is quenched with acetonitrile.

2. Purifying Glycans

In particular embodiments, a sample of the extracellular solution that contains the glycans is prepared for analysis, e.g., mass spectrometry analysis. In some embodiments, the sample of glycans, e.g. N-glycans, is purified prior to the analysis. In some embodiments, the purification includes any method capable of separating N-glycans from any entities which will or will potentially disrupt, hinder, and/or weaken the detection of the N-glycans. In some embodiments, the purification step is performed to remove the N-glycans from cellular debris, deglycosylated protein, PNGase F, buffer/formulation components, surfactants, labeling reaction byproducts, and/or excess labeling and/or derivatization reagents. In particular embodiments, the purification step is performed on labeled glycans, e.g. N-glycans, e.g., glycans with covalently attached detectable labels. In certain embodiments, the purification is performed by any suitable technique for purifying glycans, including but not limited to solid phase extraction (SPE), liquid-liquid extraction, gel filtration, paper chromatography, and precipitation.

In some embodiments, the purification is or includes a solid phase extraction (SPE). In particular embodiments, SPE is a sample preparation process by which compounds that are dissolved or suspended in a liquid mixture are separated from other compounds in the mixture, for example, according to their physical and/or chemical properties. In certain embodiments, chemical derivatization, e.g., addition of a detectable label, is performed prior to the analysis of the N-glycans, and SPE is performed to remove reagents used for the derivation from the N-glycans prior to detection. In certain embodiments, N-glycans that are dissolved or suspended in a liquid mixture are separated from other compounds in the mixture. In particular embodiments, the SPE is a process that utilizes the affinity of solutes, e.g., glycans, dissolved or suspended in a liquid (i.e., a mobile phase) for a solid through which the sample is passed (i.e., a stationary phase) to separate a mixture into desired and undesired components. In some embodiments, the desired components, i.e., glycans, are retained on the stationary phase. In particular embodiments, undesired components of the sample are retained on the stationary phase. In certain embodiments, the glycans, e.g., N-glycans, are retained on the stationary phase and the solution that passes through the stationary phase is discarded. In particular embodiments, the undesired components are retained on the stationary phase and the solution that passes through the stationary phase contains the glycans, e.g., N-glycans, and is collected. In some embodiments, the stationary phase retains the glycans, which are then removed from the stationary phase by contacting, passing, and/or rinsing the solid phase with an eluent.

In some embodiments, glycans, e.g. N-glycans, that have undergone derivation are purified prior to detection. In some embodiments, the purification is performed by solid phase extraction (SPE). In some embodiments, SPE is performed on glycans after the derivation process. In certain embodiments, salts, e.g., excess salts from the derivation reaction or reactions, are removed from the glycans, e.g. N-glycans, by SPE. In certain embodiments, the glycans, e.g. N-glycans, undergo SPE after a derivation reaction. In some embodiments, SPE is performed after a detectable label is added to the glycans, e.g. N-glycans, e.g., by way of a reductive amination reaction or hydrazide labeling. In some embodiments, SPE removes excess labeling reagent from the derivation reaction or reactions from the glycan sample.

In some embodiments, the solid phase of the SPE is or includes a cartridge. In certain embodiments, the solid phase retains, collects, and/or binds glycans contains a polyamide adsorbent that may be used to adsorb glycans from aqueous solutions. In some embodiments, solutions can be passed through these cartridges by using either gravity, vacuum, or positive pressure. In particular embodiments, the cartridge extracts glycans from other materials, e.g., salts, moieties, reagents, and/or cellular debris, according to a difference in hydrophobicity of the N-glycans and the other materials. In some embodiments, the SPE materials for preparation are C18 and charcoal, both of which have high selectivity for glycans.

In some embodiments, the SPE is performed with a commercially available kit. In certain embodiments, the SPE is performed according to the manufacturer's instructions. Suitable kits that are of include SPE of N-glycans include, but are not limited to GLYCOCLEAN H Cartridges (GKI-4025 ProZyme), ADVANCE BIO N-Glycan Deglycosylation cleanup cartridges (Agilent), Ludger Clean T1 cartridges (LC-T1-A6, Ludger), GlycoWorks 2-AB N-Glycan Kits (Waters), and GlycoWorks RapiFluor-MS N-Glycan Kit (Waters).

In some embodiments, the SPE is performed by a hydrophilic interaction liquid chromatography (HILIC) SPE process. In some embodiments, the SPE is performed by first conditioning the sorbent with water and then equilibrating it to high acetonitrile loading conditions. In certain embodiments, the N-glycan samples are diluted with acetonitrile and are loaded and washed free of the sample matrix using an acidic wash solvent. In some embodiments, the columns, tubes, cartridges, or wells for use with the SPE process are conditioned with water, e.g., distilled water. In some embodiments, the columns, tubes, cartridges, or wells are conditioned with an organic solvent, e.g., acetonitrile. In some embodiments, a sample or solution containing the glycans is loaded onto the column, tube, cartridge, or well. In particular embodiments, the columns, tubes, cartridges, or wells containing the glycans are washed and/or rinsed at least once, twice, three times, four times, five times, six times, seven times, eight times, nine times, or ten times. In particular embodiments, the columns, tubes, cartridges, or wells containing the glycans are washed and/or rinsed with a solution. In some embodiments, the solution is or includes water. In particular embodiments, the solution is or includes acetonitrile. In particular embodiments, the solution is or includes formic acid. In certain embodiments, the columns, tubes, cartridges, or wells are rinsed and/or washed in a solution that includes water, acetonitrile, and formic acid.

In some embodiments, the glycans are eluted from the columns, tubes, cartridges, or wells. In certain embodiments, the glycans are eluted with a solution that is or includes ammonium acetate. In particular embodiments, the glycans are eluted with a solution that is or includes acetonitrile. In particular embodiments, the glycans are eluted with a solution that includes ammonium acetate and acetonitrile. In particular embodiments, the glycans are eluted with a solution that contains, contains about, or contains at least 1 mM, 5 mM, 10 mM, 20 mM, 50 mM, 100 mM, 150 mM, 200 mM, 250 mM, 300 mM, 400 mM, 500 mM, or 1,000 mM ammonium acetate. In certain embodiments, the glycans are eluted with a solution that contains, contains about, or contains at least 0.1%, 0.5%, 1%, 2%, 3%, 4%, 5%, 6%, 7%, 8%, 9%, 10%, 15%, 20%, 25%, or 50% acetonitrile. In particular embodiments, the glycans are eluted with a solution that contains or contains about 200 mM ammonium acetate and 5% acetonitrile.

In some embodiments, the washing condition achieves optimal SPE selectivity by introducing electrostatic repulsion between the aminopropyl HILIC sorbent and reaction byproducts and by enhancing the solubility of the matrix components. In particular embodiments, the labeled, released glycans are next eluted from the HILIC sorbent. In certain embodiments, the SPE sorbent has a weakly basic surface, and the capacity for anion exchange, just as it has the capacity for cation repulsion, and so the labeled glycans are eluted with an eluent of significant ionic strength. Thus, in some embodiments, the elution buffer comprises a pH 7 solution of 200 mM ammonium acetate in 5% acetonitrile. In certain embodiments, upon their elution, the labeled glycans can be diluted with a mixture of organic solvents e.g., acetonitrile and dimethylformamide, and directly analyzed by UPLC or HPLC HILIC column chromatography using fluorescence and/or ESI-MS detection.

In some embodiments, the amount or concentration of glycans, e.g. N-glycans in a sample, solution, and/or media is adjusted. In particular embodiments, the amount or concentration of glycans, e.g. N-glycans in a sample, solution, and/or media is adjusted by evaporating the sample, solution, and/or media, and resuspending the glycans, e.g. N-glycans, in a solution to the desired concentration. In some embodiments, the volume of a sample, solution, and/or media that contains the glycans, e.g. N-glycans, is adjusted by evaporating the sample, solution, and/or media, and resuspending the glycans in a solution of the desired volume. In some embodiments, the sample, solution, and/or media is evaporated by vacuum centrifugation.

In particular embodiments, the sample, solution, and/or media containing glycans, e.g. N-glycans, is evaporated prior to a purification step, e.g., SPE. In some embodiments, the sample, solution, and/or media containing glycans, e.g. N-glycans, is evaporated by vacuum centrifugation prior to a purification step. In some embodiments, the sample, solution, and/or media containing glycans, e.g. N-glycans, is evaporated following the purification step. In particular embodiments, the sample, solution, and/or media containing glycans, e.g. N-glycans, is evaporated by vacuum centrifugation following a purification step. In certain embodiments, the sample, solution, and/or media containing glycans, e.g. N-glycans, is evaporated prior to detection, e.g., detection by HPLC and/or MS. In some embodiments, the sample, solution, and/or media containing glycan, e.g. N-glycans, is evaporated by vacuum centrifugation prior to detection. In some embodiments, the vacuum centrifugation allows for the sample containing glycans to alter or adjust volumes for different steps or procedures. For example, volume might be increased prior to purifying the N-glycans with SPE so that unwanted materials, e.g., cellular debris, does not clog the SPE column or cartridge. In such instances, the eluate containing the glycans may be vacuum centrifuged and resuspended in a smaller volume, for example for analysis with HPLC or mass spectrometry.

3. Profiling the Glycans

Provided are methods for assessing cell surface glycans, e.g., N-glycans, by determining the presence, absence, or level of the glycans present in a sample. In particular embodiments the sample contains glycans that have been released, removed, or detached from the surface of cells present in a cell composition, e.g., a test cell composition. In certain embodiments, a sample containing glycans, e.g., N-glycans, that have been released from the surface of cells are assessed and or analyzed to determine the presence, absence, or level of glycans present in the sample.

In some embodiments, isolated and/or released surface glycans may be analyzed or assessed by any known technique in the art that is suitable for the detection, analysis, and or isolation of glycans, e.g., N-glycans. For example, in certain embodiments, glycans are analyzed using one or more available methods described in Anumula, Anal. Biochem. 350(1):1, 2006; Klein et al., Anal. Biochem., 179:162, 1989; and/or Townsend, R. R. Carbohydrate Analysis High Performance Liquid Chromatography and Capillary Electrophoresis., Ed. Z. El Rassi, pp 181-209, 1995. For example, in some embodiments, glycans are characterized using one or more of chromatographic methods, electrophoretic methods, nuclear magnetic resonance methods, and combinations thereof. Exemplary such methods include, for example, NMR, mass spectrometry, liquid chromatography, 2-dimensional chromatography, SDS-PAGE, antibody staining, lectin staining, monosaccharide quantitation, capillary electrophoresis, fluorophore-assisted carbohydrate electrophoresis (FACE), micellar electrokinetic chromatography (MEKC), exoglycosidase or endoglycosidase treatments, and combinations thereof. Those of ordinary skill in the art will be aware of other methods that can be used to characterize glycans. In certain embodiments, isolated surface glycans are analyzed or assessed by a technique that is or includes liquid chromatography, fluorescence detection, and/or mass spectrometry.

a. Chromatography

In some embodiments, liquid chromatography (LC), including high performance liquid chromatography, is used to analyze glycans (e.g., N-glycans), that are present in the sample. Various forms of LC can be used to study glycans, including anion-exchange chromatography, reversed-phase HPLC, size-exclusion chromatography, high-performance anion-exchange chromatography, and normal phase (NP) chromatography, including NP-HPLC. Hydrophilic interaction chromatography (HILIC) is a variant of NP-HPLC that can be performed with partially aqueous mobile phases, permitting normal-phase separation of peptides, carbohydrates, nucleic acids, and many proteins. In some embodiments, glycans in a sample are detected by, or by methods that include, LC, e.g., HPLC or HILIC.

In certain embodiments, the liquid chromatography is a high performance liquid chromatography (HPLC), ultra-high performance liquid chromatography (UHPLC), or ultra-performance liquid chromatography (UPLC). In some embodiments, HPLC is distinguished from traditional ("low pressure") liquid chromatography because operational pressures are significantly higher, 50-350 bar (725-5070 psi), while ordinary liquid chromatography typically relies on the force of gravity to pass the mobile phase through the column. UHPLC operate at pressures of up to 1030 bar (15,000 psi).

In some embodiments, glycans in a sample are detected by, or by methods that include, HILIC. In some embodiments, HILIC is a form of HPLC that can be used in the methods described herein. HILIC separates analytes based on polar interactions between the analytes and the stationary phase (e.g., substrate). The polar analyte associates with and is retained by the polar stationary phase. Adsorption strengths increase with increase in analyte polarity, and the interaction between the polar analyte and the polar stationary phase (relative to the mobile phase) increases the elution time. Use of more polar solvents in the mobile phase will decrease the retention time of the analytes while more hydrophobic solvents tend to increase retention times. The elution order for HILIC is least polar to most polar, the opposite of that in reversed-phase HPLC. In some embodiments, HILIC can be performed on an HPLC system.

In particular embodiments, glycans are detected by or by methods that include HILIC. In some embodiments, various types of substrates can be used with HILIC, e.g., for column chromatography, including silica, amino, amide, cellulose, cyclodextrin and polystyrene substrates. Examples of useful substrates, e.g., that can be used in column chromatography, include but are not limited to: polySulfoethyl Aspartamide (e.g., from PolyLC), a sulfobetaine substrate, e.g., ZIC®-HILIC (e.g., from SeQuant), POROS® HS (e.g., from Applied Biosystems), POROS® S (e.g., from Applied Biosystems), PolyHydroethyl Aspartamide (e.g., from PolyLC), Zorbax 300 SCX (e.g., from Agilent), PolyGLYCOPLEX® (e.g., from PolyLC), Amide-80 (e.g., from Tosohaas), TSK GEL® Amide-80 (e.g., from Tosohaas), Polyhydroxyethyl A (e.g., from PolyLC), Glyco-Sep-N (e.g., from Oxford GlycoSciences), and Atlantis HILIC (e.g., from Waters). Preferred columns include polySulfoethyl Aspartamide and ZIC®-HILIC; the most preferred column being polySulfoethyl Aspartamide. Column that can be used in the disclosed methods include columns that utilize one or more of the following functional groups: carbamoyl groups, sulfopropyl groups, sulfoethyl groups (e.g., poly (2-sulfoethyl aspartamide)), hydroxyethyl groups (e.g., poly (2-hydroxyethyl aspartamide)) and aromatic sulfonic acid groups. Preferred functional groups include sulfoethyl groups such as poly (2-sulfoethyl aspartamide) and sulfopropyl groups such as $CH_2N(CH_3)_2CH_2CH_2CH_2SO_3$.

In some embodiments, the LC analyzed glycans are then further subjected to analysis by mass spectrometry. Examples of mass spectrometry that can be used to further analyze the glycans include ESI-MS, turbospray ionization mass spectrometry, nanospray ionization mass spectrometry, thermospray ionization mass spectrometry, sonic spray ionization mass spectrometry, SELDI-MS and MALDI-MS. For example, the methods described herein can be used to provide LC-evaluated glycans for on-line mass spectrometry (e.g., ESI-MS) and/or for off-line mass spectrometry (e.g., MALDI-MS) without further purification.

In certain embodiments, glycans are labeled with a chromophore or a fluorophore allow for sensitive detection in HILIC. In some embodiments, the most commonly used labels are PA, 2-AB, and 2-AA, but other tags such as 3-(acetylamino)-6-aminoacridine, or other tags such as tags containing a the quinolone fluorophore, and the tertiary amine are also useful. In particular embodiments, glycans that are labeled with tags containing a quinolone fluorophore and the tertiary amine are detected by or by methods that include HILIC. As most of these labels have hydrophobic characteristics, the derivatized glycans may show slightly less retention than native, unlabeled glycans. In some embodiments, fluorescence detection is performed using detectors equipped with a xenon lamp and both excitation and emission monochromators can be set to the optimal wavelengths of the chosen label to achieve high sensitivity.

b. Fluorescence Detection

In certain embodiments, fluorescence detection is coupled to a liquid chromatography and/or a mass spectrometry technique. In certain embodiments, the glylcan, e.g., an N-glycan, is attached, e.g., covalently attached, to a fluorescent label. In particular embodiments, the fluorescently labeled glycan, e.g., an N-glycan, is analyzed by fluorescence detection with liquid chromatography followed by analysis with mass spectrometry. In some embodiments, the combination of liquid chromatography, mass spectrometry, and fluorescent detection is an analytical platform that can be used for a comprehensive glycan analysis of a sample, e.g., a sample of N-glycans that were released or detached from the surface of cells.

In some embodiments, HPLC-fluorescence detection has a number of benefits, including high sensitivity, high selectivity, and repeatability. The most advanced fluorescence detectors feature a temperature-controlled cell to ensure stable analysis even if the ambient temperature fluctuates. These detectors also provide high levels of sensitivity and validation to support functions in a wide range of applications from conventional to ultra-fast LC analysis. In certain embodiments, the glycans are analyzed with a fluorescence detector that features a temperature-controlled cell.

In some embodiments, fluorescence labeling is used with liquid chromatography and/or mass spectrometry to detect glycans. Many organic molecules, e.g., glycans, exhibit strong UV absorbance at wavelengths less than 210 nm, thus allowing a detector set at 200 nm to act somewhat as a "universal" detector. Fluorescence is much less common than UV absorbance. Thus, in some embodiments, given a sample containing an amount of unwanted material or impurities, fluorescence detection would only measure tagged or labeled molecules, thus overcoming issues of background or selectivity. In some embodiments, fluorescence detectors can enhance the selectivity of the glycan analysis.

In some embodiments, a sample of glycans, e.g., N-glycans released from the surface of cells, is labeled with a fluorescent label, and more species of glycans are detected than are detected than with a sample of glycans are not labeled. In some embodiments, a sample of glycans is labeled with a fluorescent label, and at least 10%, at least 20%, at least 30% at least 40%, at least 50%, at least 60%, at least 70%, at least 80%, at least 90%, at least 95%, at least 100%, or is at least 1-fold, at least 2-fold, at least 3-fold, at least 4-fold, at least 5-fold, or at least 10-fold more species of glycans in the sample are detected than with a sample of glycans that are not labeled.

In certain embodiments, a sample of glycans, e.g., N-glycans released from the surface of cells, is labeled with a fluorescent label, and the glycans are detected with a greater sensitivity than the glycans are not labeled. In certain embodiments, the sensitivity for detection is increased by at least 10%, at least 20%, at least 30% at least 40%, at least 50%, at least 60%, at least 70%, at least 80%, at least 90%, at least 95%, at least 100%, or is at least 1-fold, at least 2-fold, at least 3-fold, at least 4-fold, at least 5-fold, at least 10-fold, or at least 100-fold when the N-glycans are labeled as compared to when the N-glycans are not labeled.

In some embodiments, glycans in a sample are selectively labeled with a fluorescent label, and the sample is assessed with liquid chromatography that is coupled with fluorescence detection. In some embodiments, the glycans are selectively labeled so that the only glycans contain the attached label in the sample. In certain embodiments, the glycans are selectively labeled so that glycans are labeled at least 2 times, 5 times, 10 times, 50 times, 100 times, 1,000 times, 2,000 times, 5,000 times, 10,000 times, 50,000 times, 100,000 times, 250,000 times, 500,000 times, 1,000,000 or greater that the portion of sample that are not glycans, e.g., impurities such as proteins.

c. Mass Spectrometry

In various embodiments, methods comprise subjecting a portion of a glycan mixture to analysis with a mass spectrometric technique. Mass spectrometry (MS), in its most simple definition, is the production and detection of ions separated according to their mass-to-charge (m/z) ratios. The detection of such ions results in a mass spectrum which is a plot of the relative abundance of the ions as a function of their m/z ratio. The two most widely-used MS ionization techniques for the analysis of glycans are Matrix-Assisted Laser Desorption/Ionization (MALDI) and Electrospray Ionization (ESI); in both free glycans are typically detected as metal (usually sodium) adducts in the positive ion mode, and as deprotonated or anion-adducted species in the negative-ion mode. Glycans may be detected in their protonated or deprotonated forms. Both MALDI and ESI are soft ionization techniques; i.e., the ionization process imparts little excess energy and thus generates few or no fragments for glycans so that the intact molecular ions can be easily observed. Nevertheless, prompt loss of labile groups, especially sialic acid and fucose, may occur and the extent of its occurrence should be assessed, particularly in quantitative studies. Both MALDI-MS and ESI-MS can be applied to obtain an overall glycan profile.

Methods of the present inventions can be performed with a wide variety of mass spectrometry instruments and techniques, including but not limited to, matrix assisted laser desorption/ionization mass spectrometry time of flight mass spectrometry (MALDI-TOF-MS), MALDI-TOF-TOF-MS, liquid chromatography with mass spectrometry (LC-MS), liquid chromatography with tandem mass spectrometry (LC-MS/MS), or by direct infusion electrospray ionization mass spectrometry (ESI-MS). In some embodiments, the N-glycans are detected by, or by a method that includes, analysis with MALDI-MS or ESI-MS.

In particular embodiments, N-glycans are detected with a high resolution mass spectrometer. In some embodiments, the resolution of the mass spectrometer is greater than 50 amu, 25 amu, 10 amu, 5 amu, 1 amu, 0.5 amu, or 0.1 amu. In certain embodiments, the resolution of the mass spectrometer is greater than 1 amu.

In some embodiments, mass spectrometry is performed without prior separation by liquid chromatography. In particular embodiments, the glycans are detected without prior separation by liquid chromatography by surface enhanced laser desorption ionization mass spectrometry (SELDI-MS) or matrix assisted laser desorption/ionization mass spectrometry (MALDI-MS). In some embodiments, the glycans are detected without prior separation by liquid chromatography by MALDI-MS.

MALDI is an ionization technique that uses a laser energy absorbing matrix to create ions from large molecules with minimal fragmentation. It has been applied to the analysis of biomolecules (biopolymers such as DNA, proteins, peptides and sugars) and large organic molecules (such as polymers, dendrimers and other macromolecules), which tend to be fragile and fragment when ionized by more conventional ionization methods. It is similar in character to electrospray ionization (ESI) in that both techniques are relatively soft (low fragmentation) ways of obtaining ions of large molecules in the gas phase, though MALDI typically produces far fewer multiply charged ions. In certain embodiments, glycans in a sample, e.g., a sample of surface expressed glycans, are detected by MALDI-MS. In some embodiments, the glycans are N-glycans.

In certain embodiments, liquid chromatography-mass spectrometry (LC-MS) is an analytical chemistry technique that combines the physical separation capabilities of liquid chromatography (or HPLC) with the mass analysis capabilities of mass spectrometry (MS). In some embodiments, coupled chromatography-MS (LC-MS) systems are employed because the individual capabilities of each technique are enhanced synergistically. While liquid chromatography separates mixtures with multiple components, mass spectrometry provides structural identity of the individual components with high molecular specificity and detection sensitivity. In some embodiments, glycans are detected by liquid chromatography, e.g., HILIC HPLC, followed by mass spectrometry. In some embodiments, the mass spectrometry is electrospray ionization mass spectrometry (ESI-MS), turbospray ionization mass spectrometry, nanospray ionization mass spectrometry, thermospray ionization mass spectrometry, sonic spray ionization mass spectrometry.

In certain embodiments, the glycans, e.g., N-glycans, are detected by ESI-MS after sorting by liquid chromatography. In such embodiments, analysis by liquid chromatography, e.g., with fluorescence detection, provides information of the relative abundance of an N-glycan species, e.g., by calculating the area under the curve corresponding to the individual glycan, and expressing it as a ratio or a percentage of the total areas of all the curve corresponding to glycans. In certain embodiments, standards can be used to determine to amount of the glycan present in the sample. In certain embodiments, the LC, e.g., HILIC, is on-line with the mass spectrometer. In some embodiments, the mass spectrometer measures the precise mass of the N-glycans, allowing for the identification of the glycans that correspond to the peaks detected by the LC. In some embodiments, glycans, e.g., N-glycans, are assessed for the presence, absence, or amount by LC-MS.

In particular embodiments, the glycans, e.g., N-glycans, that have been removed from a cellular surface are detected with by LC-ESI-MS. ESI is a technique used in mass spectrometry to produce ions using an electrospray in which a high voltage is applied to a liquid to create an aerosol. In some embodiments, ESI is useful in producing ions from macromolecules by overcoming the propensity of these molecules to fragment when ionized. ESI is different from other atmospheric pressure ionization processes (e.g. MALDI) since it may produce multiple charged ions, effectively extending the mass range of the analyzer to accommodate the kDa-MDa orders of magnitude observed in proteins and their associated polypeptide fragments.

In certain embodiments, the mass spectrometry is tandem mass spectrometry (tandem MS or MS/MS). In particular embodiments, MALDI-TOF-MS, MALDI-TOF-TOF-MS, LC-MS, and/or ESI-MS techniques are performed with tandem MS and/or are performed with a tandem MS technique. In particular embodiments, tandem MS involves more than one-step of mass selection or analysis, and fragmentation is usually induced between the steps. In some embodiments, tandem mass spectrometry is used and/or employed for glycan identification, quantification, and/or detection. The first mass analyzer, i.e., first stage MS, isolates ions of a particular m/z value that represent a single species of glycan among many introduced into and then emerging from the ion source. Those ions, e.g., ionized glycan particles, are then fragmented, e.g., accelerated into a collision cell containing an inert gas such as argon to induce ion fragmentation. This process is designated "collisionally induced dissociation" (CID) or "collisionally activated dissociation" (CAD). The m/z values of fragment ions, e.g., ionized glycan fragments, are then measured in a $2^{nd}$ mass analyzer, i.e., second stage MS, to obtain structural information. In particular embodiments, glycans are identified, quantified, and/or detected by tandem MS.

There are several types of tandem mass spectrometers, including triple stage quadrupoles (TSQ), 3D and linear ion traps, quadrupole/time-of-flight (QTOF) hybrid instruments, quadrupole-linear ion trap hybrid instruments (QTRAP), and time-of-flight-time-of-flight (TOF/TOF) instruments. With 3D or linear quadrupole ion traps, tandem MS can also be performed in a single mass analyzer over time and in these instruments this process may be iterated more than once to yield $MS^n$ spectra. These instruments achieve fragmentation by resonance excitation, which induces collisions with the trap bath gas (helium) of sufficiently high energy to induce fragmentation. The other instruments mentioned above employ CID in a collision cell. Other methods that can be used to fragment molecules for tandem MS include electron capture dissociation (ECD), electron transfer dissociation (ETD), infrared multiphoton dissociation (IRMPD) and blackbody infrared radiative dissociation (BIRD) (9).

In some embodiments, particles are fragmented between the first stage and the second stage MS. In particular embodiments, the fragmentation is in-source fragmentation, collision-induced fragmentation, collision-induced dissociation, election capture dissociation, electron transfer dissociation, negative electron transfer dissociation, electron-detachment dissociation, charge transfer dissociation, photodissociation, infrared multiphoton dissociation, blackbody infrared radiative dissociation, surface induced dissociation.

In particular embodiments, the MS is tandem MALDI-MS (MALDI-MS/MS) or tandem ESI-MS (ESI-MS/MS). In certain embodiments, the N-glycans are quantified, detected, and/or identified by, or by a method that includes, analysis with tandem MALDI-MS or tandem ESI-MS.

4. Profiles and Maps

Provided herein are methods for assessing and/or analyzing a sample containing glycans, e.g., a sample containing released surface N-glycans from a cell composition, e.g. test cell composition. In particular embodiments, the sample is assessed or analyzed by determining the presence, absence, level, relative abundance, and/or amount of one or more glycans, e.g. N-glycan. In some embodiments, the one or more glycans, e.g. N-glycans, are part of a cell surface profile of glycans detected in the sample. In some embodiments, the cell surface profile indicates the presence, absence, level, relative abundance and/or amount of one or more different species of N-glycans. In some aspects, the one or more different species can include any as set forth in Table E1 or a subset thereof. In some embodiments, the number of species of different glycans is greater than or greater than about 5, 10, 20, 30, 40, 50, 60, 70, 80, 90, 100, 150, 200, 300, 400, 500 or more different species.

In some aspects, the one or more different species of N-glycans include, for example, high mannose N-glycans, bisected and Sialyl Lewis$^x$ N-glycans, and/or N-acetyl lactosamine containing N-glycans.

In some aspects, the one or more different species of N-glycans include, for example, a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

In some embodiments, the sample is assessed for the presence, absence, level, relative abundance and/or amount of a target glycan or one or more target glycans. In certain embodiments, least 10, at least 20, at least 25, at least 30, at least 40, at least 50, at least 60, at least 70, at least 80, at least 90, at least 100, at least 125, at least 150, at least 175, at least 200, at least 225, at least 250, at least 300, at least 400, or more than 500 different glycan species are assessed or analyzed, e.g., for the presence, absence, relative level, or amount of the glycans.

In some embodiments, the target glycan or glycans are those whose presence, absence, level, relative abundance and/or amount on the cell surface is associated with one or more functional and/or phenotypic activity. In some cases, the target glycan or glycans is one that is associated with or that may affect or impact or alter an activity form among masking of a cell surface marker, a metabolic activity, differentiation state, proliferative or expansion capacity, activation state, cytolytic activity, signaling activity, an adhesion property, or a homing property.

In some aspects, the one or more different species can include any as set forth in Table E1 or a subset thereof. In some embodiments, the number of species of different glycans is greater than or greater than about 5, 10, 20, 30, 40, 50, 60, 70, 80, 90, 100, 150, 200, 300, 400, 500 or more different species.

In some aspects, the one or more different species of N-glycans include, for example, high mannose N-glycans, bisected and Sialyl Lewis' N-glycans, and/or N-acetyl lactosamine containing N-glycans.

In some aspects, the one or more different species of N-glycans include, for example, a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues. In some embodiments, the methods provided herein allow for detection of relative levels of individual glycan species within a population of glycans. For example, in some embodiments, the area under each peak of a liquid chromatograph can be measured and expressed as a percentage of the total. Such an analysis provides a relative percent amount of each glycan species within a population of surface expressed glycans.

In certain embodiments, methods provided herein facilitate detection of glycans that are present at very low levels in the sample, e.g., a sample containing surface expressed N-glycans. In certain embodiments, it is possible to detect and/or quantify the levels of glycans that are present at levels less than about 10%, 5%, 4%, 3%, 2%, 1.5%, 1%, 0.75%, 0.5%, 0.25%, 0.1%, 0.075%, 0.05%, 0.025%, 0.01%, 0.001%, 0.0001%, or 0.00001% within a population of glycans. In some embodiments, it is possible to detect and/or optionally quantify the levels of glycans that make up between 0.1% and 10%, between 0.0001% and 0.1%, between 0.1% and 1%, between 1% and 5%, between 0.00001% and 1%, between 0.1% and 2%, or between 0.1% and 1% of the total glycans in the sample.

In some embodiments, methods described herein allow for detection of particular linkages that are present at low levels within a sample of surfaced expressed glycans, e.g., N-glycans. For example, in some embodiments, the present methods allow for detection of particular linkages that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, less than 0.01%, less than 0.001%, less than 0.0001%, or less than 0.00001% of population of surface expressed glycans.

In certain embodiments, the identity of individual glycans within a profile may be determined. Particular embodiments contemplate that the identities of individual glycan species may be readily identified, for example from the results of an analysis, e.g., by HPLC, UPLC, exoglycosidase sequencing and mass spectrometry (MALDI-MS, ESI-MS, ESI-MS/MS, LC-MS, LC-ESI-MS/MS). In some embodiments, the identity of one or more glycans may be determined through the use of a reference database. Several databases are available to assist with determining glycan identity and/or glycan structure based on information obtained from techniques including but not limited to HPLC, UPLC, exoglycosidase sequencing and mass spectrometry (MALDI-MS, ESI-MS, ESI-MS/MS, LC-MS, LC-ESI-MS/MS) data. In some embodiments, suitable databases include, but are not limited to, GlycoBase (glycobase.nibrtie/glycobase/show nibrtaction); Glycosciences(Glycosciences.de); UniCarbKB (unicarbkb.org); UniCarbDB (unicarb-db.biomedicine.gu.se); SugarBindDB (sugarbind.expasy.org), and Expasy (expasy.org/glycomics).

In particular embodiments, the methods provided herein allow for the analysis and/or assessment of surface glycans in a sample. In certain embodiments, the methods provided herein allow for the detection, identification, and or quantification of levels of cell surface glycans that are present in an amount of between about 0.1 fmol to about 1 mmol in a sample. In particular embodiments, a glycan that is present in a sample in an amount of at least 10 amol, at least 100 amol, at least 500 amol, at least 1 fmol, at least 5 fmol, or at least 10 fmol of a glycan species that is present in a sample of glycans can be detected, identified, and/or quantified by the methods provided herein.

C. Detecting Substances

In certain embodiments, the methods provided herein are used to detect a presence, absence, identity, or level of one or more substances, e.g., residual substances, that may be present in a cell composition and/or in a sample collected from a cell composition. In certain embodiments, the substance is any compound, component, material, or matter that is or includes one or more glycans. In particular embodiments, the substance is or is produced, generated, expressed, and/or synthesized by a living organism. In certain embodiments, the substance is or includes a nucleic acid, protein, and/or lipid moiety. In particular embodiments, the substance is or includes one or more proteins, e.g., glycoproteins.

In some embodiments, methods for detecting the presence, absence, identity, and/or level of one or more substances in a cell composition is or includes generating a surface N-glycan profile of from the cell composition and/or from a sample collected from the cell composition. In certain aspects, the presence of a substance, e.g., a residual substance, is indicated by the identification and/or detection of a glycan that exogenous to, is not native to, and/or is not produced by the cells in the cell composition, e.g., within the surface glycan profile.

In certain embodiments, the non-native and/or exogenous glycan is not native to the cells of the composition, e.g., the glycan is not generated, synthesized, and/or produced by the cell and/or is not attached or bound to a protein expressed and/or synthesized by any of the cells of the composition. In certain embodiments, a glycan that is native to a cell is a glycan that is synthesized by the cell. In some aspects, the glycan, e.g., N-glycan, biosynthesis occurs in the ER and the Golgi, and, in some aspects, includes the assembly oligosaccharides and transfer to amino acid residues, e.g., Asn, of proteins, such as secretory or membrane proteins, during translocation into the ER. In some embodiments, the glycan biosynthesis is or includes further processing, such as by glycosidases and glycosyltransferases in the lumen of the ER, and, in some aspects, continues in the Golgi. In certain embodiments, a glycan is non-native or exogenous to a cell if the glycan is not synthesized by and/or within the cell, e.g., at, near, or within the ER or Golgi.

In certain embodiments, the non-native and/or the exogenous glycan is not produced, expressed, or otherwise present on the surface and/or bound to proteins at the surface, of cells from the same kingdom, phylum, class, order, family, genus, and/or species as the cells of the composition. Particular embodiments contemplate that for a given species, e.g., human, an exogenous and/or non-native glycan may be identified as a matter of routine. For example, in certain embodiments, the glycosylation and the identities of individual endogenous glycans varies among different kingdom, phylum, class, order, family, genus, and/or species or organism. In some aspects, eukaryotic cells share the ability to modify proteins by N-glycosylation. In some embodiments, the first steps of N-glycosylation in eukaryotic cells occurs in the endoplasmic reticulum (ER). In certain aspects, the glycosylation machinery of the ER is highly conserved between all species and results in the biosynthesis of a common Man3GlcNAc2 core structure. Particular embodiments contemplate that further modifications of the N-glycan core take place in the Golgi apparatus whereupon the glycosylation repertoire varies among species. For example, in certain embodiments, yeast express high-mannose glycan structures harboring up to 100 mannose residues in different linkages. In some embodiments, N-glycans found on insect cell proteins belong to the paucimannosidic type which represents the core structure, with further modifications by additional mannose, fucose, and galactose residues. Higher plants even synthesize a significant portion of complex type glycans with two antennae, and non-human immunogenic xylose residues occur with a high frequency. By contrast, animals mainly express multiantennary complex type N-glycans and carry sialic acids at outermost positions of glycan chains. However, in certain aspects, humans do not synthesize two of the major mammalian glycan epitopes, Gala1-3Gal (alpha-Gal) and N-glycolylneuraminic acid (Neu5Gc). In some aspects, humans commonly and/or typically have antibodies directed against these structures. In some embodiments, the non-native and/or exogenous glycan is not a mammalian glycan, e.g., a glycan that is not expressed or synthesized by a mammalian cell. In certain embodiments, the glycan is not a human glycan, e.g., a glycan that is not produced by a human cell, such as a healthy human cell and/or a non-cancerous human cell and/or non-tumorigenic human cell.

In some embodiments, the exogenous and/or non-native glycan is from, produced, and/or synthesized by the same species as the cells of the cell composition. For example, particular embodiments contemplate that within the same species, cells of different lineages, tissues, and/or stages of maturity may express or synthesize one or more different glycans. Thus, in some embodiments, an exogenous and/or non-native glycan is produced by a cell of the same species but a different cell type as the cells in the cell composition. In some embodiments, the non-native glycan is expressed and/or synthesized by cells of the same species but not by immune cells. In particular embodiments, the non-native glycan is expressed and/or synthesized by human cells but not by human immune cells. In some embodiments, the non-native glycan is expressed and/or synthesized by human cells but not by human T cells.

In some embodiments, the source of the non-native and/or exogenous glycan is a protein, e.g., a glycoprotein. In particular embodiments, the glycoprotein may include, but is not limited to, an antibody and/or a fragment or variant thereof, an MHC molecule and/or a fragment or variant thereof, a growth factor, a cytokine, a chemokine, antibody, an Fc-fusion protein, and/or an interleukin. In some embodiments, the glycoprotein is present in a solution, media, and/or a serum. In some embodiments, the glycoprotein is a recombinant protein. In some embodiments, the protein is not native, not endogenous, and/or is not expressed by the cells of the cell composition.

In particular embodiments, the source of the non-native and/or exogenous protein is one or more proteins, e.g., glycoproteins, that have been contacted and/or exposed to the cells of the composition. In some embodiments, the one or more proteins have been contacted and/or exposed to the cells during a process for generating, producing, and/or engineering the cell composition. In some aspects, the one or more have been added, contacted, or incubated with the cells during the culturing of said cells, and/or during a process such as engineering, activating, stimulating, transducing, transfecting, cultivating, or expanding the cells, e.g., to produce or engineer the cell composition.

In some embodiments, the source of the exogenous and/or non-native glycan is a serum, e.g., one or more proteins found within the serum. In some aspects, serum is commonly used as a supplement to cell culture media. In particular aspects, serum is used to provide one or more of a broad spectrum of macromolecules, carrier proteins for lipid substances and trace elements, attachment and spreading factors, low molecular weight nutrients, hormones and growth factors. In certain embodiments, the serum is animal serum. In certain embodiments, the source of the non-native and/or exogenous glycan is or includes fetal bovine serum (FBS), bovine calf serum (BCS), newborn calf serum (NBCS), horse serum, goat serum, lamb serum, donkey serum, or porcine serum. In some aspects, the animal serum is fetal bovine serum (FBS). In some embodiments, the source of the glycan is a serum and/or a protein, e.g., a glycoprotein, that is present in the serum. In some embodiments, the detection of a non-native and/or exogenous glycan indicates residual serum proteins within the cell composition.

In some embodiments, the source of the non-native and/or exogenous glycan is a recombinant protein. In some aspects, the recombinant protein may be added to as a component of a serum replacement and/or serum alternative. In particular embodiments, the source of the exogenous and/or non-native glycan is a serum replacement and/or a serum alternative. In particular embodiments, serum replacement and/or serum alternative is defined, e.g., contains known identities and amount of proteins, e.g., recombinant proteins. In some embodiments, the detection of a non-native and/or exogenous glycan indicates residual recombinant proteins within the cell composition.

In some embodiments, the source of the exogenous and/or non-native glycan is a microorganism or virus. In certain aspects, virus, yeast, mold, mycoplasma, contain and/or express glycoproteins. In some embodiments, detection of an exogenous and/or non-native glycoprotein indicates the presence of microorganism in the cell composition. In some embodiments, a source of an exogenous and/or non-native glycan is a glycoprotein expressed or synthesized by cells, e.g., cells of a cell line, that are different from the cells of the cell composition. In certain embodiments, detection of an exogenous and/or non-native glycans indicates cross contamination by other cell types and/or cell lines.

In some embodiments, the presence, identification, and/or quantification of a non-native and/or exogenous glycan, e.g., by analyzing a surface glycan profile generated from a cell composition or a sample obtained from the cell composition, corresponds to, correlates with, and/or indicates the presence, amount, and/or identity of one or more substances, e.g., residual substances, in the cell composition. In some embodiments, detection of a non-native and/or exogenous glycan indicates a substance, e.g., a residual substance, within the cell composition. In some embodiments, the non-native and/or exogenous glycan is the substance and/or residual substance. In certain embodiments, the substance and/or residual substance is a protein, e.g., a glycoprotein, that contains, e.g., is covalently bound to, the non-native and/or exogenous glycan. In particular embodiments, the substance is or includes a microorganism or a substance produced from the microorganism that expresses and/or synthesis, and/or is capable of expressing and/or synthesizing, the non-native and/or exogenous glycan.

In some aspects, the level and/or amount of the substance, e.g., the residual substance, present in the cell sample is determined by measuring the amount and/or level of the glycan, such as by any of the methods provided herein. In some embodiments, the amount or level of the glycan is quantified as a percentage of the total glycans in the sample. For example, in some embodiments, the methods provided herein allow for detection of relative levels of an individual non-native or exogenous glycan species within a population of glycans. In particular embodiments, the area under one or more peaks corresponding to, e.g., indicating, one or more non-native glycans of a liquid chromatograph can be measured and expressed as a percentage of the total glycans detected. Such an analysis provides a relative percent amount of the exogenous and/or non-native glycan species within the total populations of detected glycans. In certain embodiments, a total amount or concentration of the glycan may be calculated, such as for example, when the total amount of glycans are known.

In some embodiments, the glycan profile, e.g., the surface glycan profile generated from a cell composition or from a sample obtained from the cell composition, is compared to a glycan profile of a reference sample. In some embodiments, the reference sample is or contains one or more of a solution, media, and/or serum. In certain embodiments, the solution, media, and/or serum are or have been contacted, treated, incubated, and/or exposed with the cells of the cell composition. In certain embodiments, the reference sample is or includes a fresh sample of the solution, media, and/or serum, e.g., the sample is taken from the solution, media, or serum prior to exposure to the cells or is taken from a separate aliquot or container that has not been exposed to the cells. In particular embodiments, the presence of a glycan found in the glycan profile generated form the reference sample indicates the presence of an exogenous and/or non-native glycan. In certain embodiments, the presence of an exogenous and/or non-native glycan in a reference sample indicates that the source of the sample is, is likely, or is a candidate source of the substance and/or residual substance.

Particular embodiments contemplate that exogenous and/or non-native glycans may, in some instances, be incorporated into the cell surface glycans of one or more cells of the cell composition. In certain cases, an exogenous and/or non-native glycan is modified and/or altered, and is incorporated into the cell surface glycans of one or more cells.

Thus, in some embodiments, a non-native and/or exogenous glycan that is present in a source, e.g., solution, media, and/or a serum, is modified when it contacts or is otherwise exposed to a cell composition. In such embodiments, the identity of the exogenous and/or non-native glycan in the source, e.g., the solution, media, and/or serum, is a different exogenous and/or non-native glycan when present in the cell composition. Thus, in some instances, an exogenous or native glycan from a particular source may be present in a surface glycan profile obtained from the cell composition, or from a sample of the cell composition, but not present in the glycan profile generated from the reference sample taken from the particular source. In some embodiments, control experiments can be designed and performed as a matter of routine to identify non-native and/or exogenous glycans that have been incorporated into the cell surface glycans of a cell.

In some embodiments, the methods provided herein may be used to verify that a substance has been rinsed, washed, or removed from the cells. In some aspects, the methods provided herein may be used to compare cell culturing conditions and/or processes, e.g., engineering processes, to optimize removal of the substances and/or residual substances that may result from the conditions or process, e.g., such as by residual proteins. In certain embodiments, surface glycan profiles are produced from samples taken at different stages of a process, e.g., an engineering process, to determine if the substances are introduced at one or more stages of the process.

II. CELL COMPOSITIONS

In some embodiments, the provided methods herein can be used to assess the expression of surface glycans, e.g., N-glycans, of one or more compositions of cells to determine or assess the presence, absence, or level of one or more glycans, e.g. N-glycans, present on the surface of the cells, such as according to any of the provided methods described above. In some embodiments, the composition that is assessed is a test cell composition that is a portion of another composition, such as a source composition. In some embodiments, the provided methods can be used to assess or analyze the presence, absence, amount, level and/or relative abundance of one more glycans on the surface of cells of the composition.

In particular embodiments, such information can be used to assess or evaluate glycosylation changes that may impact functional and/or phenotypic characteristics of the cells, such as in connection with one or more of masking of a cell surface marker, a metabolic activity, differentiation state, proliferative or expansion capacity, activation state, cytolytic activity, signaling activity, an adhesion property, or a homing property. In some aspects, information about the glycan profile from cells of a composition can be compared to a reference sample, such as a reference standard or other sample from a reference composition, to evaluate release criteria of the composition, evaluate changes or differences occurring in the composition, e.g. following incubation in the presence of one or more agents or conditions and/or to evaluate similarities and/or differences between and among lots of the same composition produced by substantial the same method or to evaluate similarities or differences between and among compositions from different sources and/or produced or manufactured by different methods.

In some embodiments, information about a surface glycan profile, e.g. presence, absence, identity and/or level of one or more glycan, can be used in the process of screening one or more test agents or conditions on a composition of cells. In some embodiments, such methods include incubating an input composition in the presence of one or more test agents or conditions as described. In some embodiments, the surface glycan profile, e.g. presence, absence, identity and/or level of one or more surface glycans, from a sample from the composition of cells or a portion thereof, e.g. test cell composition, so incubated and compared to a reference sample, such as a reference standard. In some embodiments, one or more test agent or conditions is selected for incubating or treating the cells if the comparison indicates the cell surface glycan profile of the sample or each of the one or more target glycan is substantially the same as the reference sample, e.g. reference standard, and/or if the comparison indicates cell surface glycan profile comprising the one or more target glycans or each of the one or more target glycans differs by no more than or about 20%, no more than or about 15%, no more than or about 10% or no more than or about 5% from the cell surface glycan profile or each of the one or more target glycans to the total glycans present in the reference sample.

In certain embodiments, the methods provided herein can be used to assess surface glycan expression, e.g. presence, absence, identity and/or level of one or more surface glycans, in a composition of cells, for example to compare the surface glycan expression of the composition to another cell composition. In some embodiments, a sample containing one or more surface glycans released from a composition of cells, e.g. test cell composition, is compared to a reference sample and/or to a sample of surface glycans released from a reference composition.

In particular embodiments, the presence, absence, relative amount (i.e., percentage of total surface glycans), or amount of one or more target glycan or target glycans can be assessed. In some embodiments, the target glycan or glycans can be species, families, or groups of glycans. In some embodiments, any of the glycans set forth in Table E1 can be assessed or compared. In some aspects, at least 50, at least 60, at least 70, at least 80, at least 90, at least 100, or at least 200 different species of glycans is assessed and/or compared. In some embodiments, the target glycan or glycans is or comprises high mannose N-glycans, bisected and Sialyl Lewis$^X$ N-glycans, and/or N-acetyl lactosamine containing N-glycans. In some embodiments, the target glycan or glycans is or comprises a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

In some embodiments, the comparison of the surface glycan profile of a cell composition may be compared to a composition of cells that express a different recombinant receptor. In certain embodiments, the surface glycan composition may be compared to a composition of cells do not express the recombinant receptor. In some embodiments, the surface glycan composition may be compared to a composition of cells that is produced by a different process and/or is produced by a process involving incubation in the presence of one or more particular agent or condition. In some embodiments, the surface glycan profile of a cell composition is compared to a different cell composition from a different stage or step of a manufacturing process for producing the cell composition, such an earlier or prior stage or step of the manufacturing process for producing the cell composition.

In certain embodiments, the surface glycan expression profile of a cell composition is assessed and compared to a reference sample. In some embodiments described herein, a reference sample is also referred to as a reference standard. For example, in some embodiments, a cell composition, e.g., a therapeutic cell composition may have a distinct profile of surface glycan expression with respect to the level of surface expression of distinct glycan species, types of glycans, and/or glycan families as compared to compositions of different cells. Thus, in some embodiments, a reference standard may be generated by assessing a plurality of cell compositions. Such a reference standard may be used, in some embodiments, as a quality control and/or for a release assay, or to monitor or control the manufacture or culture of the cell compositions.

In certain embodiments, a reference standard for surface glycan expression is generated by assessing several different cell compositions that contain similar or identical cell compositions. For example, in some embodiments, surface glycan expression profiles are obtained from two or more compositions of engineered cells that were manufactured under different batches of an identical manufacturing process to generate a reference standard. In some embodiments, surface glycan expression profiles are obtained from two or more compositions of cells that are collected at the same stage of a process to manufacture engineered cells to generate a reference standard. In some embodiments, the reference standard is a hypothetical reference standard value or range of values with regard to specific glycan species. In some embodiments, a hypothetical reference standard is based upon data or reference samples from related or similar processes. In certain aspects, data from related processes can be shared such that reference value ranges can be generated that apply to myriad different, but similar, processes. In some embodiments, the reference standard is derived from an exemplary process to which other test processes are compared. In some embodiments, the reference standard is an average or median of the presence, absence, identity and/or level of the one or more target glycan or glycans among a plurality of compositions produced by the process.

In particular embodiments, the reference sample is generating by calculating an average or median value of at least one species of glycan, at least one family of N-glycan, or at least one type of N-glycan. In certain embodiments, the reference standard is a median or mean level of expression of a type of glycan. In certain embodiments, the reference standard is or includes the mean or median level of oligomannose, complex N-glycans, and/or hybrid N-glycans. In certain embodiments, the reference standard is or includes the mean or median expression level of N-glycans with high mannose content, bisected and/or sialyl Lewis$^x$ N-glycans, and/or N-acetyl lactosamine containing N-glycans. In some embodiments, the reference standard is a mean or median expression level of the A2 family, the A2F family, the A3 family, the A4 family, and oligomannose family glycans. In some embodiments, the reference standard is a mean or median expression level of at least 1, 2, 3, 4, 5, 10, 15, 20, 25, 30, 35, 40, 45, 50, 60, 70, 80, 90, 100, 125, 150, 200, 300, 400, or at least 500 glycan species. In some embodiments, the reference standard is calculated from the surface glycan expression profiles of at least two, three, four, five, six, seven, eight, nine, ten, greater than ten, greater than twenty, or greater than fifty cell compositions.

A. Cells

In some embodiments, the cell composition, e.g. source composition or a portion thereof, such as a test cell composition, comprises a population of cells. Any composition containing cells can be assessed according to the provided method. In some embodiments, the population of cells is or comprises a cell line or primary cells. In some embodiments, the population of cells is or comprises primary cells, such as primary cells obtained from a subject, e.g. human subject. In some embodiments, the population of cells is or comprises stem cells, such as induced pluripotent stem cells. In some embodiments, the composition of cells, e.g. source composition or a portion thereof, such as a test cell composition, is a composition that is associated with a process for manufacturing a cell composition, including in connection with engineering cells with a recombinant nucleic acid. In some embodiments, the composition of cells is a pharmaceutical composition.

In certain embodiments, the cells are or include eukaryotic cells. In certain embodiments, the cells of the cell composition are animal cells. In some embodiments, the cells of the composition are mammalian cells. In certain embodiments, the cells are mouse cells, hamster cells, rat cells, or non-human primate cells. In some embodiments, the cells are human cells.

In some embodiments, the cells are cells of a cell line, e.g., e Chinese hamster ovary (CHO) cells, monkey kidney CV1 line transformed by 5V40 (C057); human embryonic kidney line 293; baby hamster kidney cells (BHK); mouse sertoli cells (TM4); monkey kidney cells (CVI-76); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor cells (MMT); rat hepatoma cells (HTC); HIH/3T3 cells, and TRI cells. For an extensive list of mammalian cell lines, those of skill in the art may refer to the American Type Culture Collection catalog (ATCC, Mamassas, Va.). In some embodiments, the cells may be of a variety of cell types, e.g., fibroblasts, myoblasts, macrophages, or epithelial cells.

In particular embodiments, the cells of a composition are or include stem cells. In certain embodiments, cells of the cell composition are pluripotent stem cells, multipotent stem cells, oligopotent stem cells, and/or unipotent stem cells. In particular embodiments, the cells are induced, e.g., induced pluripotent stem cells (ipsc). In particular embodiments, the cells of the composition are cells, e.g., that are in the process of being reprogrammed, e.g., towards pluripotency. In some embodiments, the cells are stem cells are in the process of differentiation.

In some embodiments, the cells of the composition are immune cells. In particular embodiments, a cell composition contains one or more of T cells, B cells, and/or NK cells. In some embodiments the cells of the cell composition are CD3+ T cells. In some embodiments, the cells are CD4+ T cells. In certain embodiments, the cells are CD8+ T cells. In some embodiments, one or more of effector T cells, Helper T cells, cytotoxic T cells, memory T cells, and suppresser T cells. In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In certain embodiments, the surface glycans of primary cells are assessed. In some embodiments, the composition of cells contains primary cells, such as those isolated directly from a subject and/or isolated from a subject and frozen. In some embodiments, the cells include one or more subsets of T cells or other cell types, such as whole T cell populations, CD4+ T cells, CD8+ T cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous.

In some embodiments, one or more cells of the composition are engineered cells. In some cases, the one or more cells are engineered to contain a recombinant nucleic acid, e.g. contain heterologous nucleic acid and/or express a heterologous protein. In some embodiments, the recombinant nucleic acid encodes a recombinant protein. In some cases, the recombinant protein can be any protein that is desired to be expressed or produced by a recombinant cell composition. In some embodiments, the recombinant protein is a recombinant receptor. In some embodiments, the recombinant nucleic acid is or includes a viral vector, e.g. lentiviral or retroviral vector, that is transferred or introduced into the cell for expression of the recombinant protein.

B. Exemplary Engineered Cells

In certain embodiments, the engineered cells contain a heterologous polynucleotide that encodes a recombinant receptor. In some embodiments, the recombinant receptor is a chimeric receptor or an antigen receptor, such as a chimeric antigen receptor (CAR) or a T cell receptor (TCR). In certain embodiments, the engineered cells are produced, manufactured, and/or generated as described in Section III.

In some embodiments, all or a portion of the cells in a composition contain or are engineered to contain an engineered receptor, such as a chimeric antigen receptor (CAR), or a T cell receptor (TCR). In particular embodiments, all or a portion of the cells in a composition express the engineered receptor. In some embodiments, compositions containing engineered cells are enriched for such cells. In certain embodiments, the cells of a certain type such as T cells or CD8$^+$ or CD4 T cells are enriched or selected. In particular embodiments, the cell composition is a therapeutic and/or a pharmaceutical cell composition, such as for adoptive cell therapy.

1. Chimeric Antigen Receptors (CARs)

In certain embodiments, the methods provided herein can be used to assess the surface glycan expression of a composition of cells that includes or is composed of cells that generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., *Cancer Discov.,* 3(4): 388-398 (2013); Davila et al. *PLoS ONE* 8(4): e61338 (2013); Turtle et al., *Curr. Opin. Immunol.,* 24(5): 633-39 (2012); Wu et al., *Cancer,* 18(2): 160-75 (2012). In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., *Nature Reviews Clinical Oncology,* 10, 267-276 (2013); Wang et al., *J. Immunother.* 35(9): 689-701 (2012); and Brentjens et al., *Sci Transl Med,*. 5(177) (2013). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, surface expression of N-glycans is assessed in a composition of cells that contains cells expressing a recombinant receptor, e.g., a CAR, that targets an antigen, and the antigen targeted by the receptor is a polypeptide. In some embodiments, the antigen is a carbohydrate or other molecule. In some embodiments, the antigen is selectively expressed or overexpressed on cells of a disease or condition, e.g., tumor cells or pathogenic cells, as compared to normal or non-targeted cells or tissues. In other embodiments, the antigen is expressed on normal cells and/or is expressed on the engineered cells. In some embodiments, among the antigens targeted by the chimeric receptors are those expressed in the context of a disease, condition, or cell type to be targeted via the adoptive cell the In some embodiments, the labeling reagent and/or derivatizing reagent is contacted, treated, and/or incubated with the glycans in the presence of a solvent that is a formamide. Among the diseases and conditions are proliferative, neoplastic, and malignant diseases and disorders, including cancers and tumors, including hematologic cancers, cancers of the immune system, such as lymphomas, leukemia, and/or myelomas, such as B, T, and myeloid leukemia, lymphomas, and multiple myelomas.

In some embodiments, surface glycans are released from a cell composition containing cells that express a recombinant receptor, e.g., a CAR, that binds to an antigen. Antigens that may be targeted by the receptors include, but are not limited to, αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRHS), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), glypican-3 (GPC3), Her2/neu (receptor tyrosine kinase erbB2), Her3 (erb-B3), Her4 (erb-B4), erbB dimers, human high molecular weight-melanoma-associated antigen (HMW-MAA), hepatitis B surface antigen, Human leukocyte antigen A1 (HLA-A1), human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, preferentially expressed antigen of melanoma (PRAME), progesterone receptor, a prostate specific antigen, prostate stem cell antigen (PSCA), prostate specific membrane antigen (PSMA), receptor tyrosine kinase like orphan receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms tumor 1 (WT-1), and a pathogen-specific or pathogen-expressed antigen, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is a pathogen-specific or pathogen expressed antigen. In some embodiments, the CAR is specific for viral antigens (such as HIV, HCV, HBV, etc.), bacterial antigens, and/or parasitic antigens.

In some embodiments, the antibody or an antigen-binding fragment (e.g. scFv or VH domain) specifically recognizes an antigen, such as CD19. In some embodiments, the antibody or antigen-binding fragment is derived from, or is a variant of, antibodies or antigen-binding fragment that specifically binds to CD19.

In some embodiments the scFv and/or VH domains is derived from FMC63. FMC63 generally refers to a mouse monoclonal IgG1 antibody raised against Nalm-1 and -16 cells expressing CD19 of human origin (Ling, N. R., et al. (1987). *Leucocyte typing III.* 302). The FMC63 antibody comprises CDR H1 set forth in SEQ ID NO: 29; CDR H2 set forth in SEQ ID NO: 30; CDR H3 set forth in SEQ ID NOS: 31 or 45; and CDR L1 set forth in SEQ ID NO: 26; CDR L2 set forth in SEQ ID NO: 27 or 46; and CDR L3 set forth in SEQ ID NO: 28 or 45. The FMC63 antibody comprises the heavy chain variable region (VH) comprising the amino acid sequence of SEQ ID NO: 32 and the light chain variable region (VL) comprising the amino acid sequence of SEQ ID NO: 33. In some embodiments, the scFv comprises a variable light chain containing a CDR L1 sequence of SEQ ID NO: 26, a CDR L2 sequence of SEQ ID NO: 28, and a CDR L3 sequence of SEQ ID NO: 28 and/or a variable heavy chain containing a CDR H1 sequence of SEQ ID NO: 29, a CDR H2 sequence of SEQ ID NO: 30, and a CDR H3 sequence of SEQ ID NO: 31, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the scFv comprises a variable heavy chain region of FMC63 set forth in SEQ ID NO: 32 and a variable light chain region of FMC63 set forth in SEQ ID NO: 33, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the variable heavy and variable light chains are connected by a linker. In some embodiments, the linker is set forth in SEQ ID NO:58. In some embodiments, the scFv comprises, in order, a $V_H$, a linker, and a VL. In some embodiments, the scFv comprises, in order, a $V_L$, a linker, and a $V_H$. In some embodiments, the scFv is encoded by a sequence of nucleotides set forth in SEQ ID NO: 25 or a sequence that exhibits at least 85%, 86%, 87%, 88%, 89%, 90%, 91%, 92%, 93%, 94%, 95%, 96%, 97%, 98%, or 99% sequence identity to SEQ ID NO: 25. In some embodiments, the scFv comprises the sequence of amino acids set forth in SEQ ID NO: 34 or a sequence that exhibits at least 85%, 86%, 87%, 88%, 89%, 90%, 91%, 92%, 93%, 94%, 95%, 96%, 97%, 98%, or 99% sequence identity to SEQ ID NO: 34.

In some embodiments, the scFv and/or VH domain is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). The SJ25C1 antibody comprises CDR H1, H2 and H3 set forth in SEQ ID NOS: 38-40, respectively, and CDR L1, L2 and L3 sequences set forth in SEQ ID NOS: 35-37, respectively. The SJ25C1 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the svFv comprises a variable light chain containing a CDR L1 sequence set forth in SEQ ID NO:35; a CDR L2 set forth in SEQ ID NO: 36; and a CDR L3 set forth in SEQ ID NO:37; and/or a variable heavy chain containing a CDR H1 set forth in SEQ ID NO:38, a CDR H2 set forth in SEQ ID NO:39, and a CDR H3 set forth in SEQ ID NO:40, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the scFv comprises a variable heavy chain region of SJ25C1 set forth in SEQ ID NO:41 and a variable light chain region of SJ25C1 set forth in SEQ ID NO: 42, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the variable heavy and variable light chains are connected by a linker. In some embodiments, the linker is set forth in SEQ ID NO: 43. In some embodiments, the scFv comprises, in order, a VH, a linker, and a $V_L$. In some embodiments, the scFv comprises, in order, a $V_L$, a linker, and a VH. In some embodiments, the scFv comprises the sequence of amino acids set forth in SEQ ID NO:44 or a sequence that exhibits at least 85%, 86%, 87%, 88%, 89%, 90%, 91%, 92%, 93%, 94%, 95%, 96%, 97%, 98%, or 99% sequence identity to SEQ ID NO:44.

In some aspects, the CAR contains a ligand- (e.g., antigen-) binding domain that binds or recognizes, e.g., specifically binds, a universal tag or a universal epitope. In some aspects, the binding domain can bind a molecule, a tag, a polypeptide and/or an epitope that can be linked to a different binding molecule (e.g., antibody or antigen-binding fragment) that recognizes an antigen associated with a disease or disorder. Exemplary tag or epitope includes a dye (e.g., fluorescein isothiocyanate) or a biotin. In some aspects, a binding molecule (e.g., antibody or antigen-binding fragment) linked to a tag, that recognizes the antigen associated with a disease or disorder, e.g., tumor antigen, with an engineered cell expressing a CAR specific for the tag, to effect cytotoxicity or other effector function of the engineered cell. In some aspects, the specificity of the CAR to the antigen associated with a disease or disorder is provided by the tagged binding molecule (e.g., antibody), and different tagged binding molecule can be used to target different antigens. Exemplary CARs specific for a universal tag or a universal epitope include those described, e.g., in U.S. Pat. No. 9,233,125, WO 2016/030414, Urbanska et al., (2012) Cancer Res 72: 1844-1852, and Tamada et al., (2012). Clin Cancer Res 18:6436-6445.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a major histocompatibility complex (MHC)-peptide complex. In some embodiments, an antibody or antigen-binding portion thereof that recognizes an MHC-peptide complex can be expressed on cells as part of a recombinant receptor, such as an antigen receptor. Among the antigen receptors are functional non-T cell receptor (TCR) antigen receptors, such as chimeric antigen receptors (CARs). In some embodiments, a CAR containing an antibody or antigen-binding fragment that exhibits TCR-like specificity directed against peptide-MHC complexes also may be referred to as a TCR-like CAR. In some embodiments, the CAR is a TCR-like CAR and the antigen is a processed peptide antigen, such as a peptide antigen of an intracellular protein, which, like a TCR, is recognized on the cell surface in the context of an MHC molecule. In some embodiments, the extracellular antigen-binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning α chain, in some cases with three α domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally CD8+ T cells, but in some cases CD4+ T cells. In some embodiments, MHC class II molecules deliver peptides originating in the vesicular system to the cell surface, where they are typically recognized by CD4+ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by known methods (see e.g. US Published Application Nos. US 2002/0150914; US 2003/0223994; US 2004/0191260; US 2006/0034850; US 2007/00992530; US20090226474; US20090304679; and International App. Pub. No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US Pat. App. Pub. No. US20020150914, US20140294841; and Cohen CJ. et al. (2003) *J Mol. Recogn.* 16:324-332.

[0041][0037] The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody, VHH or VNAR) or fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. In some aspects, the CAR is a bispecific CAR, e.g., containing two antigen-binding domains with different specificities.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; variable heavy chain (VH) regions, single-chain antibody molecules such as scFvs and single-domain VH single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

Single-domain antibodies (sdAb) are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known. Exemplary single-domain antibodies include sdFv, nanobody, VHH or VNAR.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, the spacer is less than 250 amino acids in length, less than 200 amino acids in length, less than 150 amino acids in length, less than 100 amino acids in length, less than 75 amino acids in length, less than 50 amino acids in length, less than 25 amino acids in length, less than 20 amino acids in length, less than 15 amino acids in length, less than 12 amino acids in length, or less than 10 amino acids in length. In some embodiments, the spacer is from or from about 10 to 250 amino acids in length, 10 to 150 amino acids in length, 10 to 100 amino acids in length, 10 to 50 amino acids in length, 10 to 25 amino acids in length, 10 to 15 amino acids in length, 15 to 250 amino acids in length, 15 to 150 amino acids in length, 15 to 100 amino acids in length, 15 to 50 amino acids in length, 15 to 25 amino acids in length, 25 to 250 amino acids in length, 25 to 100 amino acids in length, 25 to 50 amino acids in length, 50 to 250 amino acids in length, 50 to 150 amino acids in length, 50 to 100 amino acids in length, 100 to 250 amino acids in length, 100 to 150 amino acids in length, or 150 to 250 amino acids in length. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. *Clin. Cancer Res.,* 19:3153 (2013), international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 2), and is encoded by the sequence set forth in SEQ ID NO: 3. In some embodiments, the spacer has the sequence set forth in SEQ ID NO: 4. In some embodiments, the spacer has the sequence set forth in SEQ ID NO: 5. In some embodiments, the constant region or portion is of IgD. In some embodiments, the spacer has the sequence set forth in SEQ ID NO: 6. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 2, 4, 5, or 6.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In certain embodiments, methods provided engineered cells that express one or more recombinant antigen receptor. In some embodiments, the cells can include cells genetically engineered with a recombinant receptor, such as a chimeric antigen receptor.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD5, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., *Sci. Transl. Medicine*, 5(215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO:8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 19.

In some embodiments, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 24), equine rhinitis A virus (E2A, e.g., SEQ ID NO: 23), Thosea asigna virus (T2A, e.g., SEQ ID NO: 7 or 20), and porcine teschovirus-1 (P2A, e.g., SEQ ID NO: 21 or 22) as described in U.S. Patent Publication No. 20070116690. An exemplary T2A linker sequence comprises the sequence of amino acids set forth in SEQ ID NO: 7 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, an E2A or an F2A. Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO: 8 or 19) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., a T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 8 or 19 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8 or 19.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain. In some aspects, the transmembrane domain contains a transmembrane portion of CD28 or a variant thereof. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 9; in some embodiments, the transmembrane-domain containing portion of the recombinant receptor comprises the sequence of amino acids set forth in SEQ ID NO: 10 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 11 or 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 11 or 12. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 13 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. Nos. 7,446,190 or 8,911,993. For example, in some embodiments, the intracellular signaling domain comprises the sequence of amino acids as set forth in SEQ ID NO: 14, 15, or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 14, 15, or 16.

In some aspects, the spacer contains only a hinge region of an IgG, such as only a hinge of IgG4 or IgG1, such as the hinge only spacer set forth in SEQ ID NO: 2. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 5. In some embodiments, the spacer is an Ig hinge, e.g., an IgG4 hinge, linked to a CH3 domain only, such as set forth in SEQ ID NO: 4. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 7, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 8, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

2. TCRs

In certain embodiments, the surface expression of glycans, e.g., N-glycans, of cell compositions containing engineered cells that express a recombinant receptor are assessed by the methods provided herein. In some embodiments, the expression of surface glycans is assessed in engineered cells, such as T cells, that express a T cell receptor (TCR) or an antigen-binding portion thereof.

In certain embodiments, the methods provided herein may be used to assess the surface glycan profile, i.e., the expression of the surface glycans, of a composition of cells that express a recombinant T cell receptor. In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., *Immunobiology: The Immune System in Health and Disease,* 3rd Ed., *Current Biology Publications*, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ T cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) *Nat Immunol*, 4, 55-62; Holler et al. (2000) *Proc Natl Acad Sci USA*, 97, 5387-92), phage display (Li et al. (2005) *Nat Biotechnol*, 23, 349-54), or T cell display (Chervin et al. (2008) *J Immunol Methods*, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using computer prediction models known to those of skill in the art. In some embodiments, for predicting MHC class I binding sites, such models include, but are not limited to, ProPred1 (Singh and Raghava (2001) *Bioinformatics* 17(12):1236-1237, and SYFPEITHI (see Schuler et al. (2007) *Immunoinformatics Methods in Molecular Biology*, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known to those of skill in the art. For predicting MHC class 1 binding sites, such models include, but are not limited to, ProPred1 (described in more detail in Singh and Raghava, ProPred: prediction of HLA-DR binding sites. *BIOINFORMATICS* 17(12):1236-1237 2001), and SYFPEITHI (see Schuler et al. SYFPEITHI, Database for Searching and T-Cell Epitope Prediction. in *Immunoinformatics Methods in Molecular Biology*, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known to those of skill in the art, See e.g., Soo Hoo, W. F. et al. *PNAS* (USA) 89, 4759 (1992); Wülfing, C. and Plückthun, A., *J. Mol. Biol.* 242, 655 (1994); Kurucz, I. et al. *PNAS* (USA) 90 3830

(1993); International published PCT Nos. WO 96/13593, WO 96/18105, WO99/60120, WO99/18129, WO 03/020763, WO2011/044186; and Schlueter, C. J. et al. *J. Mol. Biol.* 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO: 17). In some embodiments, the linker has the sequence GSADDAKKDAAKKDGKS (SEQ ID NO: 18).

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Multi-Targeting

In some embodiments, the surface glycan expression is assessed in cell compositions that contain cells designed for multi-targeting strategies. In some embodiments, the cell compositions contain cells designed for multi-targeting strategies such as cells that express two or more genetically engineered receptors on the cell, with each receptor recognizing the same or a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, surface glycans are released and analyzed from a cell composition that contains the cells that include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF—KB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy are achieved.

III. PROCESS FOR MANUFACTURING OR PREPARING CELL COMPOSITIONS

In particular embodiments, the methods provided herein can be used to assess the surface expression of glycans, e.g., N-glycans, of one or more compositions at various stages of a process for manufacturing or generating engineered cells. In particular embodiments, the process may be for the manufacturing or generation of engineered cells that express a recombinant receptor, e.g., a CAR or TCR, as described herein such as in Section III. In some embodiments, the process includes steps for isolation, separation, selection, cultivation (e.g., stimulation of the cells, for example, to induce their proliferation and/or activation), transduction and/or transfection, washing, suspension, dilution, concentration, and/or formulation of the cells. In certain embodiments, surface glycan expression is assessed in one or more cell compositions that are obtained prior to, in connection with, or after, steps for isolation, separation, selection, cultivation (e.g., stimulation of the cells, for example, to induce their proliferation and/or activation), transduction and/or transfection, washing, suspension, dilution, concentration, and/or formulation of the cells. In particular embodiments, cells may be collected at any stage or between any stages in the process of manufacturing or generating engineered cells. In some embodiments, the cells may be stored, e.g., cryopreserved, for a later analysis of surface glycans, or may be directly incubated under conditions to release surface glycans.

In some embodiments, glycans, e.g., N-glycans, that are released from the surface of cells from cell compositions taken at various steps in the process for generating or manufacturing engineered cells are analyzed. In some embodiments, the compositions include a cell composition that contains PBMCs. In certain embodiments, the compositions include a cell composition contains selected CD4+ or CD8+ T cells. In some embodiments, the cell compositions include a cell composition that contains activated T cell compositions. In certain embodiments, the T cell composition contains cells that were activated and transduced or transfected with a vector encoding a recombinant receptor. In particular embodiments, the cell composition contains expanded recombinant receptor-expressing cells.

In certain embodiments, the surface expression of glycans, e.g., N-glycans are assessed from cells of cell compositions taken at various steps in the process for generating or manufacturing engineered cells. In some embodiments, the cell compositions include compositions that contain bulk PBMCs. In certain embodiments, the cell compositions include a composition that contains thawed cryopreserved cell compositions containing selected CD4+ or CD8+ T cells selected by immunoaffinity-based selection. In some embodiments, the compositions include a composition that contains T cells incubated with anti-CD3/anti-CD28 beads in the presence of IL-2, IL-15 and/or IL-7 for 18-24 hours at 37° C. In certain embodiments, the cell compositions include a composition that contains activated T cells that were transduced with a lentiviral vector encoding a CAR. In certain embodiments, the cell compositions include a composition that contains thawed, cryopreserved cell compositions containing CAR-expressing cells that were subjected to expansion in the presence of IL-2, IL-15 and/or IL-17 cytokines prior to cryopreservation. In some embodiments, the cell composition is a thawed cryopreserved drug product.

In particular embodiments, the methods provided herein may be used to assess the surface expression of glycans, e.g., N-glycans, of cells from compositions collected during a process for generating or manufacturing engineered cells. In some embodiments, the cell compositions are composed of cells at a stage prior to preforming a step for isolation, separation, selection, cultivation, activation, transduction and/or transfection, expansion, washing, suspension, dilution, concentration, and/or formulation of the cells. In certain embodiments, the cell compositions are composed of cells following a step for isolation, separation, selection, cultivation, activation, transduction and/or transfection, expansion, washing, suspension, dilution, concentration, and/or formulation of the cells. In certain embodiments, the cell compositions are composed of cells undergoing a step for isolation, separation, selection, cultivation, activation, transduction and/or transfection, expansion, washing, suspension, dilution, concentration, and/or formulation of the cells.

In some embodiments, the methods provided herein may be used to assess the surface expression of glycans, e.g., N-glycans, of cells from compositions collected during a process for generating or manufacturing engineered cells, for example to compare the glycan surface expression with glycan surface expression of a different cell composition. In some embodiments, the surface glycan composition is obtained from a composition of cells at or undergoing a step in the process, and the expression of the glycans is compared to the surface glycan expression of a cell composition at or undergoing a prior step in the process. In certain embodiments, the surface glycan expression is obtained from a composition of cells at or undergoing a step in the process, and the surface glycan expression is compared to the surface glycan expression of a composition of cells that is at or undergoing a step that is downstream in the process. In some embodiments, the surface glycan expression is obtained from a composition of cells at or undergoing a step in the process, and the surface glycan expression is compared to the surface glycan expression of a composition of cells has completed the process. In particular embodiments, the surface glycan expression is obtained from a composition of cells at or undergoing a step in the process, and the surface glycan expression is compared to the surface glycan expression of a composition of cells has not undergone the process.

In particular embodiments, the methods provided herein may be used to assess the surface expression of glycans, e.g., N-glycans, of cells from compositions that have completed a process for generating or manufacturing engineered cells. In some embodiments, compositions of cells have completed the same process and express the same one or more recombinant receptors. In certain embodiments, the compositions of cells have completed the same process and express different one or more recombinant receptors. In some embodiments, surface glycan expression is compared between two or more cell compositions that have completed the same process and express the same one or more recombinant receptors.

Particular embodiments contemplate that it may be desirable for different cell compositions that express the same recombinant receptor and that have undergone the same process to have similar surface glycan expression. In some embodiments, surface glycan expressions of a plurality of cell compositions that express the same recombinant receptor and that have undergone the same process are measured and/or assessed. In some embodiments, the methods can be employed in a release assay to confirm consistency and/or substantial homogeneity of a cell composition prior to release of a cell composition, e.g. therapeutic composition, for administration to a subject. In some embodiments, the surface glycan profile, e.g. presence, absence, identity and/or level of one or more glycans, in a sample from a cell composition are compared to a reference standard that is or indicates a release specification, a label requirement and/or a compendia specification.

In some embodiments, a reference standard comprises an average or median of the presence, absence, identity and/or level of the one or more target glycan or glycans among a plurality of compositions produced by the process. In particular embodiments, the mean, median, and/or variance of a measurement of expression of one or more target glycan or glycans, e.g. glycan species, families, and/or groups, are calculated for a plurality of the cell compositions. In some embodiments, the presence, absence, identity and/or level of one or more target glycan or glycans in a sample released from a cell composition, e.g. test cell composition, according to the provided methods is compared to such average or median of the target glycan or glycans.

In some embodiments, the cell composition is released for treatment of a subject only if the cell surface glycan profile of the composition is substantially the same as the reference sample and/or if the percent of a target glycan or each of a plurality of target glycans to the total glycans present in the sample differs by no more than 25%, no more than 20% or no more than 10% from the percent of the target glycan or each of the plurality of target glycans to the total glycans present in the reference sample.

In some embodiments, one or more parameters of one or more steps of the process for manufacturing or generating the engineered cells are adjusted, altered, and/or changed if the variance of the expression of one or more glycan species, families, and/or groups is greater than a threshold. In some embodiments, the threshold is a variation of ±50%, ±33%, ±25%, ±20%, ±15%, ±10%, ±7.5%, ±5%, ±4%, ±3%, ±2%, ±1%, ±0.1%, ±0.05%, or ±0.01% of a measurement of the expression of one or more glycan species, families, and/or groups. In certain embodiments, the measurement of the expression is the relative amount of the one or more glycan species, families, and/or groups, i.e., the percentage of the expression of the one or more glycan species, families, and/or groups of the total surface glycan expression. Examples of parameters that may be altered to improve consistency and/or reduce variation of surface glycan expression includes timing and/or duration of incubations, concentrations of cell preparations, additional or removal of reagents, and concentrations of reagents.

In some embodiments, the provided methods are carried out on one or more compositions produced in connection with the preparation or manufacturing of a cell composition containing engineered cells. In some embodiments, the manufacturing process comprises one or more stages or steps that result in cells or a cell composition containing cells isolated from a biological sample by leukapheresis or apheresis; cells selected from a biological sample by immunoaffinity-based methods; cells introduced with a recombinant nucleic acid, optionally a viral vector encoding a recombinant protein; cell incubated in the presence of one or more test agents, optionally one more peptide, protein, polypeptide, nucleic acid, small molecule; cells activated, expanded in the presence of one or more stimulating conditions; and/or cryopreservation of cells in the presence of a cryoprotectant; and/or cells formulated for administration to a subject, optionally in the presence of a pharmaceutically acceptable excipient.

1. Preparation of Cells for Genetic Engineering

Among the cells that may be assessed for glycan surface expression by the methods provided herein are engineered cells that express recombinant receptors. In certain embodiments, the surface glycan expression may be assessed by the methods provided herein from one or more compositions of cells collected from various stages of the genetic engineering process.

The genetic engineering generally involves introduction of a nucleic acid encoding the recombinant or engineered component into a composition containing the cells, such as by retroviral transduction, transfection, or transformation. In some embodiments, surface glycans are assessed in compositions of cells that are collected prior the start of the retroviral transduction, transfection, or transformation. In certain embodiments, surface glycans are assessed in compositions of cells that are collected immediately after the process of the retroviral transduction, transfection, or transformation. In particular embodiments, the surface glycans are assessed in compositions of cells that are collected at one or more stages of the retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ T cells, CD8+ T cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MATT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, Ca++/Mg++ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ T cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. *Blood.* 1:72-82 (2012); Wang et al. *J Immunother.* 35(9):689-701 (2012). In some embodiments, combining TCM-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L−CD8+ and/or CD62L+CD8+ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ T cell population or subpopulation, also is used to generate the CD4+ T cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ T cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ T cells are CD62L+ and CD45RO+. In some embodiments, effector CD4+ T cells are CD62L− and CD45RO−.

In one example, to enrich for CD4+ T cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. *J Immunother.* 35(9): 651-660 (2012), Terakura et al. *Blood.* 1:72-82 (2012), and Wang et al. *J Immunother.* 35(9):689-701 (2012).

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. *Lab Chip* 10, 1567-1573 (2010); and Godin et al. *J Biophoton.* 1(5):355-376 (2008). In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/mL). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. *J Immunother.* 35(9): 651-660 (2012), Terakura et al. *Blood.* 1:72-82 (2012), and/or Wang et al. *J Immunother.* 35(9):689-701 (2012).

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

2. Vectors and Methods for Genetic Engineering

Various methods for the introduction of genetically engineered components, e.g., recombinant receptors, e.g., CARs or TCRs, are well known. Exemplary methods include those for transfer of nucleic acids encoding the receptors, including via viral, e.g., retroviral or lentiviral, transduction, transposons, and electroporation. In some embodiments, surface glycan expression is assessed in a composition of cells that are collected prior to, during, or immediately after the genetic engineering process. In some embodiments, the surface glycan expression is assessed and compared among compositions of cells at corresponding stages of the process to introduce genetically engineered components. In some embodiments, the compositions are or have been engineered to express the same recombinant receptor, but by different methods of introducing the genetic material.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. Gene Therapy doi: 10.1038/gt.2014.25 (2014); Carlens et al. *Exp Hematol.*, 28(10): 1137-46 (2000); Alonso-Camino et al. *Mol Ther Nucl Acids,* 2, e93 (2013); Park et al., *Trends Biotechnol.*, November 29(11): 550-557 (2011).

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman, BioTechniques, 7:980-990 (1989); Miller, A. D. *Human Gene Therapy,* 1:5-14 (1990); Scarpa et al. *Virology,* 180:849-852 (1991); Burns et al. *Proc. Natl. Acad. Sci. USA,* 90:8033-8037 (1993); and Boris-Lawrie and Temin, *Cur. Opin. Genet. Develop.*, 3:102-109 (1993).

Methods of lentiviral transduction are known. Exemplary methods are described in, e.g., Wang et al., *J. Immunother.,* 35(9): 689-701 (2012); Cooper et al. *Blood.* 101:1637-1644 (2003); Verhoeyen et al., *Methods Mol Biol.*, 506: 97-114 (2009); and Cavalieri et al., *Blood.*, 102(2): 497-505 (2003).

In some embodiments, recombinant nucleic acids are transferred into T cells via electroporation (see, e.g., Chicaybam et al, *PLoS ONE* 8(3): e60298 (2013) and Van Tedeloo et al. *Gene Therapy* 7(16): 1431-1437 (2000)). In some embodiments, recombinant nucleic acids are transferred into T cells via transposition (see, e.g., Manuri et al. *Hum Gene Ther* 21(4): 427-437 (2010); Sharma et al. *Molec Ther Nucl* Acids 2, e74 (2013); and Huang et al. *Methods Mol Biol* 506: 115-126 (2009)). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, *Nature,* 346: 776-777 (1990)); and strontium phosphate DNA co-precipitation (Brash et al., *Mol. Cell Biol.,* 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, *Methods Mol Biol.* 907:645-66 (2012); or Barrett et al., *Chimeric Antigen Receptor Therapy for Cancer Annual Review of Medicine*, Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

In some aspects, the cells further are engineered to promote expression of cytokines or other factors. Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

3. Compositions and Formulations

In some embodiments, the cells, such as cells genetically engineered with a recombinant receptor (e.g. CAR-T cells) are provided as compositions, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

In some embodiments, a composition of cells is generated or manufactured for the purposes of a cell therapy. In some embodiments, the cell composition is a pharmaceutical composition or formulation. Such compositions can be used in accord with the provided methods, for example, to assess their release for use in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered. In some embodiments, methods provided herein may be used to compare surface glycan expression of cell compositions composed of the same engineered cells, but with different pharmaceutical formulations.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In particular embodiments, methods provided herein may be used to compare surface glycan expression of cell compositions composed of the same engineered cells, but with different pharmaceutically acceptable carriers.

In some embodiments, the T cell therapy, such as engineered T cells (e.g. CAR T cells), are formulated with a pharmaceutically acceptable carrier. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being prevented or treated with the cells, including one or more active ingredients where the activities are complementary to the cells and/or the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some embodiments contain cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be formulated for administration using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

IV. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X". In certain embodiments, "about" a stated value refers to a value within ±25%, ±20%, ±10%, ±5%, ±1%, ±0.1%, or ±0.01% of the stated value.

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

V. EXEMPLARY EMBODIMENTS

Among the provided embodiments are:

1. A method for assessing cell surface glycans, the method comprising:

(a) incubating a test composition comprising a plurality of cells under conditions to release one or more glycans from the surface of cells in the test composition, wherein a sample comprising one or more cell surface glycans is generated; and (b) determining the presence, absence, identity and/or level of glycans present in the sample, thereby assessing the cell surface glycan profile of the sample.

2. A method for assessing cell surface glycans, the method comprising determining the presence, absence, identity and/or level of glycans present in a sample, thereby assessing the cell surface glycan profile of the sample, wherein the sample comprises one or more glycans released from the surface of cells present in a test composition comprising a plurality of cells after incubation of the test composition under conditions to release the one or more glycans.

3. The method of embodiment 1 or embodiment 2, wherein the glycans are N-glycans.

4. The method of any of embodiments 1-3, wherein cells in the test cell composition comprise whole or intact cells.

5. The method of any of embodiments 1-4, wherein the cells are live cells.

6. The method of any of embodiments 1-5, wherein:
the test cell composition is not homogenized or sonicated prior to the incubation; and/or
the test cell composition is not incubated with a protease prior to the incubation, optionally wherein the protease is trypsin; and/or
the cells in the test cell composition, prior to or during the incubation, are not contacted with an agent to extract one or more cell surface or membrane proteins, optionally wherein the agent is a detergent or protease, optionally trypsin; and/or
less than 10% of the cells are lysed and/or ruptured during the incubation.

7. The method of any of embodiments 1-6, wherein the test cell composition comprises no more than $5 \times 10^6$ cells.

8. The method of any of embodiments 1-7, wherein the test cell composition comprises between $1 \times 10^6$ cells and $5 \times 10^6$ cells, inclusive.

9. The method of any of embodiments 1-8, wherein the test cell composition comprises a concentration of no more than $1 \times 10^8$ cells/mL.

10. The method of any of embodiments 1-9, wherein the test cell composition comprises a concentration of between $1 \times 10^5$ cells/mL and $1 \times 10^8$ cells/mL, inclusive, between $1 \times 10^6$ cells/mL and $5 \times 10^7$ cells/mL, inclusive, or between $5 \times 10^6$ cells/mL and $2.5 \times 10^7$ cells/mL, inclusive.

11. The method of any of embodiments 1-10, wherein the incubation is carried out in the presence of an N-glycosidase.

12. The method of embodiment 11, wherein the N-glycosidase is a peptide N-glycosidase (PNGase) F.

13. The method of embodiment 12, wherein the PNGase F is recombinant.

14. The method of any of embodiments 1-6, wherein the one or more glycans are one or more N-glycans, and wherein the method comprises:
(i) incubating between $1 \times 10^6$ and $5 \times 10^6$ cells from the test composition with a recombinant PNGase F under conditions to release the one or more N-glycans from the surface of the cells of the test composition;
(ii) labeling the one or more N-glycans with a detectable label, optionally a fluorescent label; and
(iii) determining the presence, absence, or level of the labeled N-glycans, thereby assessing the cell surface glycan profile of the sample.

15. The method of embodiment 14, wherein the test cell composition comprises about $1 \times 10^6$ to $2.5 \times 10^6$ cells.

16. The method of embodiment 13 or embodiment 14, wherein the test cell composition comprises a concentration of between $1 \times 10^6$ cells/mL and $5 \times 10^7$ cells/mL.

17. The method of any of embodiments 12-16, wherein the PNGase F comprises a PGNase F of *Flavobacterium meningosepticum*, or a portion or mutant thereof that is enzymatically active.

18. The method of any of embodiments 12-17, wherein the PNGase F comprises the amino acid sequence set forth in SEQ ID NO: 1 or a portion or mutant thereof that is enzymatically active, or an amino acid sequence that exhibits at least 85%, 86%, 87%, 88%, 89%, 90%, 91%. 92%. 93%, 94%, 95%, 96%, 97%, 98%, 99% or more sequence identity to SEQ ID NO:1 or is a portion thereof that is enzymatically active.

19. The method of any of embodiment 12-18, wherein the PNGase F comprises the amino acid sequence set forth in SEQ ID NO: 1.

20. The method of any of embodiments 12-19, wherein the PNGase F comprises a tag, optionally an affinity tag.

21. The method of embodiment 20, wherein the tag is a poly-histidine (His-tag). 22. The method of any of embodiments 12-21, wherein:
the PNGase F is greater than or greater than about 90%, greater than or greater than about 92%, greater than or greater than about 95%, or greater than or greater than about 98% pure; and/or
the PNGase F comprises less than or less than about 10%, less than or less than about 8%, less than or less than about 5%, less than or less than about 2% non-PNGase F protein contaminants; and/or
the PNGase F is greater than or greater than about 90%, greater than or greater than about 92%, greater than or greater than about 95%, or greater than or greater than about 98% homogeneous, optionally as determined by SDS-PAGE and protein staining, optionally Coomasie Blue staining.

23. The method of any of embodiments 11-22, wherein the N-glycosydase, optionally PNGase F, is in an enzymatically effective amount to release the one or more N-glycans from a native or non-denatured glycoprotein or glycoproteins and/or from the cells of the cell composition after incubation for no more than 12 hours at a temperature between 35° C. and 39° C., optionally about 37° C.

24. The method of embodiment 23, wherein the enzymatically effective amount is an amount to release the one or more N-glycans after incubation for no more than 15 minutes to 3 hours or 30 minutes to 2 hours, at a temperature between 25° C. and 39° C. or between 35° C. and 39° C., each inclusive, optionally about 37° C.

25. The method of embodiment 23 or embodiment 24, wherein the enzymatically effective amount of PNGase F releases greater than 50%, greater than 55%, greater than 60%, greater than 65%, greater than 70%, greater than 75%, greater than 80%, greater than 85%, greater than 90%, greater than 95%, greater than 99% of N-glycans present on the glycoprotein or glycoproteins and/or present on the surface of the cell composition.

26. The method of any of embodiments 1-25, wherein the conditions of the incubation are sufficient to effect release of greater than 50%, greater than 55%, greater than 60%, greater than 65%, greater than 70%, greater than 75%, greater than 80%, greater than 85%, greater than 90%, greater than 95%, greater than 99% N-glycans present on the surface of the test cell composition.

27. The method of any of embodiments 11-26, wherein the amount of N-glycosidase, optionally PNGase F, is 1 unit to 5000 units, 1 unit to 1000 units, 1 unit to 500 units, 1 unit to 250 units, 1 unit to 100 units, 1 unit to 50 units, 1 unit to 25 units, 25 units to 5000 units, 25 units to 1000 units, 25 units to 500 units, 25 units to 250 units, 25 units to 100 units, 25 units to 50 units, 50 units to 5000 units, 50 units to 1000 units, 50 units to 500 units, 50 units to 250 units, 50 units to 100 units, 100 units to 5000 units, 100 units to 1000 units, 100 units to 500 units, 100 units to 250 units, 250 units to 5000 units, 250 units to 1000 units, 250 units to 500 units, 500 units to 5000 units, 500 units to 1000 units, or 1000 units to 5000 units, each inclusive.

28. The method of any of embodiments 11-27, wherein the amount of N-glycosidase, optionally PNGase F, is greater than or greater than about or is or is about 1 unit, 5 units, 10 units, 15 units, 20 units, 25 units, 50 units, 100 units, 250 units, 500 units, 1000 units, 2500 units or 5000 units.

29. The method of embodiment 27 or embodiment 28, wherein one unit is an amount of the N-glycosidase, optionally PNGase F, sufficient to catalyze the deglycosolation of 1 nanomole of denatured Ribonuclease B (RNase B) in 30 minutes at 37° C.

30. The method of embodiment 27 or embodiment 28, wherein 500 units is an amount of the N-glycosidase, optionally PNGase F, sufficient to catalyze the deglycosylation of 10 μg of Ribonuclease B (RNase B) incubated in 1×PBS for 5-10 minutes at 37° C. or room temperature.

31. The method of any of embodiments 1-30, wherein the incubating the test composition is for an amount of time that between or between about 5 minutes and 12 hours, 30 minutes and 6 hours or 1 hour and 3 hours, each inclusive.

32. The method of any of embodiments 1-31, wherein the incubating the test composition is for at least or at least about or is or is about 5 minutes, about 10 minutes, about 15 minutes, 30 minutes, 1 hour, 2 hours 3 hours, 4 hours, 5 hours or 6 hours.

33. The method of any of embodiments 1-32, wherein the incubating the test composition is for about 30 minutes.

34. The method of any of embodiments 1-33, wherein the incubating the test composition is at a temperature between 25° C. and 39° C. or between 35° C. and 39° C.

35. The method of any of embodiments 1-35, wherein the incubating the test composition is at a temperature of about 37° C.

36. The method of any of embodiments 1-35, wherein the incubating the test composition is for about 30 minutes at a temperature of about 37° C.

37. The method of any of embodiments 1-36, wherein, prior to the determining the presence, absence, identity and/or level of glycans present in a sample, the method further comprises labeling glycans from the sample with a detectable label, optionally a fluorescent label.

38. The method of any of embodiments 14-37, wherein the label is a fluorescent label and the fluorescent label is or comprises 2-aminobenzamide (2-AB), 2-aminobenzoic acid (2-AA), 2-aminopyridine (PA), 2-Aminoacridone (AMAC), 2-aminonaphthalene trisulfonic acid (ANTS), and 1-aminopyrene-3,6,8-trisulfonic acid (APTS), 3-(Acetylamino)-6-aminoacridin (AA-Ac), 6-Aminoquinoline (6-AQ), 7-Aminomethyl-coumarin (AMC), 2-Amino (6-amido-biotinyl) pyridine (BAP), 9-Fluorenylmethoxycarbonyl (FMOC)-hydrazide, 1,2-Diamino-4,5-methylenedioxy-benzene (DMB), or o-Phenylenediamine (OPD).

39. The method of any of embodiments 14-38, wherein the fluorescent label comprises a
quinolinyl fluorophore.

40. The method of any of embodiments 14-39, wherein the fluorescent label comprises a carbamate tagging group.

41. The method of any of embodiments 14-40, wherein the fluorescent label comprises a basic tertiary amine.

42. The methods of any of embodiments 14-37 and 39-41, wherein the fluorescent label comprises a carbamate tagging group, a quinolone fluorophore, and a tertiary amine.

43. The method of any of embodiments 1-42, wherein, prior to determining the presence, absence, identity and/or level of the one or more glycans, the sample is subjected to glycan purification or enrichment.

44. The method of embodiment 43, wherein glycan purification or enrichment is carried out by solid phase extraction (SPE).

45. The method of any of embodiments 1-44, wherein determining the presence, absence, identity and/or level of the one or more glycans comprises subjecting the sample to mass spectrometry.

46. The method of embodiment 45, the mass spectrometry is electrospray ionization mass spectrometry (ESI-MS), turbospray ionization mass spectrometry, nanospray ionization mass spectrometry, thermospray ionization mass spectrometry, sonic spray ionization mass spectrometry, surface enhanced laser desorption ionization mass spectrometry (SELDI-MS) and matrix assisted laser desorption/ionization mass spectrometry (MALDI-MS).

47. The method of embodiment 45 or 46, wherein the mass spectrometry is MALDI-MS.

48. The method of any of embodiments 1-47, wherein determining the presence, absence, identity and/or level of glycans comprises subjecting the sample to liquid chromatography (LC) followed by mass spectrometry.

49. The method of embodiment 48, wherein the liquid chromatography is high performance liquid chromatography (HPLC), ultra-high performance liquid chromatography (UHPLC), or ultra performance liquid chromatography (UPLC).

50. The method of embodiment 48 or embodiment 49, wherein the liquid chromatography is ultra performance liquid chromatography (UPLC).

51. The method of any of embodiments 48-50, wherein the liquid chromatography and mass spectrometry are carried out online.

52. The method of any of embodiments 48-51, wherein the liquid chromatography is selected from normal phase (NP-), reverse phase (RP) and hydrophilic interaction chromatography (HILIC).

53. The method of any of embodiments 48-52, wherein the liquid chromatography is hydrophilic interaction chromatography (HILIC).

54. The method of any of embodiments 45-53, wherein the mass spectrometry comprises electrospray ionization mass spectrometry (ESI-MS), turbospray ionization mass spectrometry, nanospray ionization mass spectrometry, thermospray ionization mass spectrometry or sonic spray ionization mass spectrometry.

55. The method of any of embodiments 45-54, wherein the mass spectrometry comprises ESI-MS.

56. The method of any of embodiments 45-55, wherein the mass spectrometry comprises tandem mass spectrometry (MS/MS).

57. The method of any of embodiments 45-56, wherein the mass spectrometry comprises tandem ESI-mass spectrometry (ESI-MS/MS).

58. The method of any of embodiments 45-57, wherein the mass spectrometer that performs the mass spectrometry comprises one or more of a quadrupole, ion trap, time of flight (TOF), or Fourier transform ion cyclotron resonance mass analyzer.

59. The method of embodiment 58, wherein the mass spectrometer comprises an ion trap mass analyzer that is a three-dimensional quadrupole ion trap, a cylindrical ion trap, a linear quadrupole ion trap, or an Orbitrap mass analyzer.

60. The method of any of embodiments 45-59, wherein the mass spectrometer is a quadrupole-Orbitrap mass spectrometer.

61. The method of any of embodiments 1-60, wherein the determining the presence, absence, identity and/or level of the one or more glycans comprises analyzing one or more glycan structure or structures for branching, linkages between monosaccharides and/or location of monosaccharides.

62. The method of any of embodiments 1-61, wherein the one or more glycans comprises high mannose N-glycans, bisected and Sialyl Lewis' N-glycans, and/or N-acetyl lactosamine containing N-glycans.

63. The method of any of embodiments 1-62, wherein the one or more glycans comprises a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

64. The methods of any of embodiments 1-63, wherein the determining the presence, absence, identity and/or level of glycans present in the sample comprises determining the presence, absence, identity and/or level of at least 25, at least 50, at least 60, at least 70, at least 80, at least 90, at least 100, or at least 200 different species of glycans.

65. The method of any of embodiments 1-64, wherein the presence or level of a glycan species present in the sample is determined if at least 100 amol, at least 500 amol, at least 1 fmol, at least 5 fmol, or at least 10 fmol of the glycan species is present in the sample.

66. The method of any of embodiments 1-65, wherein the presence or level of a glycan species present in the sample is determined if glycan species makes up at least 0.00001%, 0.00005%, 0.0001%, 0.0005%, 0.001%, 0.005%, or 0.01% of the total glycans in the sample.

67. The method of any of embodiments 62-65, wherein the species of glycans are species of N-glycans.

68. The method of any of embodiments 1-67, wherein the test cell composition is or comprises at least a portion of a source cell composition comprising the plurality of cells.

69. The method of any of embodiments 1-68, wherein the cells comprise mammalian cells or the test cell composition comprises mammalian cells.

70. The method of any one of embodiments 1-69, wherein the cells comprise human cells or the test cell composition comprises human cells.

71. The method of any one of embodiments 1-70, wherein the cells comprise stem cells or the test cell composition comprises stem cells.

72. The method of embodiment 71, wherein the stem cell is an induced pluripotent stem cell (iPSC).

73. The method of any of embodiments 1-70, wherein the test cell composition comprises cells present in an apheresis product or a leukapheresis product or cells derived therefrom.

74. The method of any of embodiments 1-70, and 73, wherein:
the cells comprise immune cells, white blood cells, peripheral blood mononuclear cells (PBMC), lymphocytes, or unfractionated T cells; or
the test cell composition comprises immune cells, white blood cells, peripheral blood mononuclear cells (PBMC), lymphocytes, or unfractionated T cells.

75. The method of any one of embodiments 1-74, wherein the cells comprise an immune cell or the test cell composition comprises immune cells.

76. The method of embodiment 75, wherein the immune cell is a T cell, B cell, macrophage, neutrophil, natural killer (NK) cell or dendritic cell.

77. The method of any of embodiments 1-76, wherein the cells comprise T cells that are CD4+ and/or CD8+ T cells or the test cell composition comprises T cells that are CD4+ and/or CD8+ T cells.

78. The method of any of embodiments 1-77, wherein the test cell composition comprises:
cells isolated from a biological sample by immunoaffinity-based methods; and/or
cells transduced with a viral vector encoding a recombinant protein; and/or
cell incubated in the presence of one or more test agents, optionally one more peptide, protein, polypeptide, nucleic acid, small molecule; and/or
cells activated and/or expanded in the presence of one or more stimulating conditions; and/or
cryopreserved cells and/or cells comprising a cryoprotectant; and/or
cells formulated for administration to a subject, optionally in the presence of a pharmaceutically acceptable excipient.

79. The method of embodiment 78, wherein the test agent is a candidate for modulating the growth, proliferation, viability, differentiation, intracellular signaling, activation and/or expansion of one or more cells in the test cell composition.

80. The method of embodiment 78 or embodiment 79, wherein the stimulating condition comprises incubation with a stimulatory reagent capable of activating one or more intracellular signaling domains of one or more components of a TCR complex and/or one or more intracellular signaling domains of one or more costimulatory molecules.

81. The method of embodiment 80, wherein the stimulatory reagent comprises a primary agent that specifically binds to a member of a TCR complex and a secondary agent that specifically binds to a T cell costimulatory molecule.

82. The method of embodiment 81, wherein the primary agent specifically binds to CD3 and/or the costimulatory molecule is selected from the group consisting of CD28, CD137 (4-1-BB), OX40, or ICOS.

83. The method of any of embodiments 80-82, wherein stimulatory reagent comprises an anti-CD3 antibody or antigen binding fragment thereof and an anti-CD28 antibody or an antigen-binding fragment thereto.

84. The method of any of embodiments 80-83, wherein the primary and secondary agents comprise antibodies and/or are present on the surface of a solid support.

85. The method of embodiment 84, wherein the solid support is or comprises a bead. 86. The method of any of embodiments 1-85, wherein the cells express a recombinant receptor or the test composition comprises cells expressing a recombinant receptor.

87. The method of embodiment 86, wherein the recombinant receptor is or comprises a chimeric receptor and/or a recombinant antigen receptor.

88. The method of embodiment 86 or embodiment 87, wherein the recombinant receptor is capable of binding to a target antigen that is associated with, specific to, and/or expressed on a cell or tissue of a disease, disorder or condition.

89. The method of embodiment 88, wherein the disease, disorder or condition is an infectious disease or disorder, an autoimmune disease, an inflammatory disease, or a tumor or a cancer.

90. The method of embodiment 88 or embodiment 89, wherein the target antigen is a tumor antigen.

91. The method of any of embodiments 88-90, wherein the target antigen is selected from among ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

92. The method of any of embodiments 88-91, wherein the recombinant receptor is or comprises a functional non-TCR antigen receptor or a TCR or antigen-binding fragment thereof.

93. The method of any of embodiments 88-92, wherein the recombinant receptor is a chimeric antigen receptor (CAR).

94. A method of assaying a cell composition, the method comprising:
(a) assessing the cell surface glycan profile in a sample from a test cell composition comprising a plurality of cells according to the method of any of embodiments 1-91; and
(b) comparing the cell surface glycan profile of the sample to the cell surface glycan profile of a reference sample.

95. A method of assaying a cell composition, the method comprising comparing the cell surface glycan profile of a sample compared to the cell surface profile of a reference sample, wherein cell surface glycan profile of the sample is or has been determined according to the method of any of embodiments 1-93 from a test cell composition comprising a plurality of cells.

96. The method of embodiment 94 or embodiment 95, wherein the cell surface glycan profile comprises at least 25, at least 50, at least 60, at least 70, at least 80, at least 90, at least 100, or at least 200 different species of glycans, optionally different species of N-glycans.

97. The method of any of embodiments 94-96, wherein the cell surface glycan profile comprises high mannose N-glycans, bisected and Sialyl Lewis' N-glycans, and/or N-acetyl lactosamine containing N-glycans.

98. The method of embodiment 94-97, wherein the cell surface glycan profile comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

99. The method of any of embodiments 94-98, wherein the cell surface glycan profile comprises the glycans in Table E1 or a subset thereof.

100. The method of any of embodiments 94-99, wherein the reference sample is a reference standard comprising a release specification, a label requirement or a compendia specification.

101. The method of any of embodiments 94-100, wherein the cell composition is released for treatment of a subject only if the cell surface glycan profile of the composition is substantially the same as the reference sample and/or if the percent of a target glycan or each of a plurality of target glycans to the total glycans present in the sample differs by no more than 25%, no more than 20% or no more than 10% from the percent of the target glycan or each of the plurality of target glycans to the total glycans present in the reference sample.

102. The method of embodiment 101, wherein the target glycans comprise at least 25, at least 50, at least 60, at least 70, at least 80, at least 90, at least 100, or at least 200 different species of glycans.

103. The method of embodiment 101 or embodiment 102, wherein the target glycan or glycans comprise high mannose N-glycans, bisected and Sialyl Lewis' N-glycans, and/or N-acetyl lactosamine containing N-glycans.

104. The method of any of embodiments 101-103, wherein the target glycan or glycans comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

105. The method of any of embodiments 101-104, wherein the target glycan or glycans comprise the glycans present in Table E1 or a subset thereof.

106. The method of any of embodiments 101-105, wherein the target glycan or glycans comprise the glycans detectable in the cell surface glycan profile.

107. The method of any of embodiments 95-99, wherein the reference sample is a cell surface glycan profile from a different cell composition.

108. The method of embodiment 107, wherein the different cell composition is from a different stage of a manufacturing process for producing the test cell composition or a source cell composition from which the test composition has been derived or obtained, wherein the stage of the manufacturing process optionally is a prior stage of the manufacturing process.

109. The method of embodiment 108, wherein the manufacturing process comprises one or more stages selected from:
cells isolated from a biological sample by leukapheresis or apheresis;
cells selected from a biological sample by immunoaffinity-based methods; and/or
cells introduced with a recombinant nucleic acid, optionally a viral vector encoding a recombinant protein; and/or
cell incubated in the presence of one or more test agents, optionally one more peptide, protein, polypeptide, nucleic acid, small molecule; and/or
cells activated and/or expanded in the presence of one or more stimulating conditions; and/or
cryopreservation of cells in the presence of a cryoprotectant; and/or
cells formulated for administration to a subject, optionally in the presence of a pharmaceutically acceptable excipient.

110. The method of any of embodiments 107-109, wherein a difference in the glycan profile between the test composition and reference sample indicates one or more differences is present in the cells among the cells produced at the different stages in the manufacturing process.

111. The method of embodiment 110, wherein the difference in the glycan profile exists if the cell surface glycan profile of the composition is substantially different from the reference sample and/or if the percent of a target glycan or each of the one or more target glycans to the total glycans present in the sample differs by greater than or greater than about 10%, 20%, 30%, 40%, 50%, 60%, 70%, 80%, 90% or more from the percent of the target glycan or each of the one or more target glycans to the total glycans present in the reference sample.

112. The method of embodiment 111, wherein the target glycans comprise at least 25, at least 50, at least 60, at least 70, at least 80, at least 90, at least 100, or at least 200 different species of glycans, optionally wherein the species of glycans are N-glycans.

113. The method of embodiment 110 or embodiment 112, wherein the target glycan or glycans comprise high mannose N-glycans, bisected and Sialyl Lewis$^x$ N-glycans, and/or N-acetyl lactosamine containing N-glycans.

114. The method of any of embodiments 111-113, wherein the target glycan or glycans comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

115. The method of any of embodiments 111-114, wherein the target glycan or glycans comprise the glycans present in Table E1 or a subset thereof.

116. The method of any of embodiments 111-115, wherein the target glycan or glycans comprise the glycans detectable in the cell surface glycan profile.

117. The method of any of embodiments 111-116, wherein the one more differences is associated with a functional activity or phenotype of the cells.

118. The method of embodiment 117, wherein the functional activity or phenotype comprises one or more of masking of a cell surface marker, a metabolic activity, differentiation state, proliferative or expansion capacity, activation state, cytolytic activity, signaling activity, an adhesion property, or a homing property.

119. The method of any of embodiments 111-118, further comprising modulating or changing the process for manufacturing the cell composition.

120. The method of any of embodiments 108-119, wherein the reference standard comprises an average or median of the presence, absence, identity and/or level of the one or more target glycan or glycans among a plurality of compositions produced by the process.

121. A method for manufacturing a cell composition, comprising
incubating and/or contacting an input composition comprising a plurality of cells with one or more agents and/or under one or more conditions thereby generating the cell composition,
wherein the cell composition comprises one or a plurality of cells that are genetically, phenotypically, and/or functionally different from one or a plurality of cells from the input composition, and
wherein the cell composition comprises one or a plurality of cells that comprise a cell surface glycan profile comprising one or more target glycans and/or each of the one or more target glycans in the cell surface glycan profile differs by no more than 25% from the cell surface glycan profile or each of the one or more target glycans to the total glycans present in a reference sample, wherein the cell surface glycan profile comprises glycans released from the surface of cells in the cell composition.

122. The method of embodiment 121, wherein the cell surface glycan profile or the one or more target glycans is determined according to the method of any of embodiments 1-93.

123. The method of embodiment 121 or embodiment 122, wherein the cell composition comprises cells comprising a recombinant nucleic acid.

124. The method of any of embodiments 121-123, wherein prior to, during, or subsequent to the incubation and/or contacting, the method comprises one or more steps selected from cell washing, dilution, isolation, selection, separation, cultivation, stimulation, introduction of a recombinant nucleic acid, cryopreservation, formulation and/or packaging.

125. The method of any of embodiments 121-124, wherein prior to, during, or subsequent to incubation and/or contacting, the method comprises one or more steps selected from:

isolating cells from a biological sample by leukapheresis or apheresis;

isolating cells from a biological sample by immunoaffinity-based methods; and/or introducing cells with a recombinant nucleic acid, optionally a viral vector encoding a recombinant protein; and/or incubating cells in the presence of one or more agent, optionally one more peptide, protein, polypeptide, nucleic acid, small molecule; and/or activating cells and/or expanded in the presence of one or more stimulating conditions; and/or cryopreserving cells in the presence of a cryoprotectant; and/or formulating cells for administration to a subject, optionally in the presence of a pharmaceutically acceptable excipient.

126. The method of any of embodiments 121-125, wherein the one or more agents or conditions comprises presence or concentration of serum; time in culture; presence or amount of a stimulating agent; the type or extent of a stimulating agent; presence or amount of amino acids; temperature; the source or cell types of the source composition; the ratio or percentage of cell types in the source composition, optionally the CD4+/CD8+ T cell ratio; the presence or amount of beads; cell density; static culture; rocking culture; perfusion; the type of viral vector; the vector copy number; the presence of a transduction adjuvant; cell density of the source composition in cryopreservation; the extent of expression of the recombinant receptor; or the presence of a compound to modulate cell phenotype.

127. The method of any of embodiments 121-126, wherein the one or more agents or conditions comprises stimulating conditions, a peptide, a protein, a polypeptide, a nucleic acid, a small molecule, and/or a recombinant nucleic acid, optionally a viral vector encoding a recombinant protein.

128. The method of any of embodiments 121-127, wherein the agent modulates the growth, proliferation, viability, differentiation, intracellular signaling, activation and/or expansion of one or more cells in the cell composition.

129. The method of any of embodiments 125-127, wherein the stimulating condition comprises incubation with a stimulatory agent capable of activating one or more intracellular signaling domains of one or more components of a TCR complex and/or one or more intracellular signaling domains of one or more costimulatory molecules.

130. The method of embodiment 129, wherein the stimulatory agent comprises a primary agent that specifically binds to a member of a TCR complex and a secondary agent that specifically binds to a T cell costimulatory molecule.

131. The method of embodiment 130, wherein the primary agent specifically binds to CD3 and/or the costimulatory molecule is selected from the group consisting of CD28, CD137 (4-1-BB), OX40, or ICOS.

132. The method of any of embodiments 129-131, wherein stimulatory agent comprises an anti-CD3 antibody or antigen binding fragment thereof and/or an anti-CD28 antibody or an antigen-binding fragment thereto.

133. The method of any of embodiments 129-132, wherein the primary and secondary agents comprise antibodies and/or are present on the surface of a solid support.

134. The method of embodiment 133, wherein the solid support is or comprises a bead.

135. The method of any of embodiments 125-127 and 129-134, wherein the stimulating conditions comprises the presence of one or more cytokines, optionally IL-2, IL-15 and/or IL-7.

136. The method of any of embodiments 121-135, wherein the reference sample is a reference standard comprising a release specification, a label requirement or a compendia specification.

137. The method of any of embodiments 121-136, wherein the reference sample comprises an average or median of the presence, absence, identity and/or level of the one or more target glycan or glycans among a plurality of compositions produced by the incubating and/or the contacting the source composition with the one or more agents and/or under the one or more conditions.

138. The method of any of embodiments 121-137, wherein the cell surface glycan profile comprising the one or more target glycans or each of the one or more target glycans differs by no more than or about 20%, no more than or about 15%, no more than or about 10% or no more than or about 5% from the cell surface glycan profile or each of the one or more target glycans to the total glycans present in the reference sample.

139. The method of any of embodiments 121-138, wherein the target glycans comprise at least 25, at least 50, at least 60, at least 70, at least 80, at least 90, at least 100, or at least 200 different species of glycans, optionally wherein the species of glycans are N-glycans.

140. The method of any of embodiments 121-139, wherein the target glycan or glycans comprise high mannose N-glycans, bisected and Sialyl Lewis$^X$ N-glycans, and/or N-acetyl lactosamine containing N-glycans.

141. The method of any of embodiments 121-140, wherein the target glycan or glycans comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

142. The method of any of embodiments 121-141, wherein the target glycan or glycans comprise the glycans present in Table E1 or a subset thereof 143. The method of any of embodiments 121-142, wherein the target glycan or glycans comprise the glycans detectable in the cell surface glycan profile.

144. A method for screening one or more test agents or conditions on a cell composition, comprising:
(a) assessing a cell surface glycan profile in a sample from a test cell composition, wherein the test cell composition is or is derived from a source composition that has been incubated or treated in the presence of one or more test agents or conditions; and
(b) comparing the cell surface glycan profile of the sample to the cell surface glycan profile of a reference sample, the reference sample comprising one or more target glycans.

145. A method for screening one or more test agents or conditions on a cell composition, comprising comparing the cell surface glycan profile of a sample compared to the cell surface glycan profile of a reference sample, wherein the sample is from a test cell composition that is or is derived from a source composition that has been incubated or treated in the presence of one or more test agents or conditions.

146. The method of embodiment 144 or embodiment 145, wherein the cell surface glycan profile comprises the presence, absence, identity and/or level of one or more glycans in the sample.

147. The method of any of embodiments 145-146, wherein the cell surface glycan profile is determined according to the method of any of embodiments 1-93.

148. The method of any of embodiments 144-147, wherein the reference sample is derived from a composition incubated or treated under the same or substantially the same conditions as the test cell composition or source composition except in the absence of treating in the presence of the one or more test agents or conditions or in the presence of one or more alternative test agents or conditions.

149. The method of any of embodiments 144-147, wherein the reference sample comprises an average or median of the presence, absence, identity and/or level of the one or more target glycan or glycans among a plurality of compositions incubated or treated in the presence of the one or more test agents or conditions.

150. The method of any of embodiments 144-149, wherein the one or more test agents or conditions comprises presence or concentration of serum; time in culture; presence or amount of a stimulating agent; the type or extent of a stimulating agent; presence or amount of amino acids; temperature; the source or cell types of the source composition; the ratio or percentage of cell types in the source composition, optionally the CD4+/CD8+ T cell ratio; the presence or amount of beads; cell density; static culture; rocking culture; perfusion; the type of viral vector; the vector copy number; the presence of a transduction adjuvant; cell density of the source composition in cryopreservation; the extent of expression of the recombinant receptor; or the presence of a compound to modulate cell phenotype.

151. The method of any of embodiments 144-150, wherein the one or more test agents or conditions comprises one or more compounds from a library of test compounds.

152. The method of any of embodiments 144-151, wherein the target glycans comprise at least 25, at least 50, at least 60, at least 70, at least 80, at least 90, at least 100, or at least 200 different species of glycans, optionally wherein the species of glycans are N-glycans.

153. The method of any of embodiments 144-152, wherein the target glycan or glycans comprise high mannose N-glycans, bisected and Sialyl Lewis' N-glycans, and/or N-acetyl lactosamine containing N-glycans.

154. The method of any of embodiments 144-153, wherein the target glycan or glycans comprise a fucosylated biantennary complex glycan having no reducing end terminal galactose residues, a fucosylated biantennary complex glycan having one reducing end terminal galactose residue, a fucosylated biantennary complex glycan having two reducing end terminal galactose residues, a biantennary complex glycan having no reducing end terminal galactose residues, a biantennary complex glycan having one reducing end terminal galactose residue, a biantennary complex glycan having two reducing end terminal galactose residues, a fucosylated biantennary complex glycan having two galactose residues and one N-acetylneuraminic acid residue, a fucosylated biantennary complex glycan having two galactose residues and two N-acetylneuraminic acid residues, a biantennary complex glycan having two galactose residues and two N-acetylneuraminic acid residues, a high mannose glycan having five mannose residues, a high mannose glycan having six mannose residues, a high mannose glycan having seven mannose residues, a high mannose glycan having eight mannose residues, and/or a high mannose glycan having nine mannose residues.

155. The method of any of embodiments 144-154, wherein the target glycan or glycans comprise the glycans present in Table E1 or a subset thereof.

156. The method of any of embodiments 144-155, wherein the target glycan or glycans comprise the glycans detectable in the cell surface glycan profile.

157. The method of any of embodiments 144-156, comprising selecting the one or more test agent or conditions for incubating or treating the cells if the comparison indicates the cell surface glycan profile of the sample or each of the one or more target glycans is substantially the same as the reference sample and/or if the comparison indicates the cell surface glycan profile comprising the one or more target glycans or each of the one or more target glycans differs by no more than or about 20%, no more than or about 15%, no more than or about 10% or no more than or about 5% from the cell surface glycan profile or each of the one or more target glycans to the total glycans present in the reference sample.

158. The method of any of embodiments 144-156, comprising repeating the method with one or more further test agent or condition if the comparison indicates the cell surface glycan profile of the sample or each of the one or more target glycans is substantially different from the reference sample and/or if the comparison indicate the cell surface glycan profile comprising the one or more target glycans or each of the one or more target glycans differs by greater than or greater than about 10%, 20%, 30%, 40%, 50%, 60%, 70%, 80%, 90% or more from the cell surface glycan profile or each of the one or more target glycans to the total glycans present in the reference sample.

159. The method of any of embodiments 144-156, wherein the test agent is a candidate for modulating the growth, proliferation, viability, differentiation, activation and/or expansion, of one or more cells in the test cell composition.

160. The method of any of embodiments 144-159, wherein the test cell composition comprises cells comprising a recombinant nucleic acid.

161. The method of any of embodiments 125-160, wherein the recombinant nucleic acid encodes a recombinant protein, optionally a recombinant receptor.

162. The method of embodiment 160, wherein the recombinant receptor is or comprises a chimeric receptor and/or a recombinant antigen receptor.

163. The method of embodiment 161 or embodiment 162, wherein the recombinant receptor is capable of binding to a target antigen that is associated with, specific to, and/or expressed on a cell or tissue of a disease, disorder or condition.

164. The method of embodiment 163, wherein the disease, disorder or condition is an infectious disease or disorder, an autoimmune disease, an inflammatory disease, or a tumor or a cancer.

165. The method of embodiment 163 or embodiment 164, wherein the target antigen is a tumor antigen.

166. The method of any of embodiments 163-165, wherein the target antigen is selected from among ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

167. The method of any of embodiments 163-166, wherein the recombinant receptor is or comprises a functional non-TCR antigen receptor or a TCR or antigen-binding fragment thereof.

168. The method of any of embodiments 163-167, wherein the recombinant receptor is a chimeric antigen receptor (CAR).

169. The method of any of embodiments 121-168, wherein the cells comprise mammalian cells or the test cell composition comprises mammalian cells.

170. The method of any one of embodiments 121-169, wherein the cells comprise human cells or the test cell composition comprises human cells.

171. The method of any one of embodiments 121-168, wherein the cells comprise stem cells or the test cell composition comprises stem cells.

172. The method of embodiment 171, wherein the stem cell is an induced pluripotent stem cell (iPSC).

173. The method of any of embodiments 121-170, wherein the composition or test cell composition comprises cells present in an apheresis product or a leukapheresis product or cells derived therefrom.

174. The method of any of embodiments 121-170 and 1713, wherein:

the cells comprise immune cells, white blood cells, peripheral blood mononuclear cells (PBMC), lymphocytes, or unfractionated T cells; or the test cell composition comprises immune cells, white blood cells, peripheral blood mononuclear cells (PBMC), lymphocytes, or unfractionated T cells.

175. The method of any one of embodiments 121-174, wherein the cells comprise an immune cell or the test cell composition comprises immune cells.

176. The method of embodiment 175, wherein the immune cell is a T cell, B cell, macrophage, neutrophil, natural killer (NK) cell or dendritic cell.

177. The method of any of embodiments 121-176, wherein the cells comprise T cells that are CD4+ and/or CD8+ T cells or the test cell composition comprises T cells that are CD4+ and/or CD8+ T cells.

178. The method of any of embodiments 1-177, wherein the cells are primary cells.

179. A method of detecting a presence, absence, identity, and/or level of one or more substances in a cell composition, the method comprising:

(a) assessing the cell surface glycan profile in a sample from a test cell composition comprising a plurality of cells according to the method of any of embodiments 1-93, wherein the plurality of cells are from or are derived from a cell type; and (b) identifying one or more non-native glycans in the cell surface glycan profile that are not synthesized and/or expressed by cells of the cell type.

180. The method of embodiment 179, wherein the cell type is human.

181. The method of embodiment 179 or 180, wherein the cell type is an immune cell.

182. the method of any of embodiments 180 or 181, wherein the cell type is a T cell.

183. The method of any of embodiments 179-182, wherein the test cell composition was produced by culturing and/or incubating the plurality of cells in the presence of the substance, said substance comprising at least one protein comprising one or more non-native glycans.

184. The method of embodiment 183, wherein the at least one protein is an albumin, a growth factor, a cytokine, a chemokine, an insulin or insulin-like peptide, a transferrin, or a superoxide dismutase.

185. The method of embodiment 183 or 184, wherein the at least one protein is a recombinant protein.

186. The method of any of embodiments 183-185, wherein the one or more non-native glycans and/or the at least one protein are present in a serum.

187. The method of embodiment 186, wherein the serum is fetal bovine serum (FBS), bovine calf serum (BCS), newborn calf serum (NBCS), horse serum, goat serum, lamb serum, donkey serum, or porcine serum.

188. The method of any of embodiments 179-187, wherein the one or more non-native glycans and/or the at least one protein are (i) not produced by and/or (ii) not expressed on the surface of cells from the same order, family, genus, or species as the cells of the plurality.

189. The method of any of embodiments 179-188, wherein the one or more non-native glycans comprise a non-human glycan.

190. The method of any of embodiments 179-189, wherein the identifying the one or more non-native glycans comprises comparing the surface glycan profile to a reference glycan profile, wherein the reference sample is a glycan profile from a source containing the one or more non-native glycans.

191. The method of embodiment 189 or 190, wherein the reference glycan profile is generated from a reference sample comprising a substance that has not been contacted, incubated, and/or exposed to the cells of the plurality, optionally wherein the substance is or comprises a media, a serum, or a component thereof, or is a protein or recombinant protein thereof.

VI. EXAMPLES

The following examples are included for illustrative purposes only and are not intended to limit the scope of the invention.

Example 1: Mapping Surface N-Linked Glycans of a Cell Composition

To map the cell surface N-linked glycan profile of a cell composition, exemplary cryopreserved T cell compositions containing cells expressing a chimeric antigen receptor (CAR) were individually thawed, diluted 1:10 in cell culture media heated to 37° C., and a sample of 1-2.5×10$^6$ cells was transferred to a fresh tube.

The transferred cell sample was centrifuged and washed in phosphate buffered saline (PBS), followed by reconstitution of the cell suspension with approximately 198 μl PBS. Approximately 2 μL PNGase F PRIME (N-Zyme Scientifics; available from Bulldog Bio, Catalog No. NZPP050) was added to the cell suspension containing whole, intact cells, followed by incubation for 30 minutes at 37° C. with gentle mixing. To obtain released surface N-glycans, the cell suspension was centrifuged and the supernatant was collected into a clean tube that was immediately evaporated to dryness with vacuum centrifugation.

The dried down N-glycans were reconstituted in 30 μl water and 5 μL of a labeling reagent composed of an N-hydroxysuccinimide (NHS) carbamate tagging group, a quinolone fluorophore, and a basic tertiary amine (Glycoworks™ RapiFluor-MS™ label, Catalog No. 715004793, Waters Corporation, MA) was added. The sample was mixed, incubated for approximately 5 minutes at room temperature, following by quenching of the label by adding approximately 365 μl acetonitrile to the sample. The sample was mixed and centrifuged. Solid phase extraction (SPE) was carried out on the sample to further clean up the N-glycans prior to further analysis. The N-glycan sample was evaporated to dryness with a vacuum centrifuge and then resuspended in appropriate diluent for analysis.

Glycans were separated using HILIC liquid chromatography and detected by fluorescence (Waters ACQUITY I-Class) (HILIC-FLR) and mass spectrometry (positive electrospray ionization (ESI), Q-Exactive™ HF (Thermo Scientific)), i.e., HILIC-ESI-MS, for relative quantification and identification.

Table E1 set forth the retention time(s) (RT), as well as the monoisotopic mass and the mass of the +2, +3, and/or +4 charge states, for exemplary sugars detected using this method.

TABLE E1

| Retention Time and Mass of Exemplary Glycans | | | | | |
|---|---|---|---|---|---|
| Sugar | RT | +2 | +3 | +4 | Mass |
| A2G0F | 13.15 | 887.8699 | | | 1773.74 |
| A1G1F | 14, 14.5 | 867.36 | | | 1732.72 |
| M5 | 14.35 | 773.81 | | | 1545.62 |
| A2G1 | 14.88 | 895.8674 | | | 1789.735 |
| A2G1F | 15.4 & 15.9 | 968.9 | | | 1935.8 |
| A1S1 | 16.1 | 939.8756 | | | 1877.751 |
| A3G1F | 16.4, 17.1 | 1070.437 | | | 2138.873 |
| A4G0F | | 1090.95 | | | 2179.9 |
| A1S1F | 16.5 | 1012.905 | | | 2023.81 |
| m6 | 16.9 | 854.8407 | | | 1707.681 |
| A2G1S1 | 16.9, 17.4 | 1041.417 | | | 2080.833 |
| M5A1G0F/M4A1G1F | 16.9 | 948.3837 | | | 1894.767 |
| m6 | 17.1 | 854 | | | 1706 |
| A2G2 | 17.2 | 976.89 | | | 1951.78 |
| A2G1S1F | 17.6, 18.3 | 1114.445 | | | 2226.889 |
| M4A1S1 | 18.3? | 1020.9 | | | 2039.8 |
| A3G2 | 17.9 | 1078.43 | | | 2154.86 |
| A2G2F | 18.14 | 1049.92 | | | 2097.84 |
| M5A1G1 | 18.5 | 956.3811 | | | 1910.762 |
| A3G2F | 18.7, 19.6 | 1151.464 | | | 2300.928 |
| M5A1G1F | 18.85, 19.9 | 1029.411 | | | 2056.821 |
| M4A1S1F | 20.6 | 1093.933 | | | 2185.865 |
| A2G2S1 | 19.3-19.5 & 20.75 | 1122.443 | | | 2242.886 |
| M7 | 19.7 | 935.8676 | | | 1869.735 |
| A2G2S1F | 20.1, 20.3, 21.5 | 1195.473 | | | 2388.945 |
| M5A1S1 | 20.6, 21.9 | 1101.93 | | | 2201.861 |
| A2G2S1F | 21.2-21.6 | 1195.47 | | | 2388.94 |
| M5A1S1F | 22 | 1174.96 | | | 2347.92 |
| A2G2S2 | 21.6, 22.7 | 1267.994 | | | 2533.987 |
| M8 | 22.1 | 1016.895 | | | 2031.789 |
| A3G2S1F(bisected) | | 1297.01 | | | 2592.02 |
| | | 1039.884 | | | 2077.769 |
| A2G2S2F | 22.3 | 1341.021 | | | 2680.042 |
| M5A1S1F | 22.8 | 1174.96 | | | 2347.92 |
| A2G2S2F | 23.35 | 1340.979 | | | 2679.959 |
| A2S1F2 | 23.45 | 1268.5 | | | 2535 |

TABLE E1-continued

Retention Time and Mass of Exemplary Glycans

| Sugar | RT | +2 | +3 | +4 | Mass |
|---|---|---|---|---|---|
| A3G3S1 | 23.6 | 1305.01 | | | 2608.02 |
| A2S2 | 23.7 | 1267.994 | | | 2533.987 |
| M9 | 23.95 | 1097.922 | | | 2193.844 |
| A3G3S1F | 24 | 1378.04 | | | 2754.08 |
| A2G2S2F | 24.4 | 1341.021 | | | 2680.042 |
| A3G3S1F | 24.6 | 1378.042 | | | 2754.083 |
| A3G2S2F(bisected) | 25.02 | 1442.56 | 962.04 | | 2883.12 |
| A2S2F2 | 25.25 | 1414.05 | | | 2826.1 |
| a3g3s2 | | 1450.56 | | | 2899.12 |
| M9 + hex | 25.65 | 1178.949 | | | 2355.897 |
| A3G3S2F | 25.7, 26.3, 26.6 | | 1016.061 | | 3045.183 |
| A4G4S1F(Or A3 w/ LacNac) | 26.7 | | 1040.74 | | 3119.221 |
| A3G3S1F | 26.7 | 1378.04 | | | 2754.08 |
| A3S3 | 27.65 | | 1064.407 | | 3190.221 |
| A4G4S2F(or A3 w/ LacNac) | 27.95 | | 1137.772 | | 3410.315 |
| A3S3F2 | | | 1161.78 | | 3482.34 |
| A3S3F | 27.2, 28.1 | | 1113.093 | | 3336.28 |
| A4G4S2F2(or A3 w/ LacNac) | | | 1186.46 | | 3556.38 |
| A4G4S3F(or A3 w LacNac) | 29.22 | | 1234.804 | | 3701.411 |
| A3S4F | 29.5 | | 1210.126 | | 3627.379 |
| A3S4F2 | 30 | | 1258.812 | | 3773.435 |
| A4S4F | 31 | | 1331.84 | | 3992.52 |
| A4G4S3F w 1lacnac(or A3 w 2LacNac) | 31 | | 1356.52 | | 4066.56 |
| A4G4S2F w 2lacnac | 31 | | 1381.2 | | 4140.6 |
| A4G4S5F | | | 1428.87 | | 4283.61 |
| A4G4S4F w 1lacnac | 32 | | 1453.55 | | 4357.65 |
| A4G4S3F w 2lacnac(or A3 w 3LacNac) | 33 | | 1478.23 | | 4431.69 |
| a4g4s2f w 3lacnac | 34 | | 1502.91 | | 4505.73 |
| A4G4S4F w 2lacnac | 34 | | 1575.27 | | 4722.81 |
| A4G4S3F w 3lacnac | 35 | | 1599.95 | | 4796.85 |
| A4G4S5F + 2lacnac | | | 1672.3 | | 5013.9 |
| A4G4S4 w 3lacnac | 35.3 | | 1696.98 | | 5087.94 |
| A4G4S3F w 4lacnac | | | 1721.65 | 1291.49 | 5161.959 |
| | | | 1527.25 | 1145.939 | 4579.757 |
| A4G4S4F w 4lacnac | 36 | | | 1364.264 | 5453.058 |
| A4G4S4F w 3lacnac | | | | 1272.98 | 5087.919 |
| | | | | 1291.49 | 5161.959 |
| A4G4S5F W 3lacnac | | | | 1345.754 | 5379.015 |
| a4G4S3F W 5lacnac | | | | 1382.773 | 5527.091 |
| A4G4S2F w 6lacnac | | | | 1401.281 | 5601.125 |
| A4G4S4F w 5lacnac | | | | 1455.547 | 5818.189 |
| A4G4S5F w 4lacnac | | | | 1437.039 | 5744.154 |
| A4G4S2F w 7lacnac | | | | 1492.562 | 5966.247 |
| | | | | 1419.536 | 5674.143 |
| A4G4S4F w 6lacnac | | | | 1546.83 | 6183.321 |
| A4G4S3F w 7lacnac | | | | 1565.34 | 6257.359 |
| A4G4S4F w 7lacnac | 40 | | | 1638.113 | 6548.452 |
| A4G4S3F w 8lacnac | 40 | | | 1656.626 | 6622.506 |
| A4G4S4f w 8 lacnac | | | | 1729.404 | 6913.617 |
| A4G4S3F w 9lacnac | | | | 1747.902 | 6987.607 |

Figure 2:
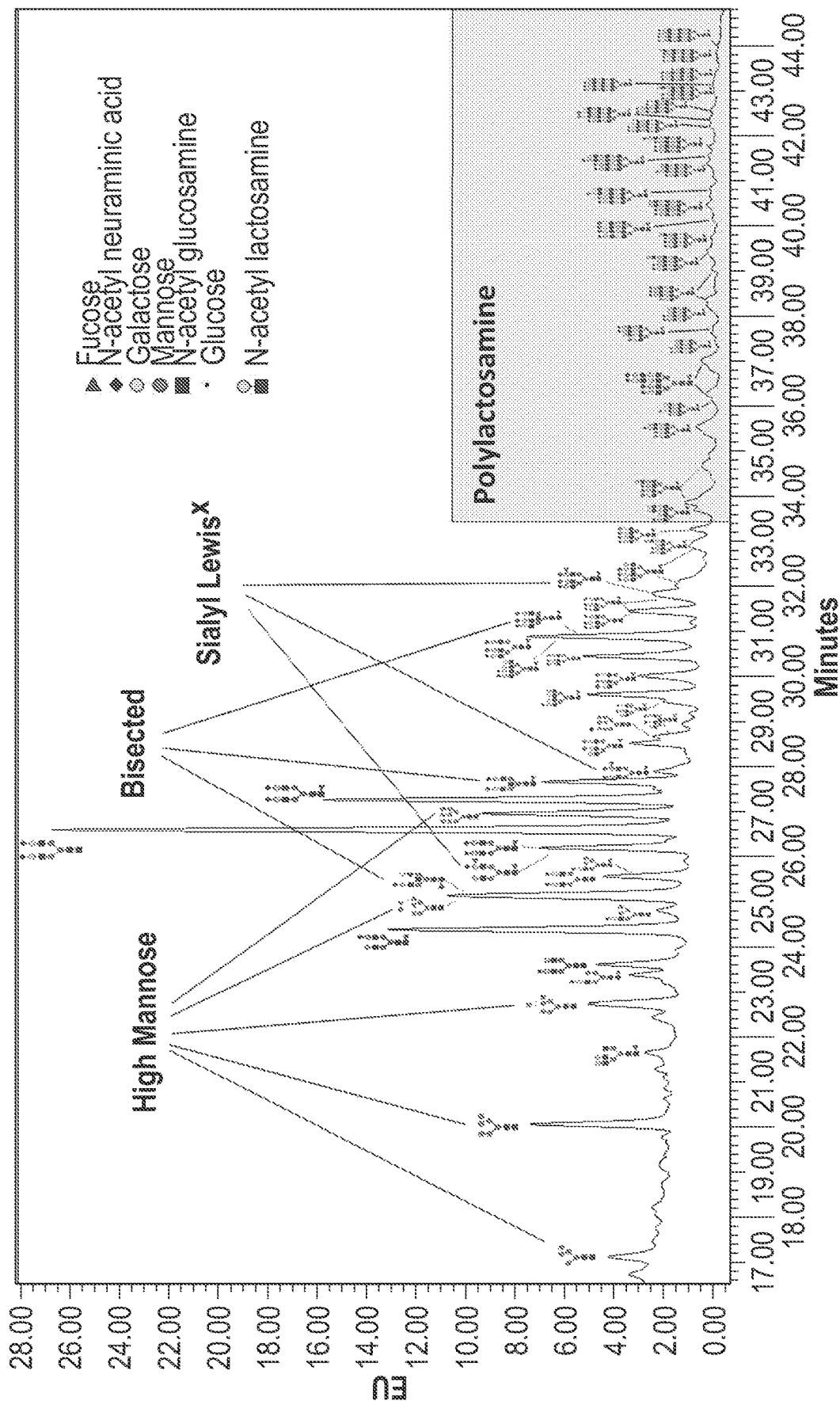
FIG. 2 shows a surface N-glycan map of released N-glycans following PNGase F enzyme treatment of whole intact cells from a composition of CD8+ T cells containing cells expressing an anti-CD19 chimeric antigen receptor (CAR). Specifically.

The method described above was carried out on an exemplary T cell composition generated by a process involving separately generating CD4+ and CD8+ populations of engineered T cells derived from the same subject following immunoaffinity-based enrichment of the CD4+ and CD8+ cell populations from a leukapheresis sample from a healthy human donor. Isolated CD4+ and CD8+ T cell populations were activated and transduced with a viral vector encoding an anti-CD19 CAR, followed by expansion and cryopreservation of the engineered cell populations. The anti-CD19 CAR contained an anti-CD19 scFv derived from a murine antibody, an Ig-derived spacer, a human CD28-derived transmembrane domain, a human 4-1BB-derived intracellular signaling domain and a human CD3 zeta-derived signaling domain. An annotated HILIC-FLR chromatogram of cell surface N-glycans from the engineered CD8+ T cell composition is depicted in FIG. 2A, and demonstrated a complex mixture of N-glycan types, including the presence of high mannose N-glycans, bisected glycans, and sialyl Lewis' glycans, were present on the surface of cells in the composition.

Figure 3A:
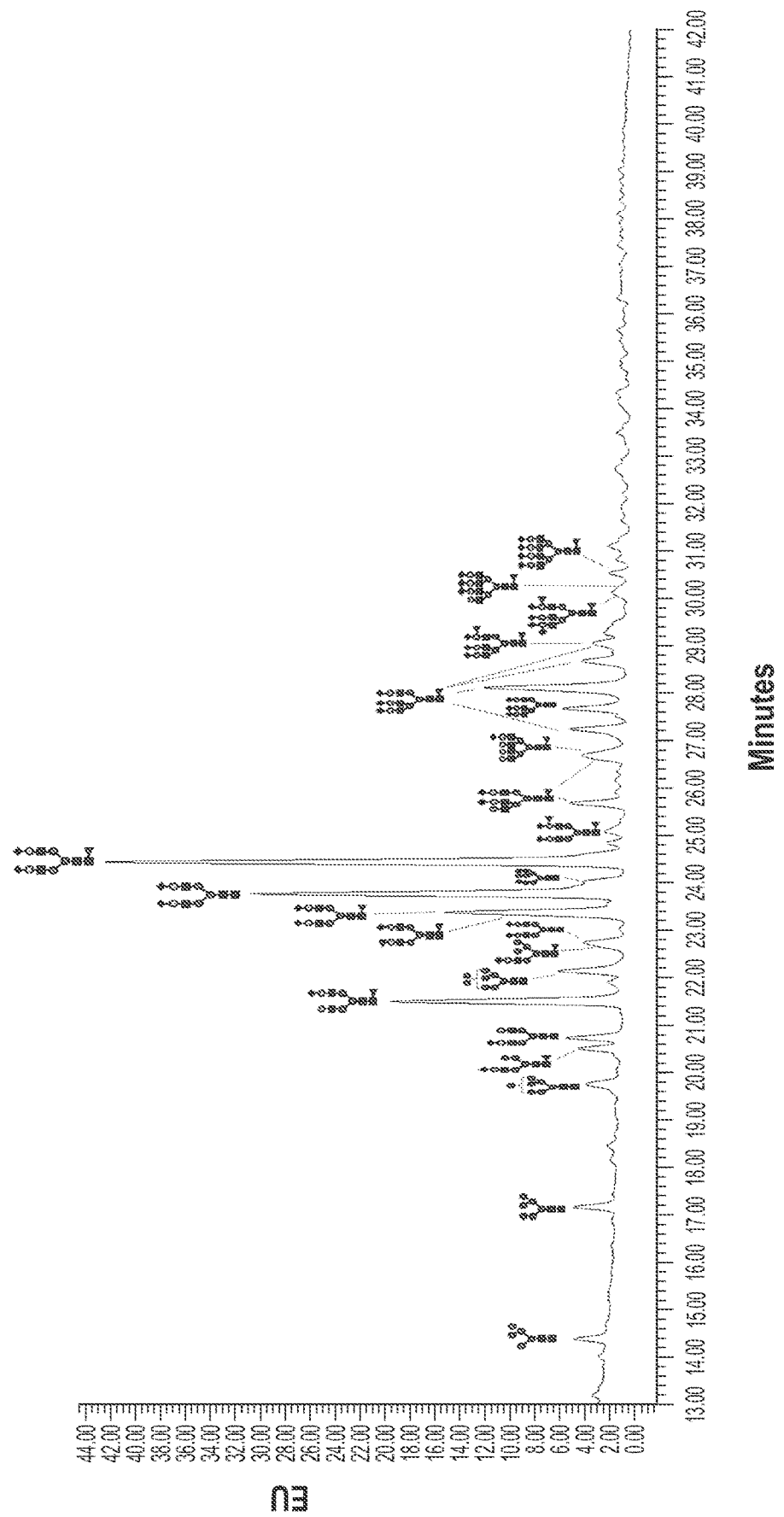
FIGS. 3A and 3B show exemplary readouts of surface N-glycan profiles.
Figure 3B:
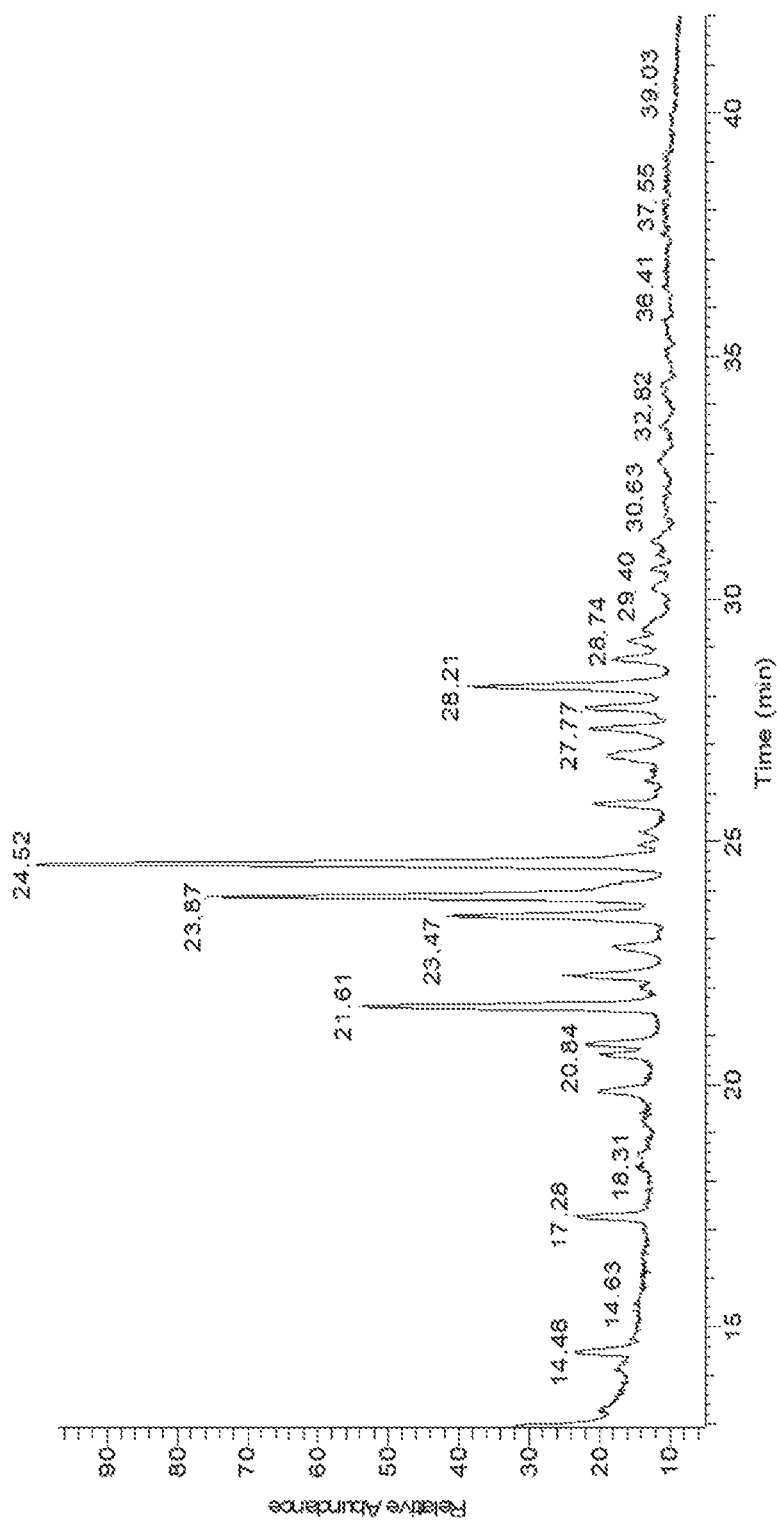

In another example, the method was carried out on an alternative exemplary anti-CD19 CART cell composition generated by a process involving immunoaffinity-based selection of T cells (including CD4+ and CD8+ cells) from a leukapheresis sample, followed by activation and transduction with a viral vector encoding the anti-CD19 CAR, expansion and cryopreservation. The CAR contained an anti-CD19 scFv derived from a murine antibody, a region of CD28 including an extracellular region, a transmembrane domain and a costimulatory region, and a CD3-zeta intracellular signaling domain. The annotated HILIC-FLR chromatogram in FIG. 3A and total ion chromatogram (TIC) in FIG. 3B, produced by the HILIC-ESI-MS analysis of the composition, similarly demonstrated an N-glycan profile containing a complex mixture of N-glycan types.

These results confirmed that it was possible to obtain high resolution maps of N-glycans released from the surface of whole, intact cells, thereby demonstrating that the method can be used to generate an N-glycan map of cell compositions to characterize the whole cell surface glycosylation state.

Example 2: Identification of Glycan Species by HILIC and Tandem Positive Electrospray Ionization Mass Spectrometry (ESI-MS/MS)

To confirm identification of glycans, high resolution mass spectrometry was employed to identify glycans, including isobaric species resolved by HILIC. The analysis was carried out on an exemplary composition containing activated CD3+ T cells that were activated following stimulation with anti-CD3/anti-CD28, e.g., coated on magnetic beads. N-glycans were extracted, labeled, and processed as described in Example 1. HILIC-ESI-MS was performed substantially as described in Example 1, except using tandem mass spectrometry (MS/MS). N-Glycans were separated by HILIC and detected by fluorescence (HILIC-FLR) and ESI-MS/MS provided relative quantification and identification.

Figure 4A:
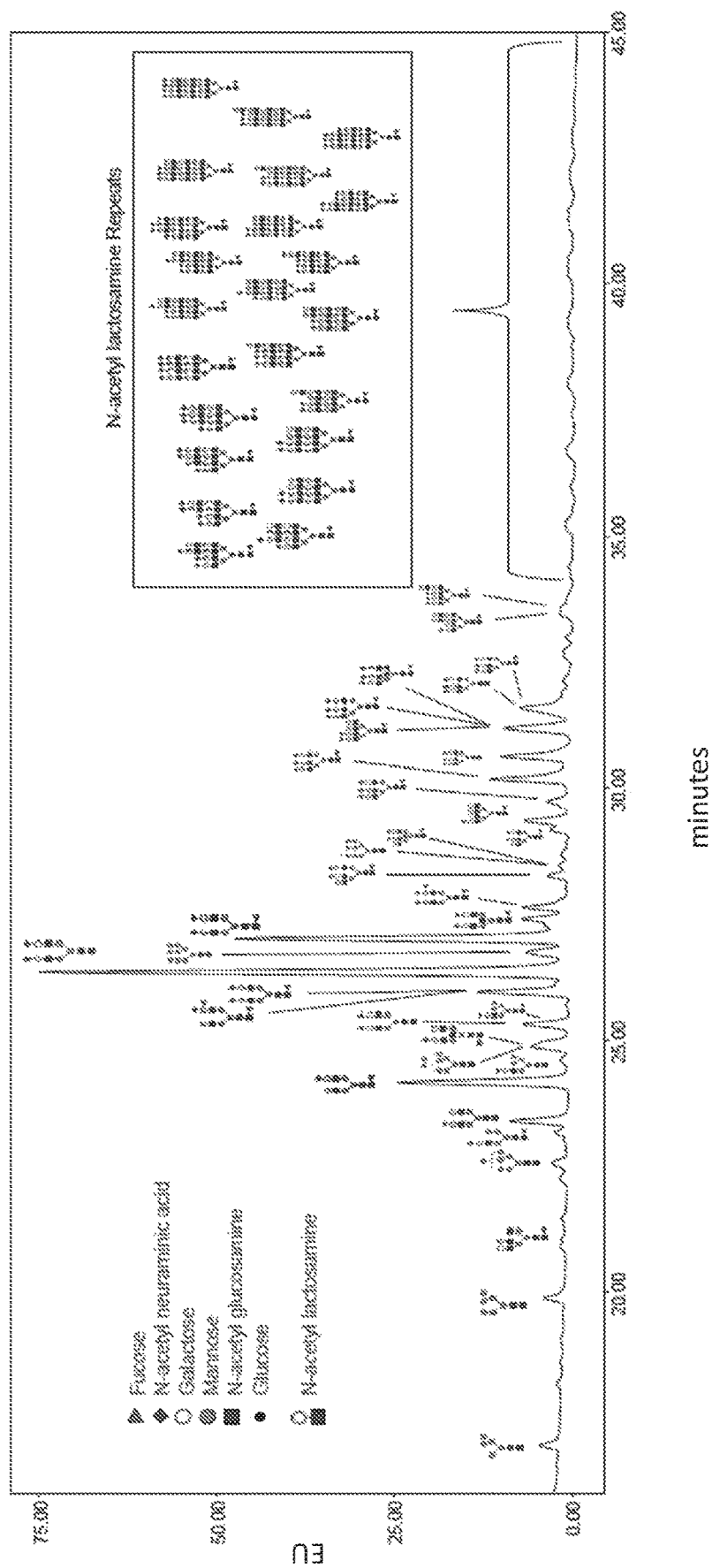
FIGS. 4A-C show chromatograms produced by HILIC-LC and tandem MS of N-glycans releases from whole intact CD3+ activated T cells following PNGase F treatment.

As shown in FIG. 4A, the annotated HILIC-FLR chromatogram revealed that the cell surface N-glycan map of anti-CD3/anti-CD28 activated CD3+ cells was a complex mixture of glycan types.

Figure 4B:
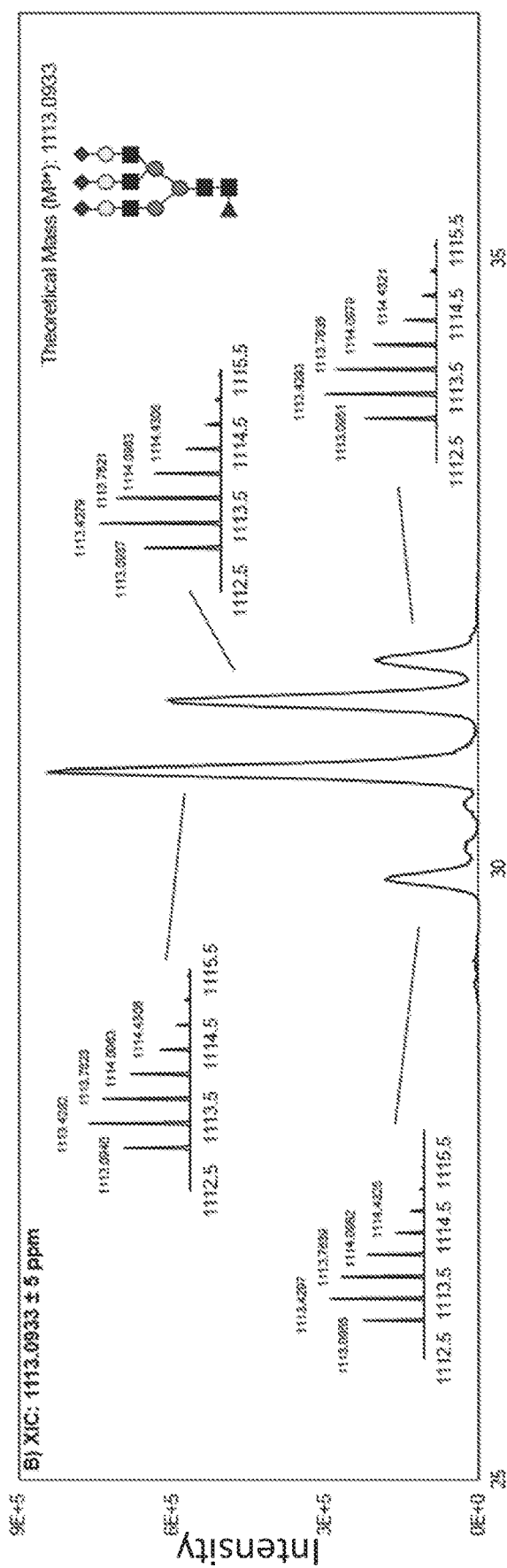
Figure 4C:
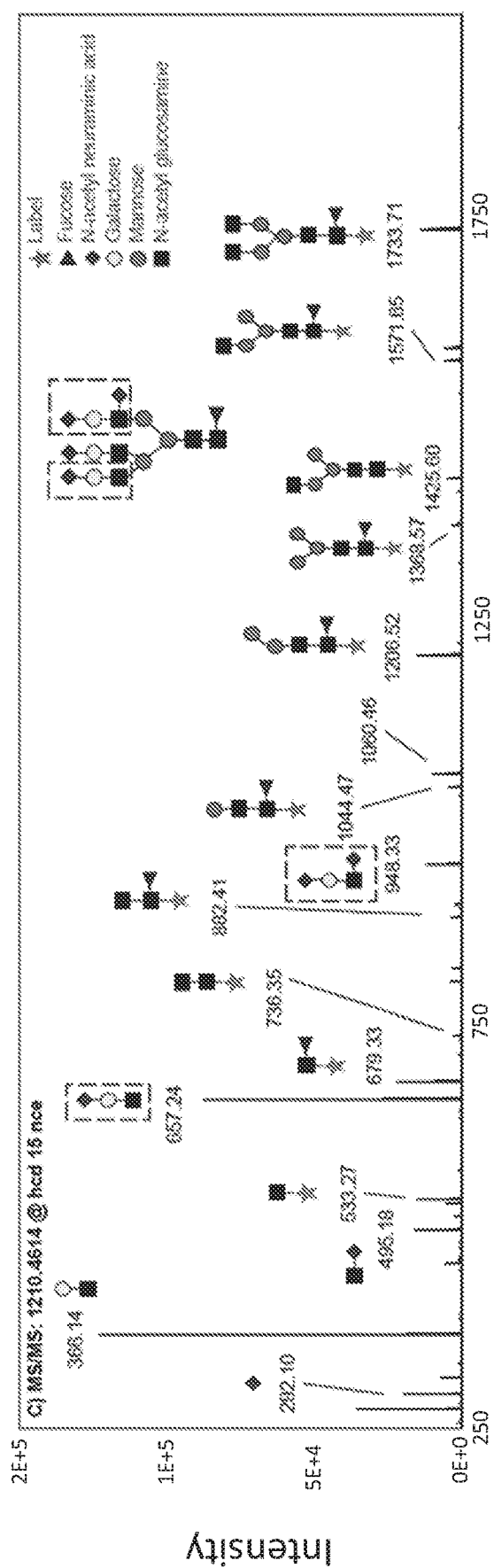

For tandem mass spectrometry (MS/MS), particles were ionized by ESI and separated by their mass-to-charge ratio at the first stage of the mass spectrometry. FIG. 4B depicts an extracted ion chromatogram (XIC) produced from the first stage of mass spectrometry for the exemplary A3S3F N-glycan in the +3 charged state using a 5 ppm mass tolerance. Multiple chromatographic peaks of the N-glycan with identical isotopic distributions were observed, which is consistent with the likely presence of linkage differences between the monosaccharide units of the glycan structure. After the first stage, the glycans underwent fragmentation and the resulting fragments were separated and measured in the second stage of the MS/MS. The MS/MS fragmentation of the exemplary N-glycan A3S4F, fragmented by high energy collisional dissociation (HCD) at a normalized collision energy (NCE) of 15, is shown in FIG. 4C. Combined with the high resolution MS data of the first stage, the fragmentation of A3S4F confirmed the presence of an n-acteyl neuraminic acid linkage at the canonical terminal galactose residue, as well as at a unique site on an n-acetyl glucosamine residue of the same antennae (FIG. 4C, boxes). These results demonstrate that MS/MS combined with the high resolution MS data can identify glycan structures, including unique glycan structures, following separation and detection by HILIC-FLR.

Example 3: Comparison of N-Linked Glycan Profiles of Different Cell Compositions The N-glycan mapping profile of whole, intact cells described in Example 1 was used to compare the N-glycan profile among different cell compositions.

A. Impact of Process Features for Engineering CD4+ and CD8+ CAR+ T cell compositions on N-Glycan Profiles Cell compositions obtained during various steps of an exemplary process of producing T cells engineered with a chimeric antigen receptor (CAR) were compared to investigate the impact of the process on T cell surface N-glycans in the cell product. The exemplary process generally involved isolation of bulk PBMCs followed by immunoaffinity-based selection resulting in selected CD4+ T cells and selected CD8+ T cells, which were then cryopreserved. The thawed, selected CD4+ and/or CD8+ T cells were separately incubated with a bead-based activation reagent and transduced with a lentiviral vector encoding the CAR. The transduced cells were incubated and expanded in the presence of cytokines and subsequently cryopreserved. Specifically, the following compositions were analyzed: (1) cell composition containing bulk PBMCs, (2) thawed cryopreserved cell compositions containing selected CD4+ or CD8+ T cells selected by immunoaffinity-based selection; (3) cell compositions containing selected T cells incubated with anti-CD3/anti-CD28 beads in the presence of IL-2, IL-15 and/or IL-7 for 18-24 hours at 37° C.; (4) cell compositions that were transduced with a lentiviral vector encoding the CAR; and (5) thawed, cryopreserved cell compositions containing CAR-expressing cells that were subjected to expansion in the presence of IL-2, IL-15 and/or IL-17 cytokines prior to cryopreservation. The N-glycan profile of whole, intact cells from the each of the above cell compositions was assessed using the procedures substantially as described in Example 1.

Bulk PBMCs exhibited a highly heterogeneous population of N-glycans including bi-, tri- and tetra-antennary hybrid and complex type sugars. Selection of T cells (CD4+ and CD8+) reduced the heterogeneity of the glycan pattern, resulting in primarily bi- and tri-antennary sialyated glycans with an increase in tetra-antennary species compared to the bulk cell population. CD4+ cells and CD8+ cells activated by anti-CD3/anti-CD28 co-stimulation, retained the bi- and tri-antennary species, while tetra-antennary species were reduced.

Figure 5A:
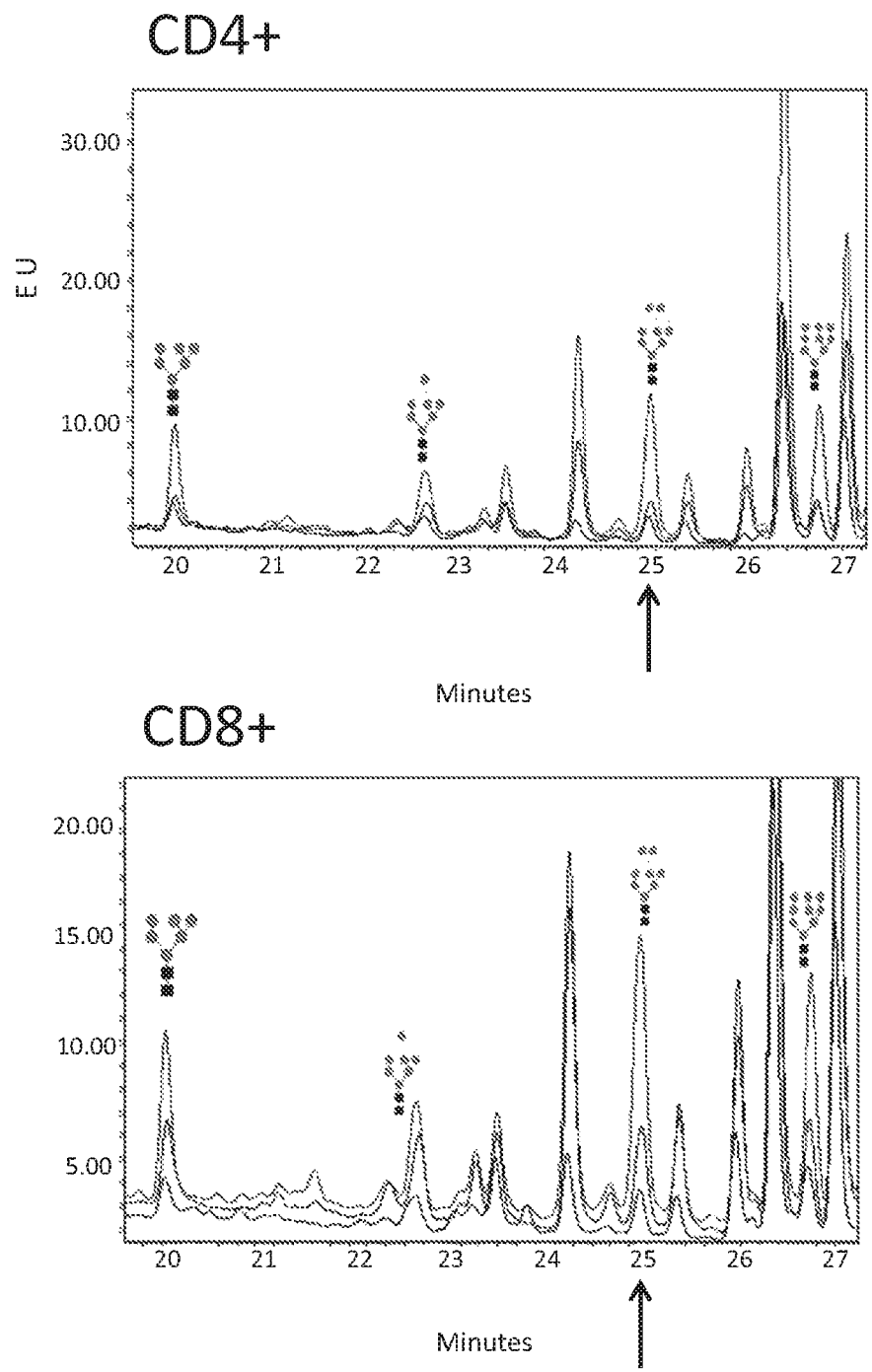
FIG. 5A-5C show overlays of peaks corresponding to surface N-glycans visualized by fluorescence detection and mass spectrometry from samples taken from cell compositions collected at different stages of production of a therapeutic cell composition containing cells expressing an anti- CD19 CAR. Surface N glycan maps of CD4+ and CD8+ T cell compositions of cells obtained from immunoaffinity-based selection of cells from leukapheresis samples, cells that were activated and transduced with a viral vector encoding an anti-CD19 CAR, and cells that were transduced, expanded, and harvested as a cryopreserved drug product are shown.
Figure 5B:
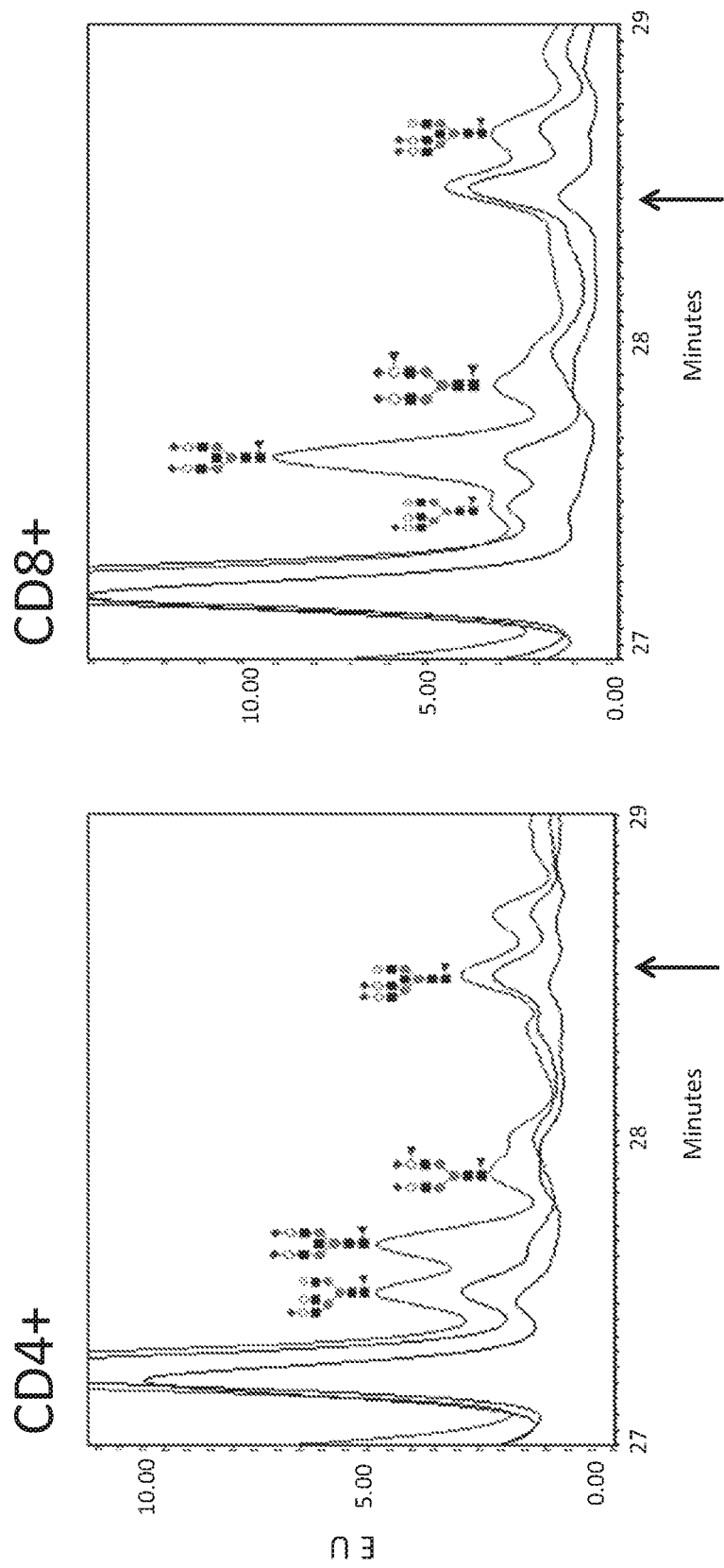
Figure 5C:
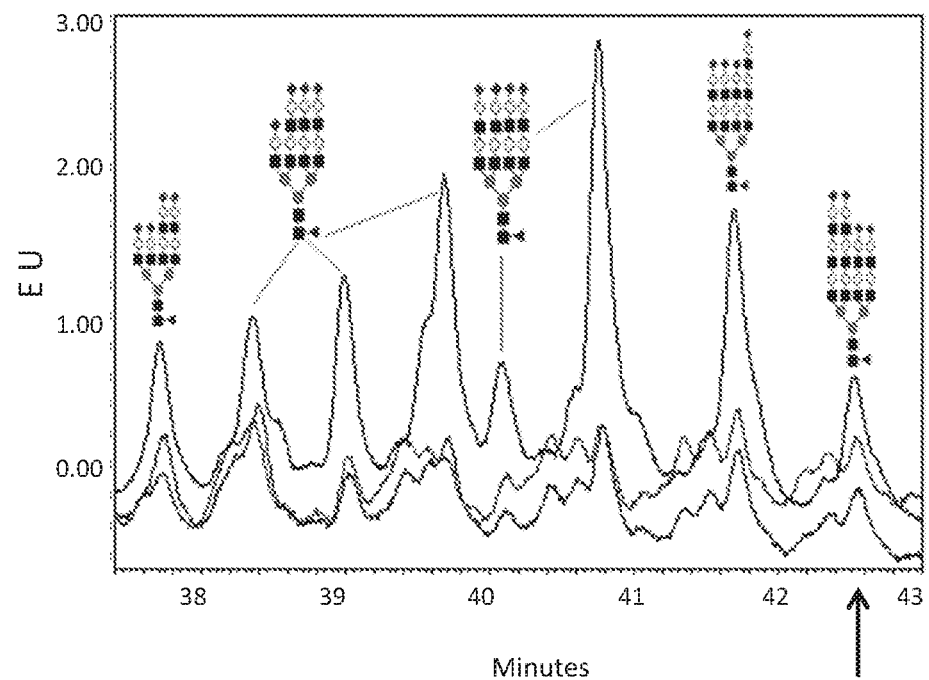
Figure 5C:
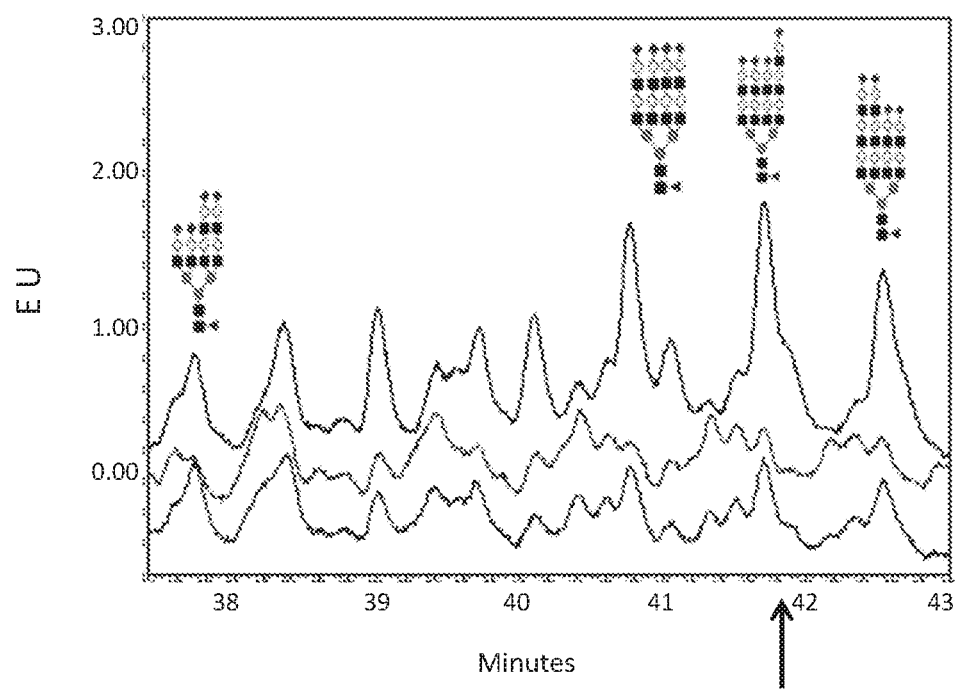

Comparison of the N-glycan profiles among T cell compositions containing selected CD4+ or CD8+ T cell compositions, CAR-transduced cells or CAR-transduced cells that were further expanded and cryopreserved, the same mixture of N-glycans, including high mannose N-glycans, bisected glycans, and sialyl Lewis$^X$ glycans, were present in each of the T cell compositions but at different levels. FIGS. 5A-5C provide overlays of cell surface N-glycan maps comparing levels of specific high mannose N-glycans (FIG. 5A), bisected and sialyl Lewis$^X$ N-glycans (FIG. 5B), and N-acetyl lactosamine containing N-glycans (FIG. 5C) in CD4+ and CD8+ cells among the cell compositions. These results are summarized in Table E2, which sets forth the percentage of N-glycans that were high mannose N-glycans, bisected and sialyl Lewis$^X$ N-glycans, and N-acetyl lactosamine containing N-glycans in each of the CD4+ and CD8+ compositions.

The results generally showed increased surface high mannose species glycans, increased Sialyl Lewis$^X$ N-glycans and decreased surface polylactosamine containing N-glycans in CD4+ and CD8+ cells from compositions containing CAR-expressing cells that were further expanded and cryopreserved compared to the selected CD4+ and CD8+ T cell compositions or CAR-transduced cell compositions. Without wishing to be bound by theory, it is hypothesized that in some cases these results may be due to changes in N-glycans occurring in the cell composition during expansion and/or activation. Within cell product compositions that were subjected to further expansion and cryopreservation, differences also were observed between CD4+ and CD8+ cell compositions, with CD8+ cell compositions exhibiting substantially more bisected N-glycans on their surface relative to the CD4+ cell compositions.

TABLE E2

Percentage of N-glycans in CD4+ and CD8+ cell compositions

| Cell Composition | % High Mannose | | % Bisected/Sialyl Lewis$^X$ | | % N-acetyl lactosamine containing | |
|---|---|---|---|---|---|---|
| | CD4 | CD8 | CD4 | CD8 | CD4 | CD8 |
| Selected T cells | 9.3 | 10.5 | 1.7 | 1.8 | 33.3 | 22.5 |
| Transduced T cells | 10 | 10.1 | 2.8 | 3.6 | 17 | 16.6 |
| Transduced and expanded T cells | 17.4 | 17.1 | 5.7 | 9.9 | 13 | 13.8 |

B. Impact of Process Features on N-Glycan Profile of T Cell Compositions

Cell compositions employed during engineering of CAR+ T cells were assessed for impact of process features, e.g. selection and activation, on N-glycan profiles. CD3+ T cells were selected from bulk PBMCs by immunoaffinity-based selection and cryopreserved. Following thaw, the selected CD3+ T cells were incubated with an anti-CD3/anti-CD28 bead-based activation. Specifically, the following compositions were analyzed: (1) cell composition containing peripheral blood mononuclear cells, (2) cell composition containing selected CD3+ T cells selected by immunoaffinity-based selection; and (3) cell composition containing selected T cells incubated with anti-CD3/anti-CD28 beads. The N-glycan profile of whole, intact cells from the each of the above cell compositions was assessed using the procedures substantially as described in Example 1.

Figure 6:
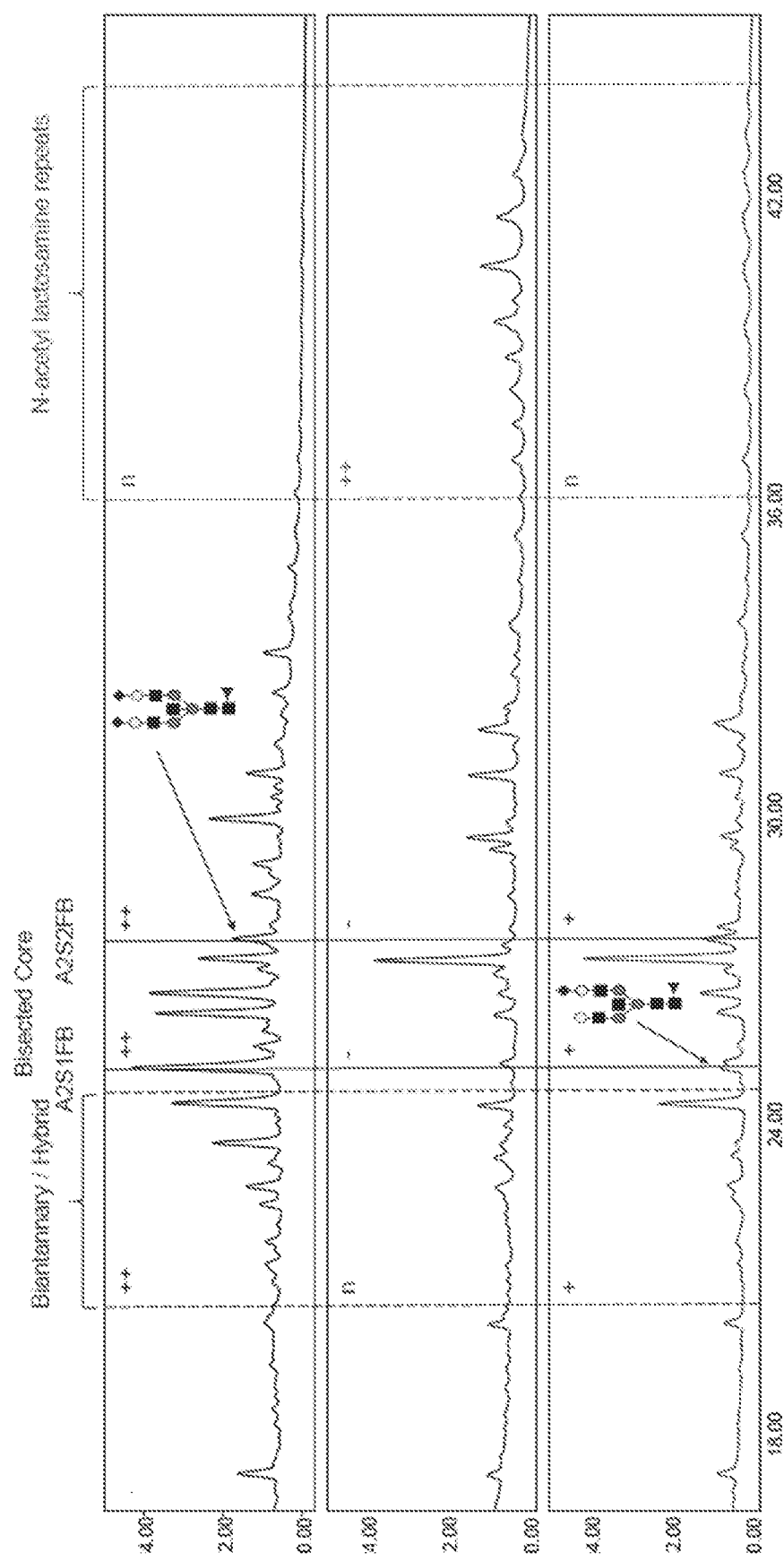
FIG. 6 shows a comparison of surface N-linked glycan profiles of cell compositions collected at different stages of production of a cell composition containing cells expressing an anti-CD19 CAR: mononuclear cells (top); CD3+ T cells (middle); and activated CD3+ T cells (bottom). Exemplary differences are highlighted with annotation for increased (++ or +), amount (n), or decreased (−) amount of glycan species. Peaks corresponding to the A2S1FB and A2S2FB N-glycans are indicated by a solid line. Regions of the chromatogram corresponding to biantannary/hybrid and N-acetyl lactosamine repeat N-glycans are indicated by dashed lines.

As shown in the exemplary HILIC-FLR chromatograms in FIG. 6, differences were observed in the relative levels of surface N-glycans, particularly for expressed biantennary/hybrid, bisected core, and N-acetyl lactosamine repeat N-glycans. Exemplary areas of changes are highlighted in FIG. 6 based on the degree of increase (+ or ++) or decrease (−) between one or more of the other compositions. These results are consistent with a conclusion that the steps for processing cells to generate engineered T cells can influence surface N-glycan profiles.

C. N-Glycan Profile of Different CAR-T Cell Compositions

The surface N-linked glycan profiles of CD4+ and CD8+ T cell compositions comprising T cells expressing an anti-CD19 CAR described above were compared to the N-glycan profile of a cell composition containing T cells expressing an alternative anti-CD19 CAR and a cell composition containing T cells expressing a CAR that recognizes an alternative target antigen. The alternative anti-CD19 CAR contained an anti-CD19 scFv derived from a murine antibody (which was different from the anti-CD19 scFv of the anti-CD19 CAR described above), a region of human CD28 including an extracellular region, a transmembrane domain and a costimulatory region, and a human CD3-zeta intracellular signaling domain. The CAR that recognizes an alternative target antigen comprised a human scFv, a spacer region, a CD28 transmembrane domain, a 4-1BB-derived intracellular co-signaling sequence, and a CD3-zeta derived intracellular signaling domain. The process to produce each of the cell compositions also differed with respect to various features, such as the presence, number or ratio of CD4+ and CD8+ cells, and/or the conditions for activation, transduction and/or expansion.

Figure 7:
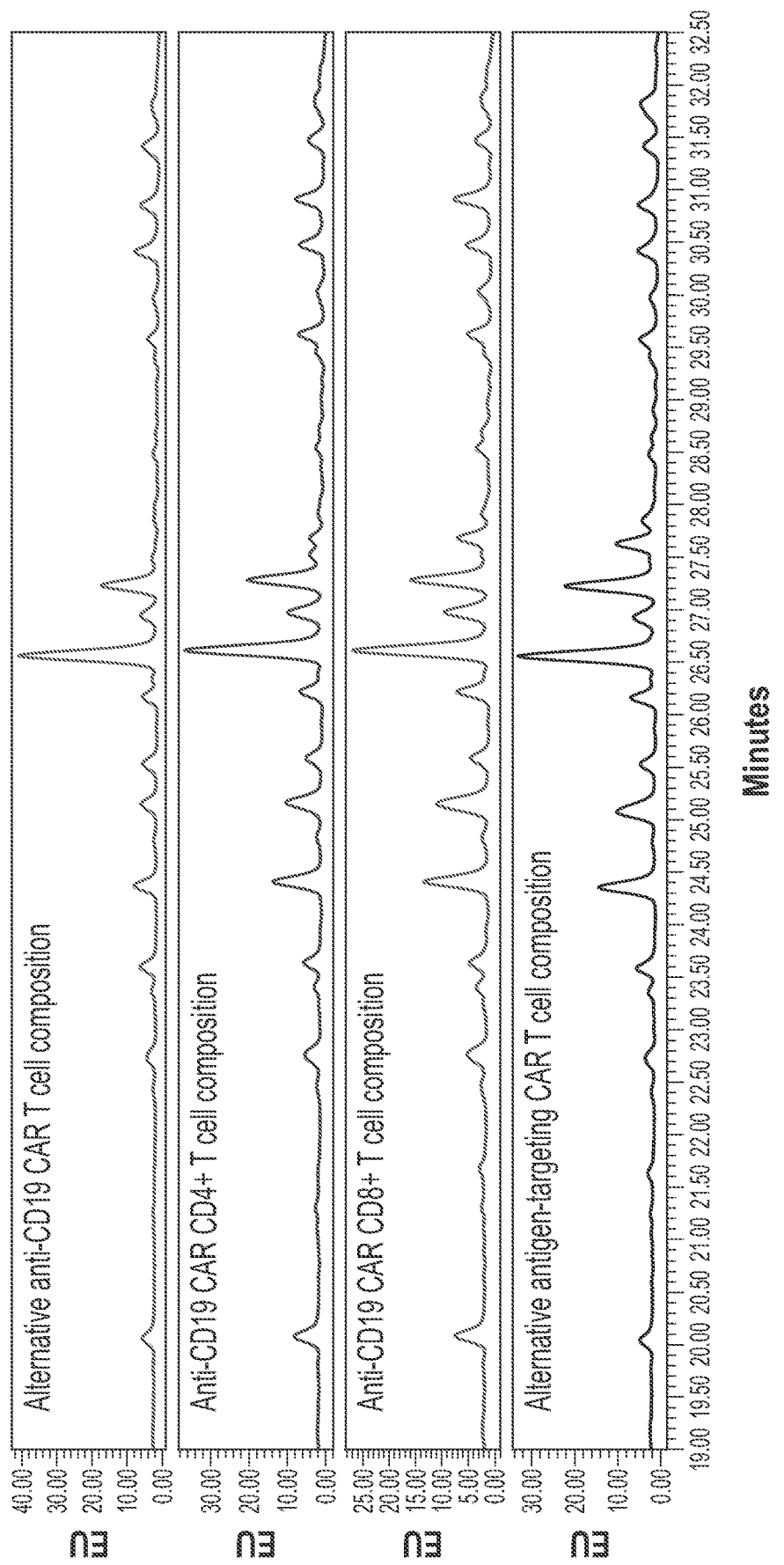
FIG. 7 shows surface N-glycan maps visualized by fluorescence detection and mass spectrometry of surface N-glycan samples from different CAR-expressing T cell compositions, including CD4+ and CD8+ T cell compositions expressing an anti-CD19 CAR, a T cell composition expressing an alternative anti-CD19 CAR or a T cell composition expressing an CAR that recognizes an alternative target antigen.

The N-glycan profile of whole, intact cells from the cell compositions were assessed using the procedures substantially as described in Example 1. As shown in FIG. 7, each of the analyzed compositions exhibited a unique cell surface N-glycan profile. The percentage of exemplary types of N-glycans in each cell composition are summarized in Table E2. In some cases, N-acetylactosamine exists as repeats present in a polylactosamine glycan.

In the composition containing the alternative anti-CD19 CAR, approximately 1% of cell surface N-glycans were bisected N-glycans. This result was consistent across more than twelve tested compositions comprising cells expressing the alternative anti-CD19 CAR produced using a similar process. The N-glycan profile from the cell composition containing cells expressing the CAR that recognizes an alternative target antigen demonstrated high levels of bisected N-linked glycans and Sialyl Lewis' N-glycans.

TABLE E3

Percentage of exemplary types of N-glycans

| | Alternative anti-CD19 CAR T cell composition | Anti-CD19 CAR CD4+ T cell composition | Anti-CD19 CAR CD8+ T cell composition | Alternative CAR T cell composition | Purpose/Role |
|---|---|---|---|---|---|
| N-acetyl lactosamine | 14.2 | 13 | 13.8 | 11.5 | Galectin* Binding |
| High Mannose | 11.9 | 17.4 | 17.1 | 14.3 | Immature/Incomplete Processing |
| Bisected | 0.9 | 2.8 | 6.9 | 11.3 | Reduces Galectin Binding |
| Sialyl Lewis | 3 | 2.9 | 3 | 6 | Selectin* Binding |

D. Analysis of N-Glycan Profiles of Engineered Cells Generated by Different Processes The surface N-linked glycan profiles of three different CD4+ T cell compositions comprising T cells expressing the exemplary anti-CD19 CAR described above in Example 3A were obtained by substantially the same methods as described in Example 1. Two of the CD4+ T cell compositions were obtained from a sample from the same individual subject, one of which was produced by a method similar to the exemplary engineering process described in Example 3A ("exemplary process") and the other CD4+ T cell composition was produced by an exemplary alternative engineering process ("alternative process"). A second CD4+ T cell composition from an additional subject sample was produced from the alternative method.

Figure 8:
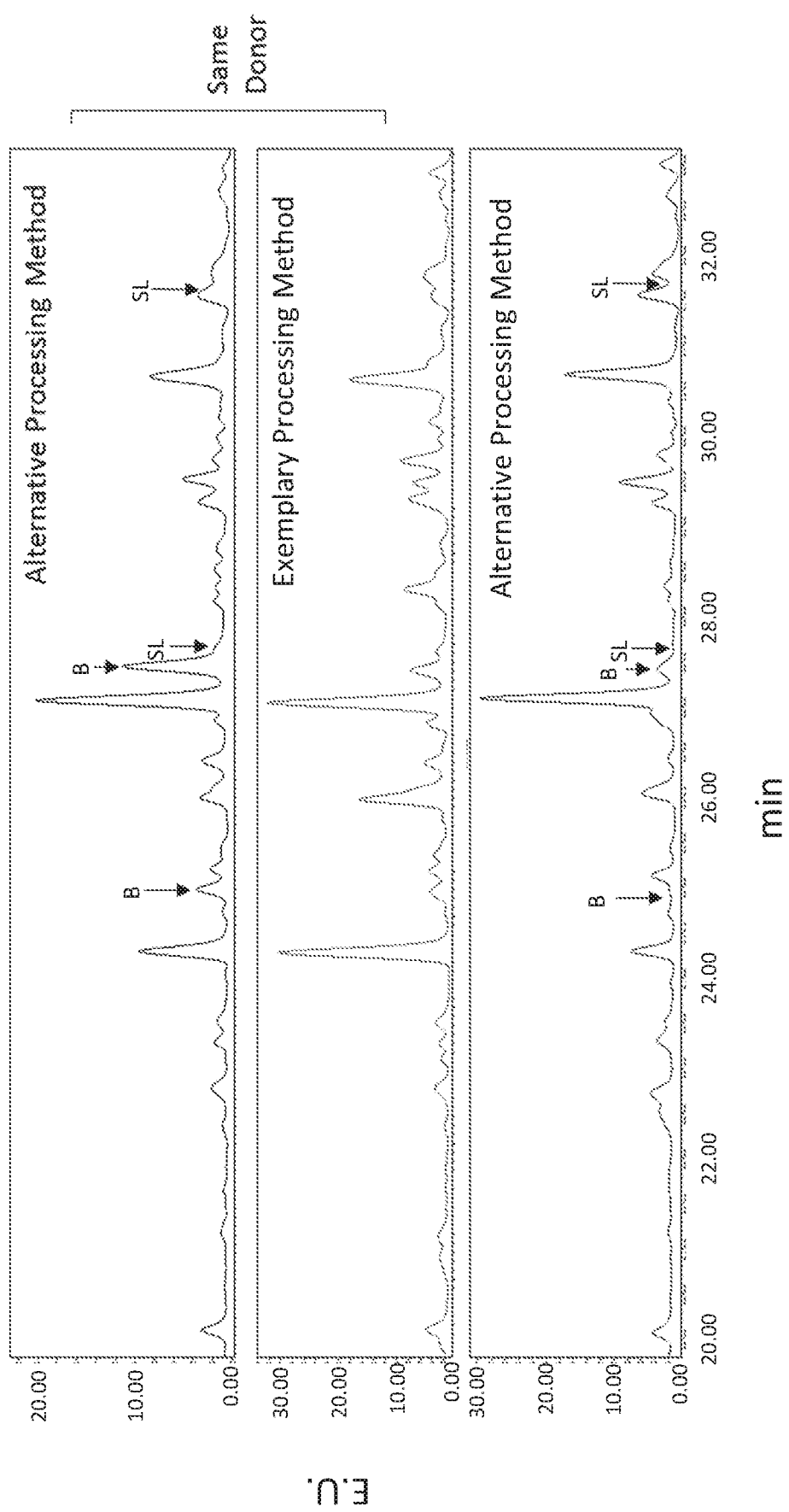
FIG. 8 shows surface N-glycan profiles visualized by fluorescence detection and mass spectrometry from CD4+ T cell compositions containing anti-CD19 CAR+ T cells produced by either an exemplary or alternative engineering process. Surface N-glycan profiles from an anti-CD19 CAR-expressing CD4+ T cell composition produced by the alternative engineering process (top panel), an anti-CD19 CAR-expressing CD4+ T cell composition engineered from cells from the same individual subject produced by the exemplary engineering process (middle panel), and an anti-CD19 CAR-expressing T cell composition engineered from cells of a different individual subject produced by the alternative engineering process (bottom panel). Arrows indicate peaks associated with specific N-glycans; "B" indicates a bisected N-glycan and "SL" indicates a Sialyl Lewis$^x$ N-glycan.

The N-glycan profile of whole, intact cells from the cell compositions were assessed using the procedures essentially as described in Example 1. As shown in FIG. 8, differences were observed among individual peaks of the surface N-glycan profiles. The observed bisected and Sialyl-Lewis$^x$ N-glycan content obtained from the CD4+ T cell compositions are summarized in Table E4.

TABLE E4

N-glycan content in CD4+ T cell compositions containing anti-CD19 CAR expressing cells

| Subject | Engineering Process | % Bisected N-glycans | % Sialyl-Lewis N-glycans |
|---|---|---|---|
| 1 | Alternative | 9.8 | 3.4 |
| 1 | Exemplary | 1.9 | 2.0 |
| 2 | Alternative | 1.6 | 1.6 |

Figure 9:
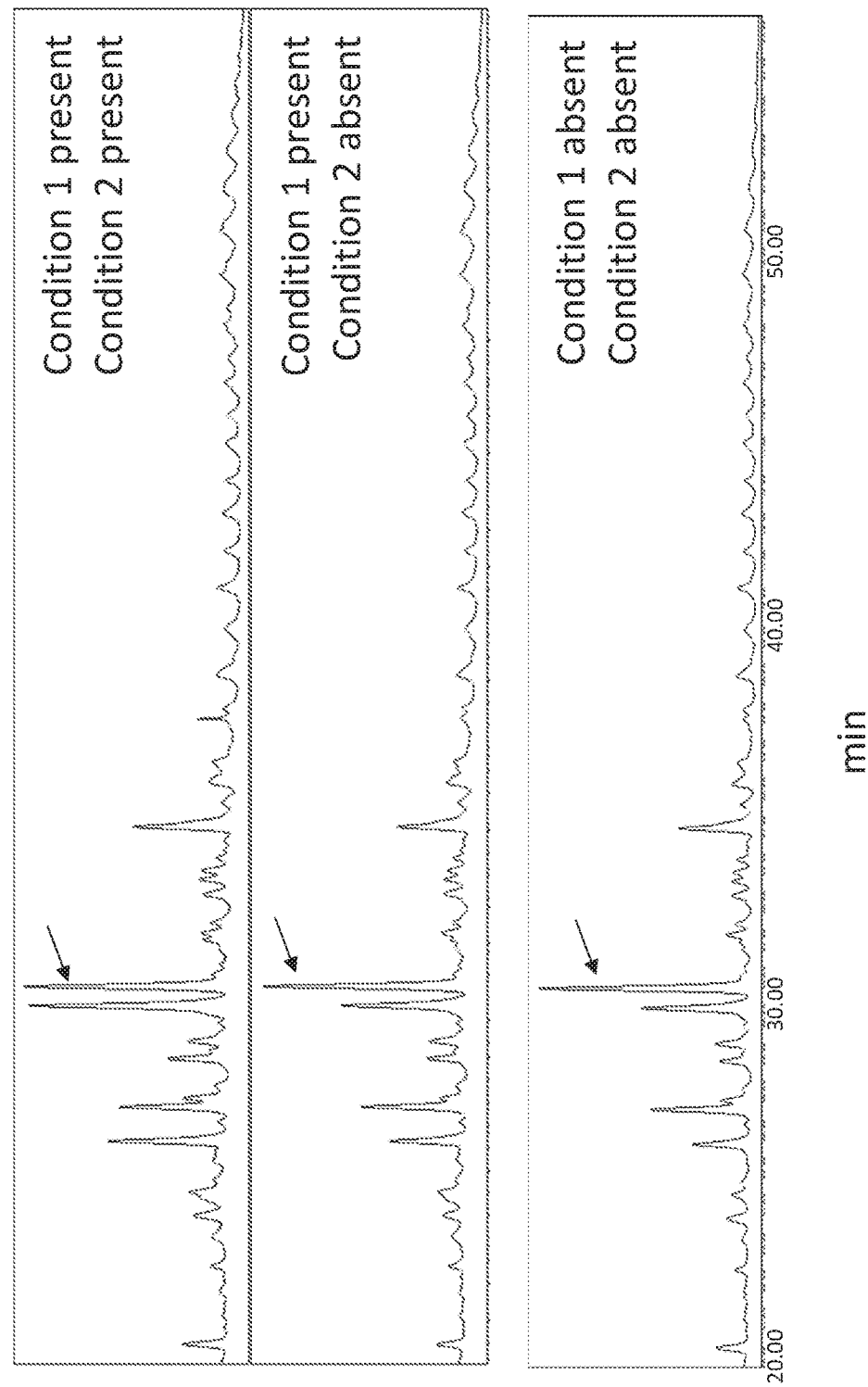
FIG. 9 FIG. 10 shows surface N-glycan profiles visualized by fluorescence detection and mass spectrometry from three exemplary different anti-CD19 CAR-expressing CD8+ T cell compositions that were generated by substantially the same process, but that differed in two conditions involved in cultivating the cells. Arrows indicate a peak associated with a bisected N-glycan.
Figure 10:
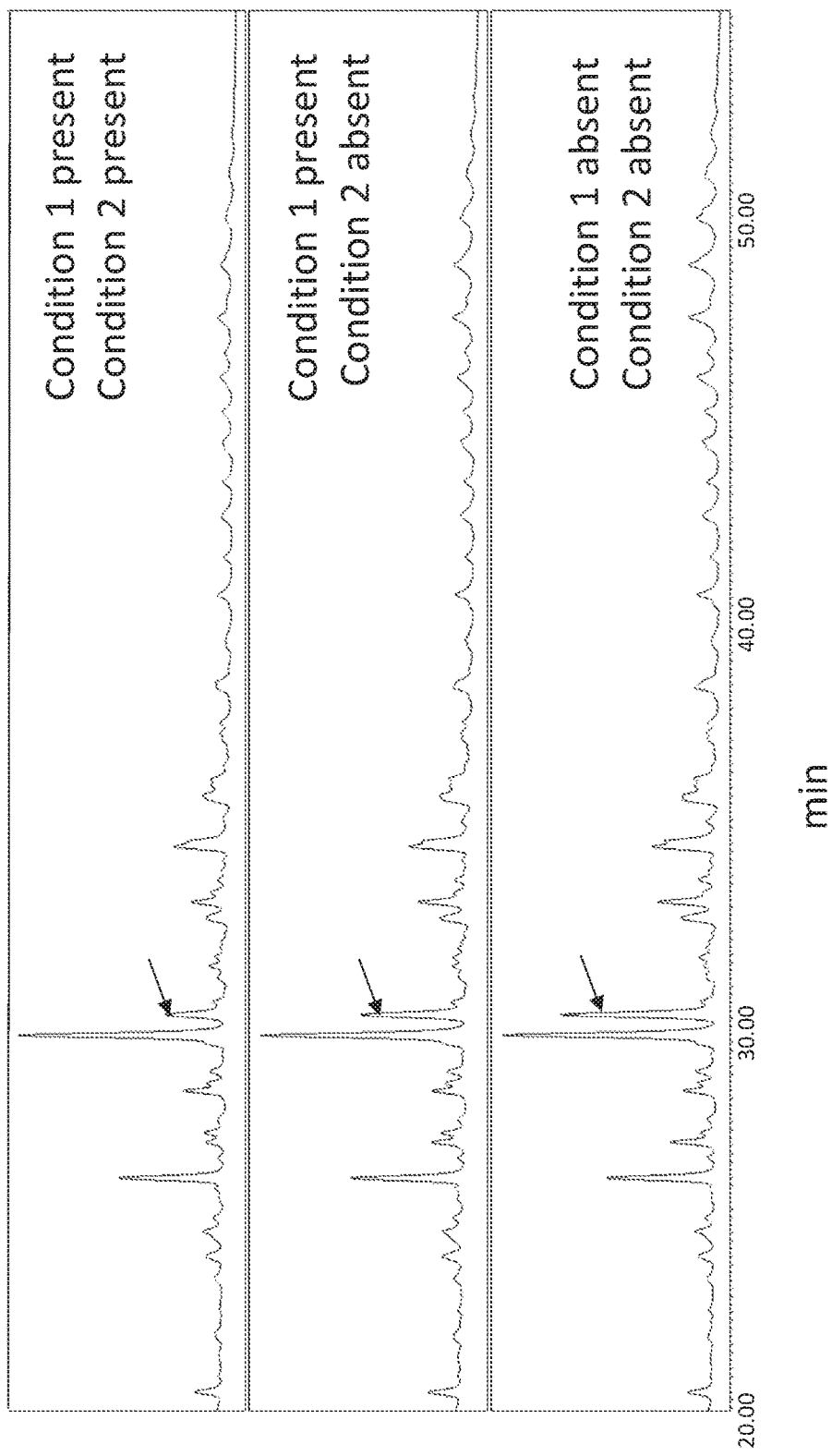

To further assess if different variables used during a cell engineering process may result in different surface N-glycan profiles, three CD4+ and three CD8+ T cell compositions containing T cells expressing the exemplary anti-CD19 CAR were generated from samples obtained from the same individual subject. The T cell compositions were essentially generated by the substantially the same engineering process, with the exception that they differed in aspects related to two conditions used in the process for engineering and cultivating the cells. As shown in FIGS. 9 and 10, the surface N-glycan profiles observed in the CD4+(FIG. 9) and the CD8+(FIG. 10) T cell compositions appeared consistent, although changes in specific peaks corresponding to bisected glycans (arrows) were observed.

E. N-Glycan Surface Profiles of T Cell Compositions Containing CAR Expressing Cells The surface N-linked glycan profiles of T cell compositions comprising T cells expressing either the exemplary anti-CD19 CAR described above in Example 3A or a CAR with an alternative target antigen were obtained by the method described in Example 1. Two compositions were generated from samples obtained from the healthy subjects, and one was obtained from a subject having a disease associated with the target antigen (patient).

Figure 11:
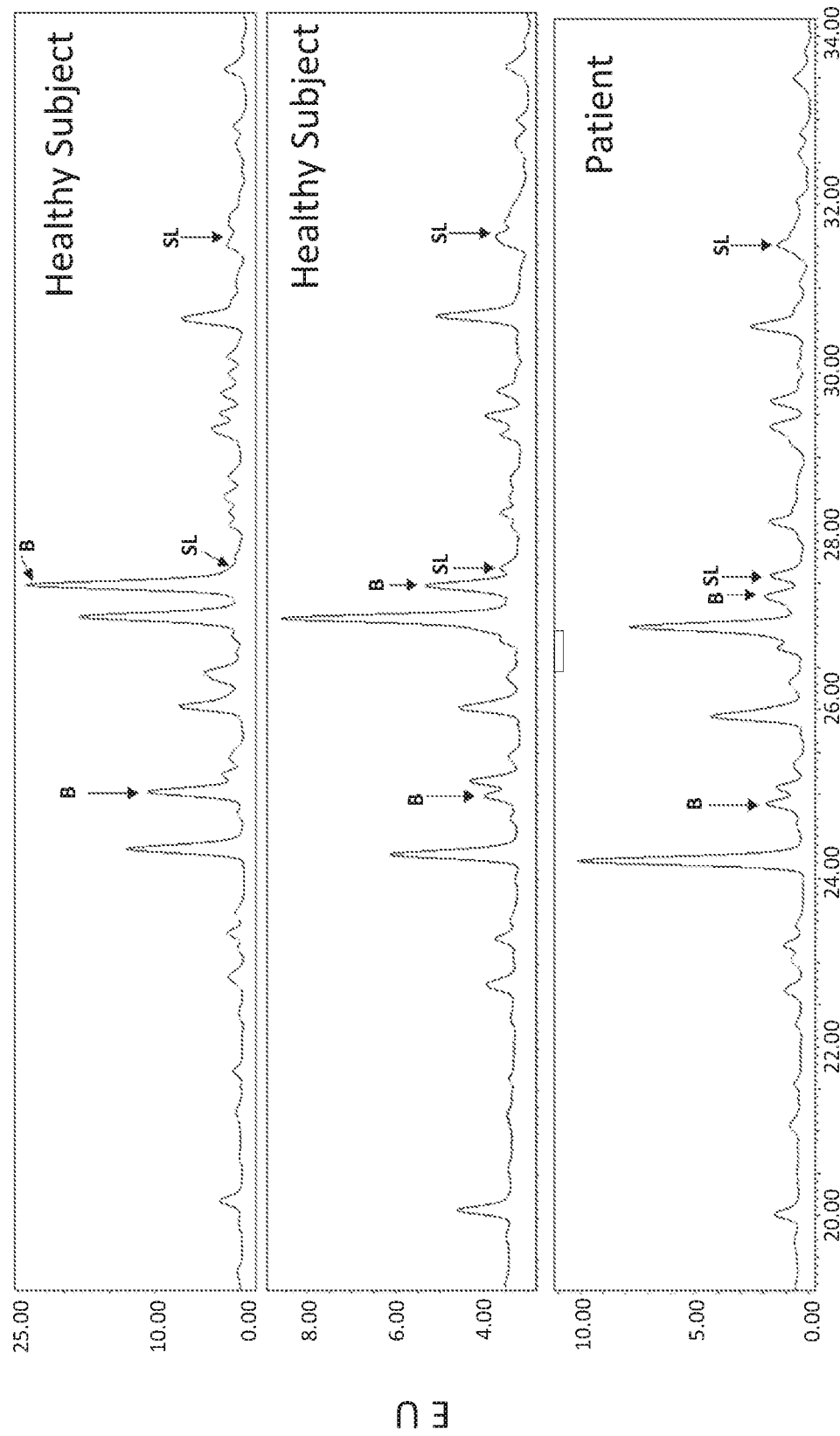
FIG. 11 shows surface N-glycan profiles visualized by fluorescence detection and mass spectrometry of surface N-glycan samples from different anti-CD19 CAR-expressing CD8+ T cell compositions. Surface N-glycan profiles from anti-CD19 CAR-expressing CD8+ T cell compositions produced from cells from healthy subjects (top and middle panels) and from a subject with disease associated with CD10 (bottom panel) are shown. Arrows indicate peaks associated with specific N-glycans; "B" indicates a bisected N-glycan and "SL" indicates a Sialyl Lewis$^x$ N-glycan.
Figure 12:
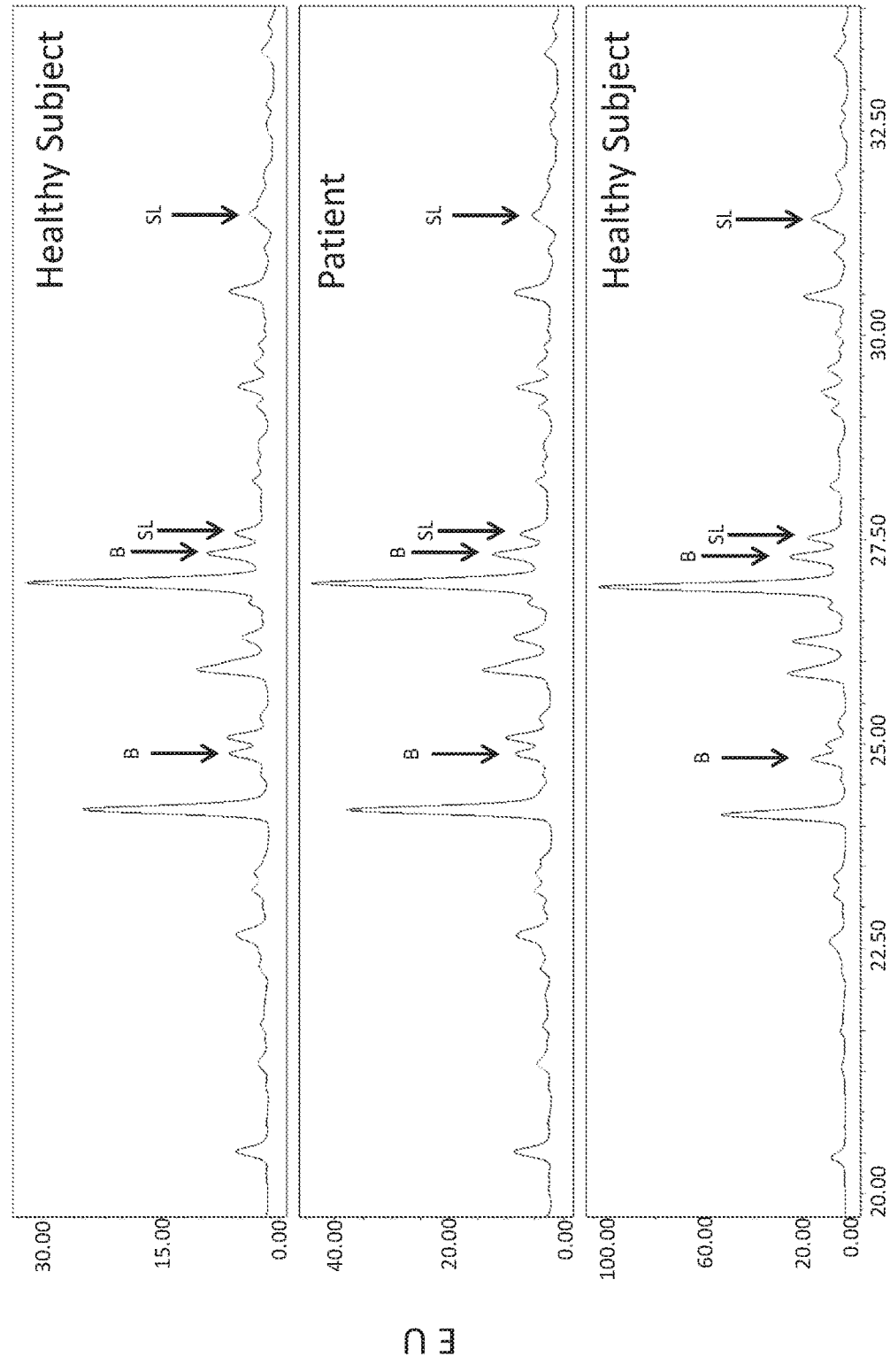
FIG. 12 shows surface N-glycan profiles visualized by fluorescence detection and mass spectrometry from different T cell compositions containing T cells that express a CAR with an alternative target antigen. Surface N-glycan profiles from CAR-expressing T cell compositions produced from cells from healthy subjects (top and bottom panels) and from a subject with a disease associated with the target antigen (middle panel) are shown. Arrows indicate peaks associated with specific N-glycans; "B" indicates a bisected N-glycan and "SL" indicates a Sialyl Lewis' N-glycan.

The N-glycan profiles of whole, intact cells from the cell compositions were assessed using the procedures essentially as described in Example 1. As shown in FIGS. 11 and 12, differences were observed among individual peaks of the surface N-glycan profiles (see arrows) obtained from the anti-CD19 CAR CD8+ T cell compositions (FIG. 11) and the alternative CAR T cell compositions (FIG. 12). Differences between bisected and Sialyl-Lewis$^x$ N-glycan content were also observed and are summarized in Table E5 and E6.

TABLE E5

N-glycan content in CD8+ T cell compositions containing anti-CD19 CAR expressing cells

| Subject | Status | % Bisected N-glycans | % Sialyl-Lewis N-glycans |
|---|---|---|---|
| 1 | Healthy | 19.0 | 0.9 |
| 2 | Healthy | 8.4 | 4.9 |
| 3 | Patient | 6.5 | 6.7 |

TABLE E6

N-glycan content in T cell compositions containing cells expressing a CAR that targets an alternative antigen

| Subject | Status | % Bisected N-glycans | % Sialyl-Lewis N-glycans |
|---|---|---|---|
| 1 | Healthy | 6.4 | 6.3 |
| 2 | Patient | 8.6 | 6.5 |
| 3 | Healthy | 7.7 | 7.5 |

The results show that different degrees of variability of surface N glycan profiles may exist among different CAR T cell compositions generated from different donors. This observation is consistent with a utility of surface N-glycan profiling to monitor changes in glycosylation during a process for generating cells and to utilize N-glycan profiles as a parameter to monitor uniformity of cell compositions generated from different donors and/or using the same or different processes.

Example 4: Detection of Substances with Surface N-Glycan Profiling

The ability of surface N-glycan profiling to detect glycans originating from various substances (for example, potential residual substances, such as residual proteins present in cell compositions) was tested. Such substances may include serum proteins, cytokines or growth factors used in a process for engineering cells, including cells expressing recombinant receptors, e.g. CAR.

Figure 13:
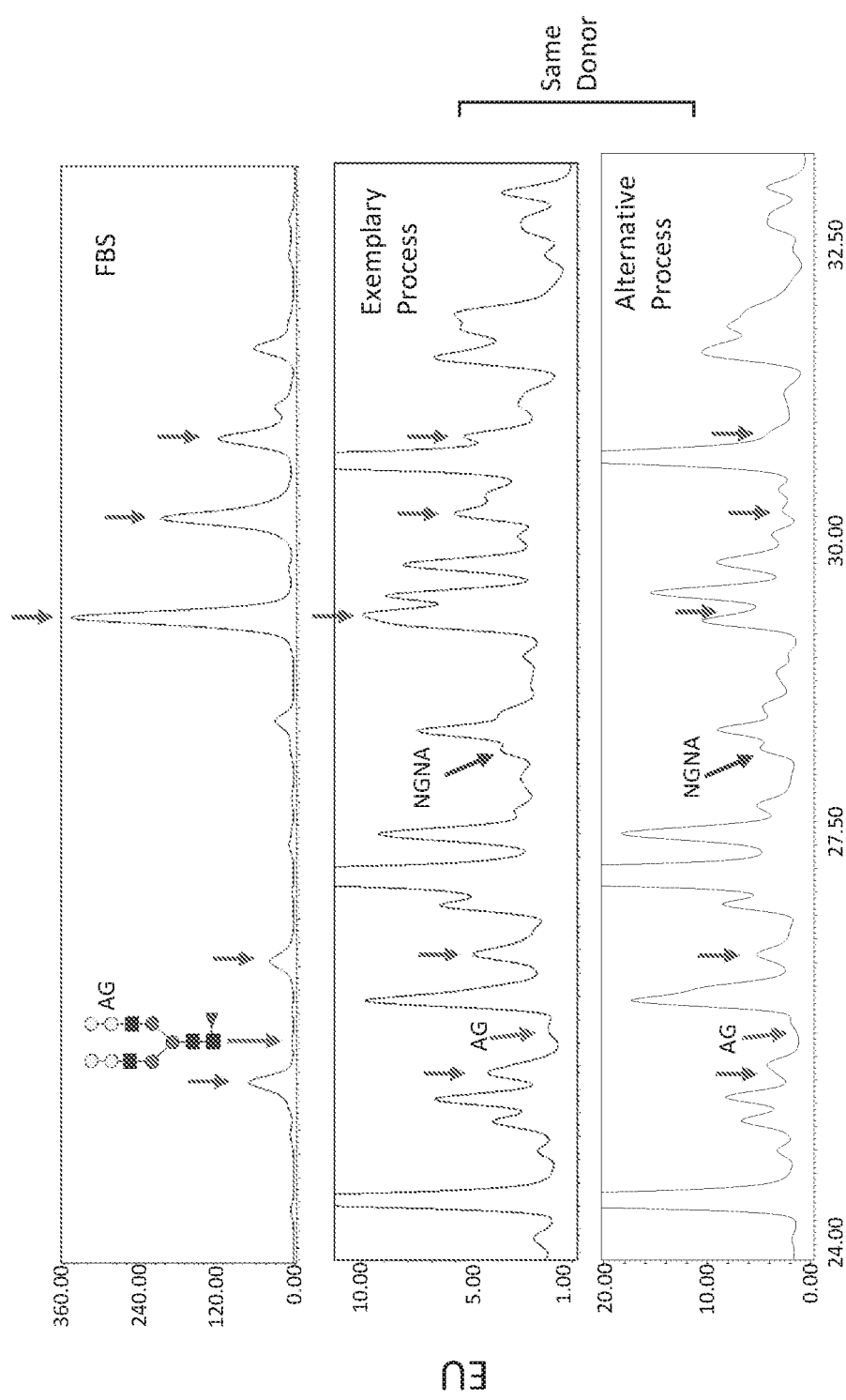
FIG. 13 shows surface N-glycan profiles visualized by fluorescence detection and mass spectrometry from a sample of fetal bovine serum (FBS; top panel) and surface N-glycan profiles from a CD4+ anti-CD19 CAR-expressing CD4+ T cell composition engineered from cells from the same individual subject produced by the two different engineering processes (middle and bottom panels). Arrows indicate peaks associated with FBS N-glycans; "AG" indicates a peak associated with a non-human alpha-gal N-glycan and "NGNA" indicates a peak associated with a non-human N-glycolylneuraminic acid (NGNA)N-glycan.

As an example of a substance, a sample of fetal bovine serum (FBS) was incubated with PNGase F PRIME. N-glycans were collected from the sample and dried down. The N-glycans were then reconstituted in water and labeled, cleaned by SPE, and analyzed with HILIC-ESI-MS similar to as described in Example 1. As shown in FIG. 13 (top panel) a glycan profile was generated, consistent with an ability of glycan profile mapping to detect N-glycans bound to FBS.

N-glycan profiles were generated from CD4+ and CD8+ T cell compositions containing T cells expressing the exemplary anti-CD19 CAR described in Example 3A. For each sample from an individual subject, two CART cell compositions were generated by different processes that differed in the conditions used for activating and cultivating the cells. Both processes involved incubations with media containing FBS. Surface N-glycan profiles were generated as described in Example 1.

Exemplary surface N-glycan profiles from CD4+ CAR T cell compositions produced by the different processes are shown in FIG. 13. Glycans originating from FBS were detected in all of the examined CAR T cell compositions (arrows). The detected N-glycans originating from FBS included an alpha-gal (AG) and an NGNA epitope. These epitopes are not present in primates, consistent with a non-human source, e.g., FBS. The alpha-gal epitope made up less than 1% of the total N-glycan profiles measured from both cell compositions. In this experiment, the FBS N-glycans were observed in profiles from the CAR T cell compositions in the same proportions as observed from the FBS sample, consistent with FBS as the source of the glycans. Differences in residual FBS N-glycans detected in N-glycan profiles were observed in CAR T cell compositions generated by the different processes. No non-human glycans were observed in a cell composition that was generated by a process that employed serum-free media.

Example 5: Effects of Surface N-Glycan Levels on T Cell Activity

Mixed CD4+ and CD8+ T cell compositions containing cells expressing a CAR were generated from a healthy individual subject and cryofrozen. The CAR T cell compositions were thawed, rinsed, and then were treated for 30 minutes with PNGase F (PNGase F Prime) to remove surface glycans from the cells or Sialidase A 51 to remove terminal sialic acid residues from the cells. As a negative control, cells were incubated DPBS alone.

Cells from the CART cell compositions were rinsed, and $2.5 \times 10^4$ CAR+ T cells per well were incubated with anti-CD3/anti-CD28 antibody conjugated beads (bead stimulation) or co-cultured with cells that endogenously expressed the target antigen of the CAR (antigen stimulation). After 14-18 hours, media was collected from the cell cultures and the extracellular IFN-gamma was quantified with a IFN-gamma AlphaLISA kit.

As shown in Table E7, removal of N-glycans or terminal sialic acid residues from the cell surface of the CAR T cells resulted in an increased production of IFN-gamma following stimulation by the anti-CD3/anti-CD28 antibody conjugated beads as compared to the control treated cells. Removal of surface N-glycans also increased extracellular levels of IFN-gamma following the co-culture with target antigen expressing cells. These data are consistent with a role of surface N-glycans in impacting T-cell activity.

TABLE E7

Extracellular IFN-gamma levels following stimulation of CAR T cell compositions

| | Bead Stimulation | | Antigen stimulation | |
|---|---|---|---|---|
| | Final [IFNγ] (pg/ml) | % Difference from CNTRL | Final [IFNγ] (pg/mL) | % Difference from CNTRL |
| Control | 4246 | | 24775 | |
| N-Glycan removal | 5993 | 34 | 28229 | 13 |
| Terminal sialic acid removal | 5127 | 19 | 25111 | 1 |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

| SEQUENCES | | |
|---|---|---|
| SEQ ID NO. | SEQUENCE | DESCRIPTION |
| 1 | mrkllifsis aylmagivsc kgvdsatpvt edrlalnavn apadntvnik tfdkvknafg dglsqsaegt ftfpadvttv ktikmfikne cpnktcdewd ryanvyvknk ttgewyeigr fitpy wvgte klprgleidv tdfksllsgn telkiytetw lakgreysvd fdivygtpdy kysavvpviq ynkssidgvp ygkahtlglk kniqlptnte kaylrttisg wghakpydag srgcaewcfr thtiainnan tfqhqlgalg csanpinnqs pgnwapdrag wcpgmavptridvlnnsltg stfsyeykfq swtnngtngd afyaissfvi aksntpisapvvtn | Amino acid sequence of PNGase F from Flavobacterium meningosepticum |
| 2 | ESKYGPPCPPCP | spacer (IgG4hinge) (aa) *Homo sapiens* |
| 3 | GAATCTAAGTACGGACCGCCCTGCCCCCCTTGCCCT | spacer (IgG4hinge) (nt) *homo sapiens* |
| 4 | ESKYGPPCPPCPGQPREPQVYTLPPSQEEMTKNQVSLTCLVKGFY PSDIAVEWESNGQPENNYKTTPPVLDSDGSFFLYSRLTVDKSRWQ EGNVFSCSVMHEALHNHYTQKSLSLSLGK | Hinge-CH3 spacer *Homo sapiens* |
| 5 | ESKYGPPCPPCPAPEFLGGPSVFLFPPKPKDTLMISRTPEVTCVVVD VSQEDPEVQFNWYVDGVEVHNAKTKPREEQFNSTYRVVSVLTVL HQDWLNGKEYKCKVSNKGLPSSIEKTISKAKGQPREPQVYTLPPS QEEMTKNQVSLTCLVKGFYPSDIAVEWESNGQPENNYKTTPPVL DSDGSFFLYSRLTVDKSRWQEGNVFSCSVMHEALHNHYTQKSLS LSLGK | Hinge-CH2-CH3 spacer *Homo sapiens* |
| 6 | RWPESPKAQASSVPTAQPQAEGSLAKATTAPATTRNTGRGGEEK KKEKEKEEQEERETKTPECPSHTQPLGVYLLTPAVQDLWLRDKA TFTCFVVGSDLKDAHLTWEVAGKVPTGGVEEGLLERHSNGSQSQ HSRLTLPRSLWNAGTSVTCTLNHPSLPPQRLMALREPAAQAPVKL SLNLLASSDPPEAASWLLCEVSGFSPPNILLMWLEDQREVNTSGF APARPPPQPGSTTFWAWSVLRVPAPPSPQPATYTCVVSHEDSRTL LNASRSLEVSYVTDH | IgD-hinge-Fc *Homo sapiens* |
| 7 | LEGGGEGRGSLLTCGDVEENPGPR | T2A artificial |
| 8 | MLLLVTSLLLCELPHPAFLLIPRKVCNGIGIGEFKDSLSINATNIKHF KNCTSISGDLHILPVAFRGDSFTHTPPLDPQELDILKTVKEITGFLLI QAWPENRTDLHAFENLEIIRGRTKQHGQFSLAVVSLNITSLGLRSL KEISDGDVIISGNKNLCYANTINWKKLFGTSGQKTKIISNRGENSC KATGQVCHALCSPEGCWGPEPRDCVSCRNVSRGRECVDKCNLLE GEPREFVENSECIQCHPECLPQAMNITCTGRGPDNCIQCAHYIDGP HCVKTCPAGVMGENNTLVWKYADAGHVCHLCHPNCTYGCTGP GLEGCPTNGPKIPSIATGMVGALLLLLVVALGIGLFM | tEGFR artificial |

-continued

| SEQ ID NO. | SEQUENCE | DESCRIPTION |
|---|---|---|
| 9 | FWVLVVVGGVLACYSLLVTVAFIIFWV | CD28 (amino acids 153-179 of Accession No. P10747) Homo sapiens |
| 10 | IEVMYPPPYLDNEKSNGTIIHVKGKHLCPSPLFPGPSKP FWVLVVVGGVLACYSLLVTVAFIIFWV | CD28 (amino acids 114-179 of Accession No. P10747) Homo sapiens |
| 11 | RSKRSRLLHSDYMNMTPRRPGPTRKHYQPYAPPRDFAAYR S | CD28 (amino acids 180-220 of P10747) Homo sapiens |
| 12 | RSKRSRGGHSDYMNMTPRRPGPTRKHYQPYAPPRDFAAYR S | CD28 (LL to GG) Homo sapiens |
| 13 | KRGRKKLLYIFKQPFMRPVQTTQEEDGCSCRFPEEEEGGCEL | 4-1BB (amino acids 214-255 of Q07011.1) Homo sapiens |
| 14 | RVKFSRSADAPAYQQGQNQLYNELNLGRREEYDVLDKRRG RDPEMGGKPRRKNPQEGLYN ELQKDKMAEA YSEIGMKGER RRGKGHDGLY QGLSTATKDTYDALHMQALP PR | CD3 zeta Homo sapiens |
| 15 | RVKFSRSAEPPAYQQGQNQLYNELNLGRREEYDVLDKRRG RDPEMGGKPRRKNPQEGLYN ELQKDKMAEA YSEIGMKGER RRGKGHDGLY QGLSTATKDTYDALHMQALP PR | CD3 zeta Homo sapiens |
| 16 | RVKFSRSADAPAYKQGQNQLYNELNLGRREEYDVLDKRRG RDPEMGGKPRRKNPQEGLYN ELQKDKMAEA YSEIGMKGER RRGKGHDGLY QGLSTATKDTYDALHMQALP PR | CD3 zeta Homo sapiens |
| 17 | PGGG-(SGGGG)5-P- wherein P is proline, G is glycine and S is serine | linker |
| 18 | GSADDAKKDAAKKDGKS | linker |
| 19 | RKVCNGIGIGEFKDSLSINATNIKHFKNCTSISGDLHILPVAFR GDSFTHTPPLDPQELDILKTVKEITGFLLIQAWPENRTDLHAF ENLEIIRGRTKQHGQFSLAVVSLNITSLGLRSLKEISDGDVIIS GNKNLCYANTINWKKLFGTSGQKTKIISNRGENSCKATGQV CHALCSPEGCWGPEPRDCVSCRNVSRGRECVDKCNLLEGEP REFVENSECIQCHPECLPQAMNITCTGRGPDNCIQCAHYIDG PHCVKTCPAGVMGENNTLVWKYADAGHVCHLCHPNCTYG CTGPGLEGCPTNGPKIPSIATGMVGALLLLLVVALGIGLFM | tEGFR artificial |
| 20 | EGRGSLLTCGDVEENPGP | T2A |
| 21 | GSGATNFSLLKQAGDVEENPGP | P2A |
| 22 | ATNFSLLKQAGDVEENPGP | P2A |
| 23 | QCTNYALLKLAGDVESNPGP | E2A |
| 24 | VKQTLNFDLLKLAGDVESNPGP | F2A |
| 25 | gacatccagatgacccagaccacctccagcctgagcgccagcctgggcgaccgggtgacca tcagctgccgggccagccaggacatcagcaagtacctgaactggtatcagcagaagcccgac ggcaccgtcaagctgctgatctaccacaccagccggctgcacagcggcgtgcccagccggtt tagcggcagcggctccggcaccgactacagcctgaccatctccaacctggaacaggaagata tcgccacctacttttgccagcagggcaacacactgccctacacctttggcggcggaacaaagct ggaaatcaccggcagcacctccggcagcggcaagcctggcagcggcgagggcagcacca agggcgaggtgaagctgcaggaaagcggccctggcctggtggcccccagccagagcctga gcgtgacctgcaccgtgagcggcgtgagcctgccgactacggcgtgagctggatccgca gcccccaggaagggcctggaatggctgggcgtgatctgggcagcgagaccacctactac aacagcgccctgaagagccggctgaccatcatcaaggacaacagcaagagccaggtgttcct gaagatgaacagcctgcagaccgacgacaccgccatctactactgcgccaagcactactacta cggcggcagctacgccatggactactggggccagggcaccagcgtgaccgtgagcagc | Sequence encoding scFv |
| 26 | RASQDISKYLN | FMC63 CDR L1 |
| 27 | SRLHSGV | FMC63 CDR L2 |
| 28 | GNTLPYTFG | FMC63 CDR L3 |
| 29 | DYGVS | FMC63 CDR H1 |
| 30 | VIWGSETTYYNSALKS | FMC63 CDR H2 |
| 31 | YAMDYWG | FMC63 CDR H3 |
| 32 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSS | FMC63 VH |
| 33 | DIQMTQTTSSLSASLGDRVTISCRASQDISKYLNWYQQKPD GTVKLLIYHTSRLHSGVPSRFSGSGSGTDYSLTISNLEQEDIA TYFCQQGNTLPYTFGGGTKLEIT | FMC63 VL |

SEQUENCES

| SEQ ID NO. | SEQUENCE | DESCRIPTION |
|---|---|---|
| 34 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 scFv |
| 35 | KASQNVGTNVA | SJ25C1 CDR L1 |
| 36 | SATYRNS | SJ25C1 CDR L2 |
| 37 | QQYNRYPYT | SJ25C1 CDR L3 |
| 38 | SYWMN | SJ25C1 CDR H1 |
| 39 | QIYPGDGDTNYNGKFKG | SJ25C1 CDR H2 |
| 40 | KTISSVVDFYFDY | SJ25C1 CDR H3 |
| 41 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSS | SJ25C1 VH |
| 42 | DIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 VL |
| 43 | GGGGSGGGGSGGGGS | Linker |
| 44 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSSGGGGSGGGGSGGGGSDIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 scFv |
| 45 | HYYYGGSYAMDY | FMC63 HC-CDR3 |
| 46 | HTSRLHS | FMC63 LC-CDR2 |
| 47 | QQGNTLPYT | FMC63 LC-CDR3 |

What is claimed:

1. A method for assessing cell surface glycans, the method comprising:
   (a)(i) incubating a test composition comprising a plurality of cells under conditions to release one or more glycans from the surface of cells in the test composition, wherein a sample comprising one or more cell surface glycans is generated and (a)(ii) determining the presence, absence, identity and/or level of glycans present in the sample, thereby assessing the cell surface glycan profile of the sample; or
   (b) determining the presence, absence, identity and/or level of glycans present in a sample, thereby assessing the cell surface glycan profile of the sample, wherein the sample comprises one or more glycans released from the surface of cells present in a test composition comprising a plurality of cells after incubation of the test composition under conditions to release the one or more glycans; and
   wherein the cells express a recombinant receptor or the test composition comprises cells expressing a recombinant receptor.

2. The method of claim 1, wherein cells in the test cell composition comprise whole cells or intact cells.

3. The method of claim 1, wherein the test cell composition comprises between $1 \times 10^6$ cells and $5 \times 10^6$ cells, inclusive.

4. The method of claim 1, wherein the test cell composition comprises a concentration of between $1 \times 10^5$ cells/mL and $1 \times 10^8$ cells/mL, inclusive.

5. The method of claim 1, wherein the incubation is carried out in the presence of an N-glycosidase.

6. The method of claim 5, wherein the N-glycosidase is a peptide N-glycosidase (PNGase) F.

7. The method of claim 6, wherein the PNGase F is recombinant.

8. The method of claim 6, wherein the PNGase F comprises a PGNase F of *Flavobacterium meningosepticum*, or a portion or mutant thereof that is enzymatically active.

9. The method of claim 6, wherein the PNGase F comprises an amino acid sequence that exhibits at least 85% or more sequence identity to SEQ ID NO:1 or is a portion thereof that is enzymatically active.

10. The method of claim 6, wherein the PNGase F comprises the amino acid sequence set forth in SEQ ID NO: 1.

11. The method of claim 6, wherein the amount of PNGase F is 1 unit to 5000 units, inclusive.

12. The method of claim 1, wherein the incubating the test composition is for an amount of time that is between or between about 5 minutes and 12 hours, inclusive.

13. The method of claim 1, wherein the incubating the test composition is at a temperature between 25° C. and 39° C.

14. The method of claim 1, wherein, prior to the determining the presence, absence, identity and/or level of glycans present in a sample, the method further comprises labeling glycans from the sample with a detectable label.

15. The method of claim 14, wherein the detectable label is a fluorescent label and the fluorescent label is or comprises 2-aminobenzamide (2-AB), 2-aminobenzoic acid (2-AA), 2-aminopyridine (PA), 2-Aminoacridone (AMAC), 2-aminonaphthalene trisulfonic acid (ANTS), 1-aminopyrene-3,6, 8-trisulfonic acid (APTS), 3-(Acetylamino)-6-aminoacridin (AA-Ac), 6-Aminoquinoline (6-AQ), 7-Aminomethyl-coumarin (AMC), 2-Amino (6-amido-biotinyl) pyridine (BAP), 9-Fluorenylmethoxycarbonyl (FMOC)-hydrazide, 1,2-Diamino-4,5-methylenedioxy-benzene (DMB), or o-Phenylenediamine (OPD).

16. The method of claim 14, wherein the detectable label is a fluorescent label comprising a carbamate tagging group, a quinolone fluorophore, and a tertiary amine.

17. The method of claim 1, wherein, prior to determining the presence, absence, identity and/or level of the one or more glycans, the sample is subjected to glycan purification or enrichment.

18. The method of claim 1, wherein determining the presence, absence, identity and/or level of the one or more glycans comprises subjecting the sample to mass spectrometry.

19. The method of claim 1, wherein determining the presence, absence, identity and/or level of glycans comprises subjecting the sample to liquid chromatography (LC) followed by mass spectrometry.

20. The method of claim 19, wherein the liquid chromatography is hydrophilic interaction chromatography (HILIC).

21. The method of claim 18, wherein the mass spectrometry comprises ESI-MS or-tandem mass spectrometry (MS/MS).

22. The method of claim 1, wherein the determining the presence, absence, identity and/or level of the one or more glycans comprises analyzing one or more glycan structure or structures for branching, linkages between monosaccharides and/or location of monosaccharides.

23. The method of claim 1, wherein the one or more glycans comprises high mannose N-glycans, bisected and Sialyl Lewis$^x$ N-glycans, and/or N-acetyl lactosamine containing N-glycans.

24. The method of claim 1, wherein the cells comprise stem cells, immune cells, white blood cells, peripheral blood mononuclear cells (PBMC), lymphocytes, or unfractionated T cells.

25. The method of claim 1, wherein the cells comprise T cells that are CD4+ and/or CD8+ T cells or the test cell composition comprises T cells that are CD4+ and/or CD8+ T cells.

26. The method of claim 1, wherein the recombinant receptor is or comprises a chimeric receptor and/or a recombinant antigen receptor.

27. The method of claim 1, wherein the recombinant receptor is or comprises a T cell receptor or a chimeric antigen receptor (CAR).

28. The method of claim 1, wherein:
the test cell composition comprises a concentration of between $1 \times 10^6$ cells/mL and $5 \times 10^7$ cells/mL, inclusive; or the incubation is carried out in the presence of a PNGase F comprising the amino acid sequence set forth in SEQ ID NO: 1 or a portion or mutant thereof that is enzymatically active; or the incubating the test composition is for an amount of time that between or between about 30 minutes and 6 hours, inclusive; or the incubating the test composition is at a temperature between 35° C. and 39° C.

* * * * *

```
                        SEQUENCE LISTING

<160> NUMBER OF SEQ ID NOS: 47

<210> SEQ ID NO 1
<211> LENGTH: 354
<212> TYPE: PRT
<213> ORGANISM: Flavobacterium meningosepticum
<220> FEATURE:
<221> NAME/KEY: MISC_FEATURE
<223> OTHER INFORMATION: PNGASE F

<400> SEQUENCE: 1

Met Arg Lys Leu Leu Ile Phe Ser Ile Ser Ala Tyr Leu Met Ala Gly
1               5                   10                  15

Ile Val Ser Cys Lys Gly Val Asp Ser Ala Thr Pro Val Thr Glu Asp
            20                  25                  30

Arg Leu Ala Leu Asn Ala Val Asn Ala Pro Ala Asp Asn Thr Val Asn
        35                  40                  45

Ile Lys Thr Phe Asp Lys Val Lys Asn Ala Phe Gly Asp Gly Leu Ser
    50                  55                  60

Gln Ser Ala Glu Gly Thr Phe Thr Phe Pro Ala Asp Val Thr Val
65                  70                  75                  80

Lys Thr Ile Lys Met Phe Ile Lys Asn Glu Cys Pro Asn Lys Thr Cys
                85                  90                  95

Asp Glu Trp Asp Arg Tyr Ala Asn Val Tyr Val Lys Asn Lys Thr Thr
            100                 105                 110

Gly Glu Trp Tyr Glu Ile Gly Arg Phe Ile Thr Pro Tyr Trp Val Gly
```

```
                115                 120                 125
Thr Glu Lys Leu Pro Arg Gly Leu Glu Ile Asp Val Thr Asp Phe Lys
            130                 135                 140

Ser Leu Leu Ser Gly Asn Thr Glu Leu Lys Ile Tyr Thr Glu Thr Trp
145                 150                 155                 160

Leu Ala Lys Gly Arg Glu Tyr Ser Val Asp Phe Asp Ile Val Tyr Gly
                165                 170                 175

Thr Pro Asp Tyr Lys Tyr Ser Ala Val Val Pro Val Ile Gln Tyr Asn
            180                 185                 190

Lys Ser Ser Ile Asp Gly Val Pro Tyr Gly Lys Ala His Thr Leu Gly
                195                 200                 205

Leu Lys Lys Asn Ile Gln Leu Pro Thr Asn Thr Glu Lys Ala Tyr Leu
            210                 215                 220

Arg Thr Thr Ile Ser Gly Trp Gly His Ala Lys Pro Tyr Asp Ala Gly
225                 230                 235                 240

Ser Arg Gly Cys Ala Glu Trp Cys Phe Arg Thr His Thr Ile Ala Ile
                245                 250                 255

Asn Asn Ala Asn Thr Phe Gln His Gln Leu Gly Ala Leu Gly Cys Ser
            260                 265                 270

Ala Asn Pro Ile Asn Asn Gln Ser Pro Gly Asn Trp Ala Pro Asp Arg
            275                 280                 285

Ala Gly Trp Cys Pro Gly Met Ala Val Pro Thr Arg Ile Asp Val Leu
            290                 295                 300

Asn Asn Ser Leu Thr Gly Ser Thr Phe Ser Tyr Glu Tyr Lys Phe Gln
305                 310                 315                 320

Ser Trp Thr Asn Asn Gly Thr Asn Gly Asp Ala Phe Tyr Ala Ile Ser
                325                 330                 335

Ser Phe Val Ile Ala Lys Ser Asn Thr Pro Ile Ser Ala Pro Val Val
                340                 345                 350

Thr Asn

<210> SEQ ID NO 2
<211> LENGTH: 11
<212> TYPE: PRT
<213> ORGANISM: Homo sapiens
<220> FEATURE:
<221> NAME/KEY: misc_feature
<223> OTHER INFORMATION: spacer (IgG4hinge)

<400> SEQUENCE: 2

Ser Lys Tyr Gly Pro Pro Cys Pro Pro Cys Pro
1               5                   10

<210> SEQ ID NO 3
<211> LENGTH: 36
<212> TYPE: PRT
<213> ORGANISM: Homo sapiens
<220> FEATURE:
<221> NAME/KEY: misc_feature
<223> OTHER INFORMATION: spacer (IgG4hinge)

<400> SEQUENCE: 3

Gly Ala Ala Thr Cys Thr Ala Ala Gly Thr Ala Cys Gly Gly Ala Cys
1               5                   10                  15

Cys Gly Cys Cys Cys Thr Gly Cys Cys Cys Cys Cys Thr Thr Gly
            20                  25                  30

Cys Cys Cys Thr
            35
```

<210> SEQ ID NO 4
<211> LENGTH: 119
<212> TYPE: PRT
<213> ORGANISM: Homo sapiens

<400> SEQUENCE: 4

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 5
<211> LENGTH: 229
<212> TYPE: PRT
<213> ORGANISM: Homo sapiens
<220> FEATURE:
<221> NAME/KEY: misc_feature
<223> OTHER INFORMATION: Hinge-CH2-CH3 spacer

<400> SEQUENCE: 5

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

```
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 6
<211> LENGTH: 282
<212> TYPE: PRT
<213> ORGANISM: Homo sapiens
<220> FEATURE:
<221> NAME/KEY: misc_feature
<223> OTHER INFORMATION: IgD-hinge-Fc

<400> SEQUENCE: 6

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 7
<211> LENGTH: 24
<212> TYPE: PRT
```

```
<213> ORGANISM: Artificial Sequence
<220> FEATURE:
<223> OTHER INFORMATION: T2A Sequence

<400> SEQUENCE: 7

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 8
<211> LENGTH: 357
<212> TYPE: PRT
<213> ORGANISM: Artificial Sequence
<220> FEATURE:
<223> OTHER INFORMATION: Truncated EGFR

<400> SEQUENCE: 8

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300
```

```
Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
            325                 330                 335

Thr Gly Met Val Gly Ala Leu Leu Leu Leu Val Val Ala Leu Gly
            340                 345                 350

Ile Gly Leu Phe Met
        355
```

```
<210> SEQ ID NO 9
<211> LENGTH: 27
<212> TYPE: PRT
<213> ORGANISM: Homo sapiens
<220> FEATURE:
<221> NAME/KEY: misc_feature
<223> OTHER INFORMATION: Amino acids 153-179 of CD28 Uniprot Accession
      No. P10747

<400> SEQUENCE: 9

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

```
<210> SEQ ID NO 10
<211> LENGTH: 66
<212> TYPE: PRT
<213> ORGANISM: Homo sapiens
<220> FEATURE:
<221> NAME/KEY: misc_feature
<223> OTHER INFORMATION: amino acids 114-179 of Uniprot Accession No.
      P10747

<400> SEQUENCE: 10

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65
```

```
<210> SEQ ID NO 11
<211> LENGTH: 41
<212> TYPE: PRT
<213> ORGANISM: Homo sapiens
<220> FEATURE:
<221> NAME/KEY: misc_feature
<223> OTHER INFORMATION: amino acids 180-220 of Uniprot Accession No.
      P10747

<400> SEQUENCE: 11

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

```
<210> SEQ ID NO 12
<211> LENGTH: 41
<212> TYPE: PRT
<213> ORGANISM: Homo sapiens
<220> FEATURE:
<221> NAME/KEY: misc_feature
<223> OTHER INFORMATION: CD28 (LL to GG)

<400> SEQUENCE: 12

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 13
<211> LENGTH: 42
<212> TYPE: PRT
<213> ORGANISM: Homo sapiens
<220> FEATURE:
<221> NAME/KEY: misc_feature
<223> OTHER INFORMATION: 4-1BB (amino acids 214-255 of Accession No.
      Q07011.1)

<400> SEQUENCE: 13

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 14
<211> LENGTH: 112
<212> TYPE: PRT
<213> ORGANISM: Homo sapiens
<220> FEATURE:
<221> NAME/KEY: misc_feature
<223> OTHER INFORMATION: CD3 zeta

<400> SEQUENCE: 14

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 15
<211> LENGTH: 112
<212> TYPE: PRT
<213> ORGANISM: Homo sapiens
<220> FEATURE:
<221> NAME/KEY: misc_feature
```

<223> OTHER INFORMATION: CD3 zeta

<400> SEQUENCE: 15

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 112
<212> TYPE: PRT
<213> ORGANISM: Homo sapiens
<220> FEATURE:
<221> NAME/KEY: misc_feature
<223> OTHER INFORMATION: CD3 zeta

<400> SEQUENCE: 16

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 17
<211> LENGTH: 30
<212> TYPE: PRT
<213> ORGANISM: Artificial Sequence
<220> FEATURE:
<223> OTHER INFORMATION: Linker sequence

<400> SEQUENCE: 17

Pro Gly Gly Gly Ser Gly Gly Gly Ser Gly Gly Gly Ser Gly
1               5                   10                  15

Gly Gly Ser Gly Gly Gly Ser Gly Gly Gly Pro
            20                  25                  30

<210> SEQ ID NO 18
<211> LENGTH: 17
<212> TYPE: PRT
<213> ORGANISM: Artificial Sequence
<220> FEATURE:

<223> OTHER INFORMATION: Linker sequence

<400> SEQUENCE: 18

Gly Ser Ala Asp Asp Ala Lys Lys Asp Ala Ala Lys Lys Asp Gly Lys
1               5                   10                  15

Ser

<210> SEQ ID NO 19
<211> LENGTH: 335
<212> TYPE: PRT
<213> ORGANISM: Artificial Sequence
<220> FEATURE:
<223> OTHER INFORMATION: Truncated EGFR

<400> SEQUENCE: 19

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
                100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

```
Leu Leu Leu Leu Leu Val Val Ala Leu Gly Ile Gly Leu Phe Met
            325                 330                 335
```

<210> SEQ ID NO 20
<211> LENGTH: 18
<212> TYPE: PRT
<213> ORGANISM: Artificial Sequence
<220> FEATURE:
<223> OTHER INFORMATION: T2A Sequence

<400> SEQUENCE: 20

```
Glu Gly Arg Gly Ser Leu Leu Thr Cys Gly Asp Val Glu Glu Asn Pro
1               5                   10                  15

Gly Pro
```

<210> SEQ ID NO 21
<211> LENGTH: 22
<212> TYPE: PRT
<213> ORGANISM: Artificial Sequence
<220> FEATURE:
<223> OTHER INFORMATION: P2A sequence

<400> SEQUENCE: 21

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 22
<211> LENGTH: 19
<212> TYPE: PRT
<213> ORGANISM: Artificial Sequence
<220> FEATURE:
<223> OTHER INFORMATION: P2A Sequence

<400> SEQUENCE: 22

```
Ala Thr Asn Phe Ser Leu Leu Lys Gln Ala Gly Asp Val Glu Glu Asn
1               5                   10                  15

Pro Gly Pro
```

<210> SEQ ID NO 23
<211> LENGTH: 20
<212> TYPE: PRT
<213> ORGANISM: Artificial Sequence
<220> FEATURE:
<223> OTHER INFORMATION: E2A Sequence

<400> SEQUENCE: 23

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 24
<211> LENGTH: 22
<212> TYPE: PRT
<213> ORGANISM: Artificial Sequence
<220> FEATURE:
<223> OTHER INFORMATION: F2A Sequence

<400> SEQUENCE: 24

```
Val Lys Gln Thr Leu Asn Phe Asp Leu Leu Lys Leu Ala Gly Asp Val
1               5                   10                  15

Glu Ser Asn Pro Gly Pro
```

<210> SEQ ID NO 25
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 25

```
gacatccaga tgacccagac cacctccagc ctgagcgcca gcctgggcga ccgggtgacc    60
atcagctgcc gggccagcca ggacatcagc aagtacctga actggtatca gcagaagccc   120
gacggcaccg tcaagctgct gatctaccac accagccggc tgcacagcgg cgtgcccagc   180
cggtttagcg gcagcggctc cggcaccgac tacagcctga ccatctccaa cctggaacag   240
gaagatatcg ccacctactt tgccagcag ggcaacacac tgccctacac ctttggcggc   300
ggaacaaagc tggaaatcac cggcagcacc tccggcagcg gcaagcctgg cagcggcgag   360
ggcagcacca agggcgaggt gaagctgcag gaaagcggcc ctggcctggt ggcccccagc   420
cagagcctga gcgtgacctg caccgtgagc ggcgtgagcc tgcccgacta cggcgtgagc   480
tggatccggc agccccccag gaagggcctg gaatggctgg gcgtgatctg gggcagcgag   540
accacctact acaacagcgc cctgaagagc cggctgacca tcatcaagga caacagcaag   600
agccaggtgt tcctgaagat gaacagcctg cagaccgacg acaccgccat ctactactgc   660
gccaagcact actactacgg cggcagctac gccatggact actggggcca gggcaccagc   720
gtgaccgtga gcagc                                                    735
```

<210> SEQ ID NO 26
<211> LENGTH: 11
<212> TYPE: PRT
<213> ORGANISM: Artificial Sequence
<220> FEATURE:
<223> OTHER INFORMATION: FMC63 CDR L1

<400> SEQUENCE: 26

Arg Ala Ser Gln Asp Ile Ser Lys Tyr Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 27

Ser Arg Leu His Ser Gly Val
1               5

<210> SEQ ID NO 28
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 28

Gly Asn Thr Leu Pro Tyr Thr Phe Gly
1               5

<210> SEQ ID NO 29

```
<211> LENGTH: 5
<212> TYPE: PRT
<213> ORGANISM: Artificial Sequence
<220> FEATURE:
<223> OTHER INFORMATION: FMC63 CDR H1

<400> SEQUENCE: 29

Asp Tyr Gly Val Ser
1               5

<210> SEQ ID NO 30
<211> LENGTH: 16
<212> TYPE: PRT
<213> ORGANISM: Artificial Sequence
<220> FEATURE:
<223> OTHER INFORMATION: FMC63 CDR H2

<400> SEQUENCE: 30

Val Ile Trp Gly Ser Glu Thr Thr Tyr Tyr Asn Ser Ala Leu Lys Ser
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: FMC63 CDR H3

<400> SEQUENCE: 31

Tyr Ala Met Asp Tyr Trp Gly
1               5

<210> SEQ ID NO 32
<211> LENGTH: 120
<212> TYPE: PRT
<213> ORGANISM: Artificial Sequence
<220> FEATURE:
<223> OTHER INFORMATION: FMC63 VH

<400> SEQUENCE: 32

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 33
<211> LENGTH: 107
<212> TYPE: PRT
<213> ORGANISM: Artificial Sequence
<220> FEATURE:
<223> OTHER INFORMATION: FMC63 VL
```

```
<400> SEQUENCE: 33

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 34
<211> LENGTH: 245
<212> TYPE: PRT
<213> ORGANISM: Artificial Sequence
<220> FEATURE:
<223> OTHER INFORMATION: FMC63 scFv

<400> SEQUENCE: 34

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
            165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
            195                 200                 205

Ser Leu Gln Thr Asp Asp Thr Ala Ile Tyr Tyr Cys Ala Lys His Tyr
        210                 215                 220

Tyr Tyr Gly Gly Ser Tyr Ala Met Asp Tyr Trp Gly Gln Gly Thr Ser
225                 230                 235                 240

Val Thr Val Ser Ser
```

```
                       245

<210> SEQ ID NO 35
<211> LENGTH: 11
<212> TYPE: PRT
<213> ORGANISM: Artificial Sequence
<220> FEATURE:
<223> OTHER INFORMATION: SJ25C1 CDR L1

<400> SEQUENCE: 35

Lys Ala Ser Gln Asn Val Gly Thr Asn Val Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: SJ25C1 CDR L2

<400> SEQUENCE: 36

Ser Ala Thr Tyr Arg Asn Ser
1               5

<210> SEQ ID NO 37
<211> LENGTH: 9
<212> TYPE: PRT
<213> ORGANISM: Artificial Sequence
<220> FEATURE:
<223> OTHER INFORMATION: SJ25C1 CDR L3

<400> SEQUENCE: 37

Gln Gln Tyr Asn Arg Tyr Pro Tyr Thr
1               5

<210> SEQ ID NO 38
<211> LENGTH: 5
<212> TYPE: PRT
<213> ORGANISM: Artificial Sequence
<220> FEATURE:
<223> OTHER INFORMATION: SJ25C1 CDR H1

<400> SEQUENCE: 38

Ser Tyr Trp Met Asn
1               5

<210> SEQ ID NO 39
<211> LENGTH: 17
<212> TYPE: PRT
<213> ORGANISM: Artificial Sequence
<220> FEATURE:
<223> OTHER INFORMATION: SJ25C1 CDR H2

<400> SEQUENCE: 39

Gln Ile Tyr Pro Gly Asp Gly Asp Thr Asn Tyr Asn Gly Lys Phe Lys
1               5                   10                  15

Gly

<210> SEQ ID NO 40
<211> LENGTH: 13
<212> TYPE: PRT
<213> ORGANISM: Artificial Sequence
<220> FEATURE:
<223> OTHER INFORMATION: SJ25C1 CDR H3

<400> SEQUENCE: 40
```

Lys Thr Ile Ser Ser Val Val Asp Phe Tyr Phe Asp Tyr
1               5                   10

<210> SEQ ID NO 41
<211> LENGTH: 122
<212> TYPE: PRT
<213> ORGANISM: Artificial Sequence
<220> FEATURE:
<223> OTHER INFORMATION: SJ25C1 VH

<400> SEQUENCE: 41

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
                100                 105                 110

Gly Gln Gly Thr Thr Val Thr Val Ser Ser
            115                 120

<210> SEQ ID NO 42
<211> LENGTH: 108
<212> TYPE: PRT
<213> ORGANISM: Artificial Sequence
<220> FEATURE:
<223> OTHER INFORMATION: SJ25C1 VL

<400> SEQUENCE: 42

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
            35                  40                  45

Tyr Ser Ala Thr Tyr Arg Asn Ser Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105

<210> SEQ ID NO 43
<211> LENGTH: 15
<212> TYPE: PRT
<213> ORGANISM: Artificial Sequence
<220> FEATURE:
<223> OTHER INFORMATION: Linker sequence

<400> SEQUENCE: 43

Gly Gly Gly Gly Ser Gly Gly Gly Gly Ser Gly Gly Gly Gly Ser

<210> SEQ ID NO 44
<211> LENGTH: 245
<212> TYPE: PRT
<213> ORGANISM: Artificial Sequence
<220> FEATURE:
<223> OTHER INFORMATION: SJ25C1 scFv

<400> SEQUENCE: 44

```
Glu Val Lys Leu Gln Gln Ser Gly Ala Glu Leu Val Arg Pro Gly Ser
1               5                   10                  15
Ser Val Lys Ile Ser Cys Lys Ala Ser Gly Tyr Ala Phe Ser Ser Tyr
            20                  25                  30
Trp Met Asn Trp Val Lys Gln Arg Pro Gly Gln Gly Leu Glu Trp Ile
        35                  40                  45
Gly Gln Ile Tyr Pro Gly Asp Gly Asp Thr Asn Tyr Asn Gly Lys Phe
    50                  55                  60
Lys Gly Gln Ala Thr Leu Thr Ala Asp Lys Ser Ser Ser Thr Ala Tyr
65                  70                  75                  80
Met Gln Leu Ser Gly Leu Thr Ser Glu Asp Ser Ala Val Tyr Phe Cys
                85                  90                  95
Ala Arg Lys Thr Ile Ser Ser Val Val Asp Phe Tyr Phe Asp Tyr Trp
            100                 105                 110
Gly Gln Gly Thr Thr Val Thr Val Ser Ser Gly Gly Gly Gly Ser Gly
        115                 120                 125
Gly Gly Gly Ser Gly Gly Gly Ser Asp Ile Glu Leu Thr Gln Ser
    130                 135                 140
Pro Lys Phe Met Ser Thr Ser Val Gly Asp Arg Val Ser Val Thr Cys
145                 150                 155                 160
Lys Ala Ser Gln Asn Val Gly Thr Asn Val Ala Trp Tyr Gln Gln Lys
                165                 170                 175
Pro Gly Gln Ser Pro Lys Pro Leu Ile Tyr Ser Ala Thr Tyr Arg Asn
            180                 185                 190
Ser Gly Val Pro Asp Arg Phe Thr Gly Ser Gly Ser Gly Thr Asp Phe
        195                 200                 205
Thr Leu Thr Ile Thr Asn Val Gln Ser Lys Asp Leu Ala Asp Tyr Phe
    210                 215                 220
Cys Gln Gln Tyr Asn Arg Tyr Pro Tyr Thr Ser Gly Gly Gly Thr Lys
225                 230                 235                 240
Leu Glu Ile Lys Arg
                245
```

<210> SEQ ID NO 45
<211> LENGTH: 12
<212> TYPE: PRT
<213> ORGANISM: Artificial Sequence
<220> FEATURE:
<223> OTHER INFORMATION: FMC63 HC-CDR3

<400> SEQUENCE: 45

```
His Tyr Tyr Tyr Gly Gly Ser Tyr Ala Met Asp Tyr
1               5                   10
```

<210> SEQ ID NO 46
<211> LENGTH: 7
<212> TYPE: PRT
<213> ORGANISM: Artificial Sequence
<220> FEATURE:

```
<223> OTHER INFORMATION: FMC63 LC-CDR2

<400> SEQUENCE: 46

His Thr Ser Arg Leu His Ser
1               5

<210> SEQ ID NO 47
<211> LENGTH: 9
<212> TYPE: PRT
<213> ORGANISM: Artificial Sequence
<220> FEATURE:
<223> OTHER INFORMATION: FMC63 LC-CDR3

<400> SEQUENCE: 47

Gln Gln Gly Asn Thr Leu Pro Tyr Thr
1               5
```